(12) United States Patent
Lee et al.

(10) Patent No.: US 7,781,580 B2
(45) Date of Patent: Aug. 24, 2010

(54) STILBENE DERIVATIVES AS NEW CANCER THERAPEUTIC AGENTS

(75) Inventors: Ruey-min Lee, Richmond, VA (US); Daniele Simoni, Ferrara (IT)

(73) Assignee: Virginia Commonwealth University, Richmond, VA (US)

( * ) Notice: Subject to any disclaimer, the term of this patent is extended or adjusted under 35 U.S.C. 154(b) by 694 days.

(21) Appl. No.: 11/738,813

(22) Filed: Apr. 23, 2007

(65) Prior Publication Data

US 2008/0261982 A1 Oct. 23, 2008

(51) Int. Cl.
*C07D 295/15* (2006.01)
(52) U.S. Cl. .................................................. 544/165
(58) Field of Classification Search .................. 544/165
See application file for complete search history.

(56) References Cited

OTHER PUBLICATIONS

Bergmann et al., Journal of Organic Chemistry (1947), 12, 57-66.*

\* cited by examiner

*Primary Examiner*—Rebecca L Anderson
(74) *Attorney, Agent, or Firm*—Whitham Curtis Christofferson & Cook, PC

(57) ABSTRACT

Stilbene derivatives exhibit killing and suppression of growth activity against a variety of cancer cells, and are effective at suppressing tumor growth in vivo. The stilbene derivatives may be used in the treatment of diseases characterized by cell hyperproliferation including human malignancies and non-malignant diseases such as liver cirrhosis. Stilbenes may also disrupt abnormal vessels in tumor to achieve vascular disrupting effect to suppress tumor growth. Water soluble pro-drug forms of stilbene derivatives are particularly useful in suppressing tumor growth in vivo.

1 Claim, 27 Drawing Sheets

(i): NaH, THF, rt; (ii): p-Toluenesulfonic acid, DCM; (iii):TBAF, DCM, rt; (iv): aq. NaOH 5%, MeOH, rt; (v): Zn, AcOH, rt;.(vi): HCl, MeOH.

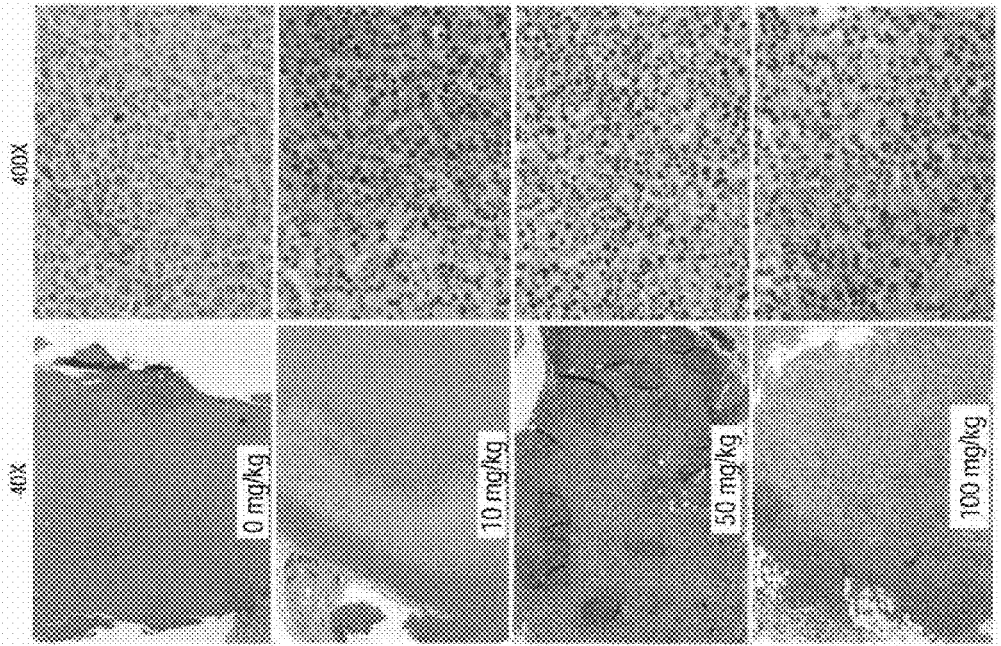
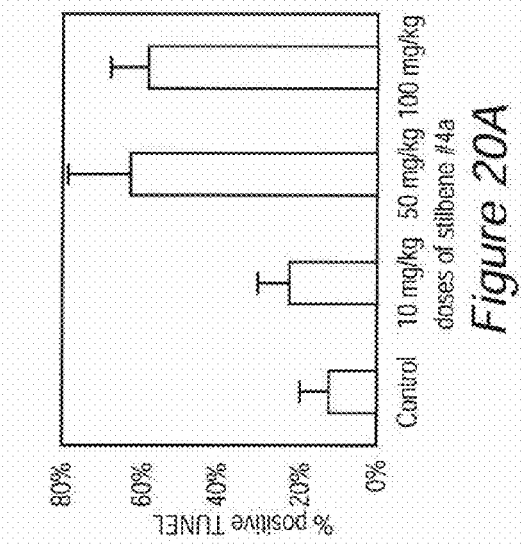
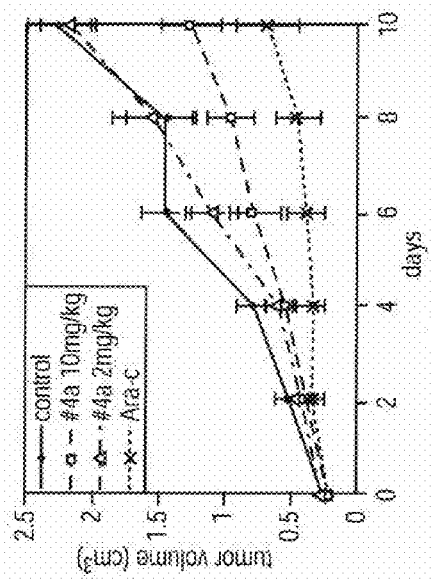
Figure 20A
Figure 20B
Figure 20C

STILBENE DERIVATIVES AS NEW CANCER THERAPEUTIC AGENTS

BACKGROUND OF THE INVENTION

1. Field of the Invention

The invention relates to stilbene derivatives that are useful for the treatment of diseases characterized by cell hyperproliferation. For example, the invention provides new stilbene derivatives including water-soluble pro-drug forms of stilbene derivatives, and contemplates use of the stilbene derivatives for the treatment of human malignancies and non-malignant diseases such as liver cirrhosis.

2. Related Art

Cancer is a deadly disease causing significant morbidity and mortality. Current existing cancer therapeutic agents provide only marginal benefit for treatment of some cancers. Thus, the development of novel agents for cancer therapy is of great interest.

Stilbenes are a group of natural compounds with a wide range of biological activities. The hydroxylated stilbene resveratrol (3,4',5-trihydroxyl-trans-stilbene) is a phytoalexin present in grapes, and plays a role in the prevention of coronary artery disease associated with red wine consumption [1]. The mechanism is related to suppression of platelet aggregation, alteration of eicosanoid synthesis and modulation of lipid metabolism. Resveratrol also has antioxidant and anti-inflammatory properties and could be a potential chemopreventive agent [17].

In addition, resveratrol has a potential therapeutic effect in suppressing tumor progression [18]. In vitro inhibition of cell proliferation [4] and in vivo anti-neovascularization by resveratrol have been demonstrated [2]. Resveratrol enhances TRAIL-induced apoptosis through G1 cell cycle arrest and depletion of survivin [19]. The apoptotic effect of resveratrol can be overcome by overexpression of Bcl-2 or FADD-DN. However, Bcl-2 or FADD-DN cannot interfere with resveratrol-mediated cell cycle arrest or survivin depletion, indicating that overexpression of Bcl-2 or FADD-DN can separate the effect of resveratrol in the cell cycle and apoptosis [19]. Resveratrol may inhibit cell migration by altering the cytoskeleton, which could be due to induction of tensin [20]. In cultured human breast cancer cell lines, resveratrol induces formation of filopodia and decreases the activity of focal adhesion kinase (FAK) and formation of focal adhesion complexes [21]. With respect to other related compounds, stilbene derivative 3,5,4'-trimethoxy-trans-stilbene induces microtubule disassembly by depolymerization of tubulin in endothelial cells, which leads to inhibition of blood vessel growth and disappearance of pre-existing blood vessels in chick and zebra fish embryos [22]. Another derivative, 3,4,5,4'-tetramethoxystilbene causes rapid appearance of perinuclear aggregation of mitochondria in WI38VA cells and activation of caspases [23], supporting a cytotoxic effect of stilbenes.

Based on the interesting anti-tumor effect of resveratrol and other stilbene derivatives, Roberti et al. synthesized a series of stilbene derivatives in both cis and trans orientations by placing OH, $NH_2$ or $OCH_3$ groups at positions 3' and 4' and $OCH_3$ at positions 3,5. The $IC_{50}$ for each of the stilbene derivatives was tested in HL60 cells. Several active stilbenes were identified, and among them, cis-3,4',5-trimethoxy-3'-aminostilbene (stilbene 5c; Scheme 1 of Roberti et al. *J. Med. Chem.* 46:3546-3554 (2003)) and cis-3,4',5-trimethoxy-3'-hydroxystilbene (stilbene 6c; Scheme 1 of Roberti et al. *J. Med. Chem.* 46:3546-3554 (2003)) were the two most active compounds that induced HL60 apoptosis in nanomolar concentrations ($IC_{50}$=30 nM) [5]. More interestingly, the cytotoxicity of these two stilbenes was not affected by overexpression of multiple-drug resistant (MDR) gene [5], a gene that is responsible for drug resistance in leukemia and many other cancers. This study illustrates the potential of using stilbene derivatives for treatment of cancer. However, the mechanism of stilbene-induced cell death remains unknown.

Microtubules play an important role in molecular transport in cells and form mitotic spindles that are essential to segregation of chromosomes. Microtubule-interfering agents have a high potency in suppressing cell proliferation [7]. The major component of microtubules is tubulin, which contains three different sites for potential drug targeting: the colchicine binding site, the vinca alkaloid binding site and the taxane binding site. The existing chemotherapeutic agents, vincristine and paclitaxel, are compounds that specifically target vinca alkaloid binding site and the taxane-binding site, respectively, and trigger cancer cell death [32]. However, compounds targeting the colchicine site are not yet available for clinical applications, although they have been pursued by many investigators [6, 7].

Tumor growth requires the development of a network of neovasculature to supply oxygen and nutrients and to remove toxic metabolites. The neovasculature formed in the tumor tissue differs significantly from normal vasculature [24, 25]. Targeting the tumor vasculature has evolved into a useful strategy to develop new cancer therapeutics [26]. Two approaches are currently used. One is to inhibit the angiogenic process by blocking angiogenic factors or their receptors to prevent the growth of new tumor vessels. This type of therapy is represented by bevacizumab, a monoclonal antibody against vascular endothelial growth factor (VEGF), and several small molecular inhibitors of the VEGF receptor tyrosine kinase [26-30]. The goal of this strategy is to suppress the development of tumor neovasculature through blocking proliferation of endothelial cells. The second strategy is to kill the existing tumor endothelial cells. Compounds with this capability are referred to as "vascular disrupting agents" (VDAs). VDAs work by shutting down existing tumor vasculature, thereby depriving the tumor of adequate oxygen and nutrients, which leads to tumor ischemia and eventually tumor necrosis [11, 31]. There are two types of VDAs. One type of VDA is ligand-based and includes antibodies, peptides and growth factors that bind selectively to tumors but not to normal vessels by targeting tumor endothelial cells and occluding tumor vasculature. The other is a group of small molecules that include CA4P, ZD6126, AVE8062 and Oxi4503. These small molecules damage tumor endothelial cells by interfering with microtubule polymerization. Other small molecules include the flavonoid DMXAA, which induces localized release of TNFα or other cytokines from activated macrophages in the tumor tissue, which results in damage to tumor vessels. Currently several of these compounds are being actively pursued in pre-clinical tumor models and some have advanced into human clinical trials.

Colchicine-site microtubule interfering agents were initially developed as vascular disrupting agents, and this ability makes them attractive candidates for use in killing tumor endothelial cells as well. However, known colchicine-site microtubule interfering agents colchicine and vincristine require a near lethal dose to have such an effect and are thus not considered to be viable candidate compounds for clinical purposes. Combretastin A4 [8] is one example of a colchicine derivative that is currently being developed as a vascular disrupting agent [9-11]. In contrast to colchicine, the desired anti-vascular effect of combretastin A4 can be achieved at a dose only one tenth of the maximal tolerated dose in animal models. Clinical studies of combretastatin A4-phosphate, a water soluble pro-drug of combretastatin A4, have also confirmed its efficacy in decreasing tumor perfusion by dynamic contrast enhanced MRI and PET scan [12-14]. However, it was also observed that combretastin A4, at a dose higher than 68 mg/m$^2$, exhibited cardiac toxicity and neurotoxicity, and also induced pain in the region of the tumor. These undesired side effects suggest that the use of combretastatin A4 for the treatment of cancer may be problematic. Another colchicine derivative, ZD6126, was also evaluated in phase I clinical trials [15]. Similar to combretastatin A4-P, cardiac toxicity (such as decreasing left ventricular ejection fraction) and dose limiting toxicity were observed. Thus, ZD6126 may also not be suitable for use in treating cancer.

There is an ongoing need to provide compounds that can be used to efficaciously treat cancer but that do not exhibit deleterious side effects.

SUMMARY OF THE INVENTION

A feature of the invention is to provide novel stilbene derivatives which are useful for killing hyperproliferating cells such as cancer cells and for the treatment human malignancies and non-malignancies, including without limitation liver cirrhosis. These stilbene derivatives can include prodrugs which have chemical leaving groups which can be separated by hydrolysis or enzymatic cleavage, particularly when present in vivo. The chemical leaving groups used in the prodrugs preferably convey a property of interest such as water solubility, lipid solubility, etc., and are biologically beneficial or at least not harmful after separation from the stilbene derivatives.

Another feature of the invention is to provide novel water-soluble prodrug forms of the stilbene derivatives, as well as use of these compounds in killing hyperproliferating cells such as cancer cells and for the treatment human malignancies and non-malignancies, including without limitation liver cirrhosis. A general structural formula is as follows:

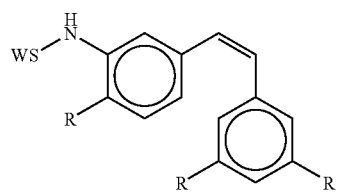

wherein WS is a water soluble moiety separable from an amido linkage to a stilbene by hydrolysis, and where R may be the same or different at each location, and is selected from hydrogen, and substituted or unsubstituted C$_{1-4}$ alkyl or alkoxy groups.

Specific examples of such novel water-soluble prodrug stilbene derivatives include:

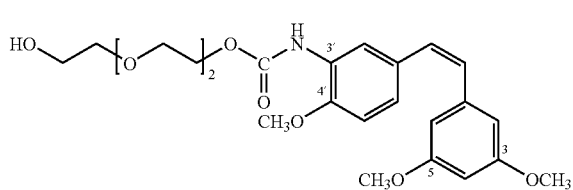

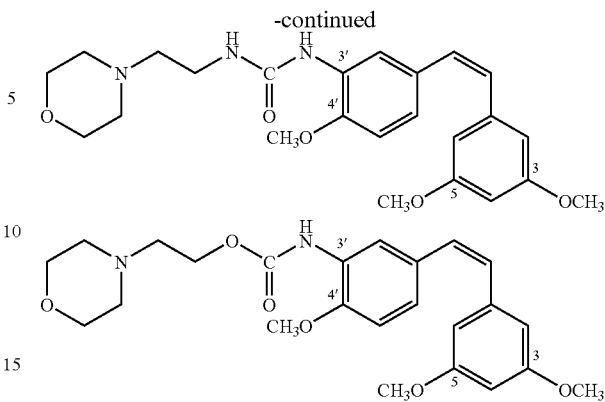

The triethylene glycol (TEG) derivative, morpholino-urea, and morpholino-carbamate derivatives have particularly beneficial biological activities. Other water-soluble prodrugs connected through the readily cleavable amido linkage are expected to have beneficial biological activities.

Yet another aspect of the invention is to provide a method of suppressing or killing cancer cells, or suppressing tumor growth in a mammal, such as a human, or treating diseases associated with hyperproliferating cells by exposing the cells, by administration to the mammal or other means to an effective amount of a stilbene derivative having the general structural formula:

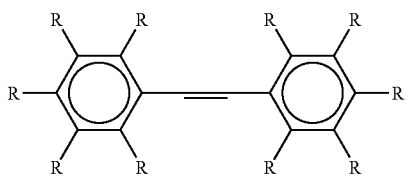

where the compound may be in the cis or trans conformation, where at least one R is a Water Soluble moiety "WS", examples of which include but are not limited to morpholino-urea, morpholino-carbamate, and triethylene glycol (the WS moiety being any moiety that can be separated from the stilbene at the amido linkage cite by hydrolysis which would occur in vivo so as to leave the biologically active stilbene analog ("derivative") in the cell), and where the R moieties can be the same or different and include hydrogen, substituted or unsubstituted C$_{1-4}$ alkyl or alkoxy groups, substituted or unsubstituted amino and amido groups, and substituted cyclic or heterocyclic aliphatic or aromatic ring moieties connecting at least two of the R groups on one of the benzene rings.

According to the invention, stilbene derivatives are prepared which are useful for the treatment of diseases characterized by cell hyperproliferation including human malignancies and non-malignant diseases such as liver cirrhosis. Cellular proliferation of breast cancer cells, ovarian cancer cells, and hepatocellular (liver) cancer cells, is blocked on exposure to the stilbene derivative. Water soluble pro-drug forms of stilbene derivatives have particularly advantageous properties for use in vivo. While less potent in vitro, experiments in vivo demonstrate significant suppression of tumor growth.

DESCRIPTION OF THE DRAWINGS

in FIG. 2a are represented the known stilbene derivatives combretastatin A4, 4a and 4c. The other structures in FIG. 2a are novel stilbene derivatives. In FIG. 2b are displayed 5a-c, the novel prodrug forms of stilbene derivative 4a. Compound 5d is another novel urea-derivative of 4a, compounds 3b,d, 8a-c,e,f, 9d,f, 9f trans and 13d are novel stilbene derivatives obtained in the synthetic route, compounds 4a trans and 4c trans are the known isomers of compound 4a and 4c.

FIG. 20. Effect of stilbene 4a in vivo. (a) Induction of cell death in vivo by stilbene 4a. Tumor was harvested at 24 hours after treatment for TUNEL assay. (b) Histological sections of tumor. Tumor harvested at 24 hours after injection of stilbene 4a was analyzed by H & E staining. The area with lighter color is the necrotic region. (c) Tumor growth suppression. SCID mice were injected subcutaneously with $5 \times 10^6$ HL60 cells at each flank. Once the diameter of tumor reached 5 mm in diameter in majority of mice, mice were treated with 5 daily injection of stilbene 4a. Tumor volume was calculated by the long and short axis of tumor and plotted against days. Each group contains 5 mice.

DETAILED DESCRIPTION

The present invention provides novel stilbene derivatives. The stilbene derivatives display anti-tumor activity, i.e. cancer cells that are exposed to the stilbene derivatives are killed or damaged, or tumor cell growth is otherwise suppressed.

Figure 1A:
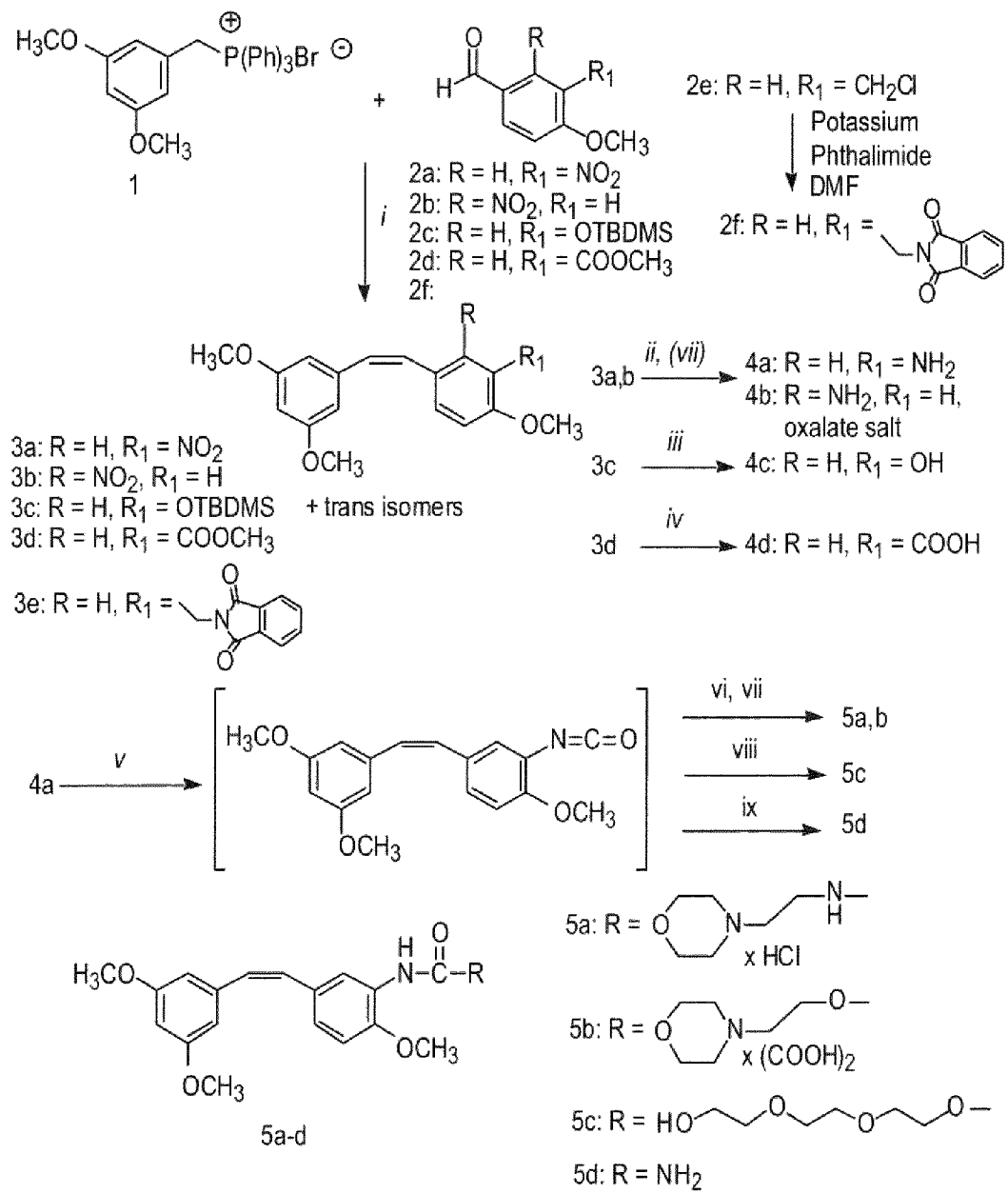
FIGS. 1a-c (also named "scheme 1", "scheme 2" and "scheme 3") show schematic synthesis routes for synthesizing stilbene derivatives.
Figure 1B:
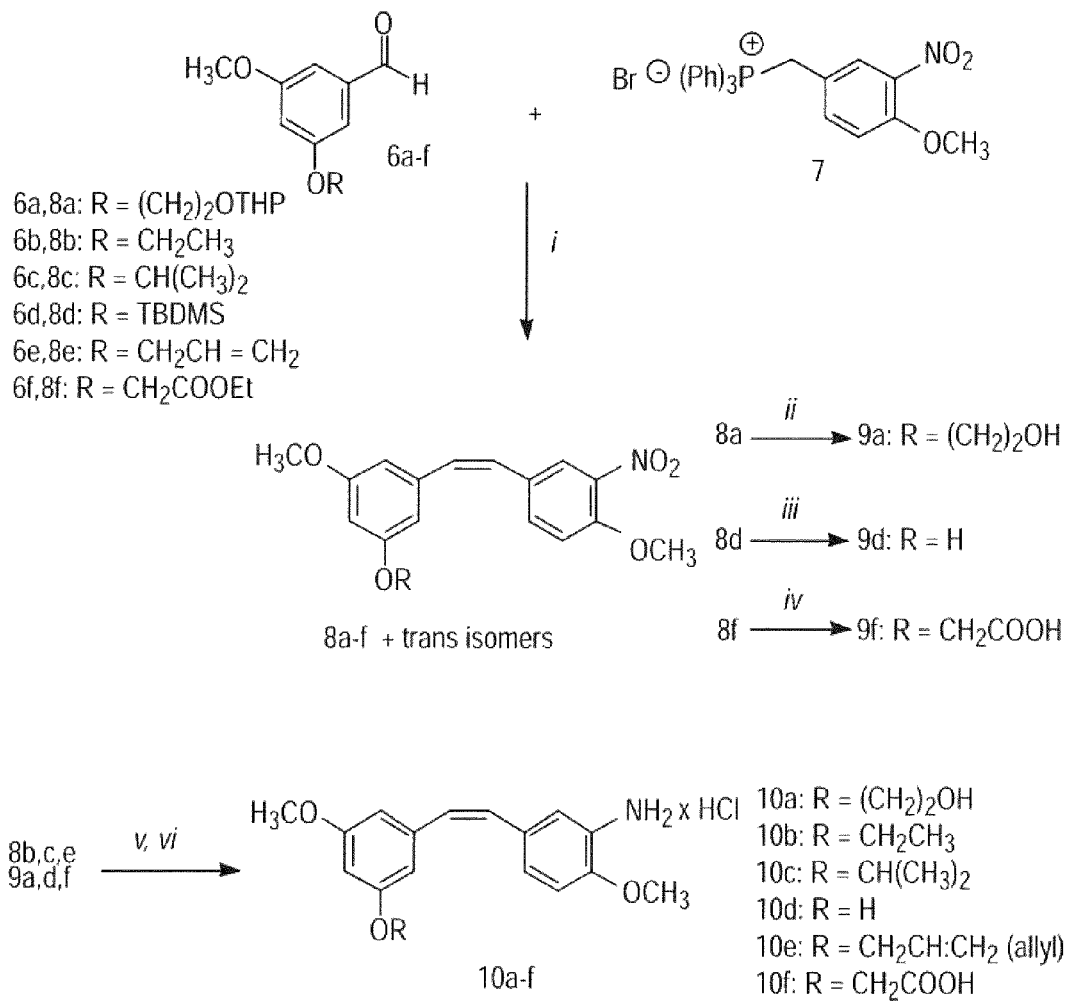
Figure 1C:
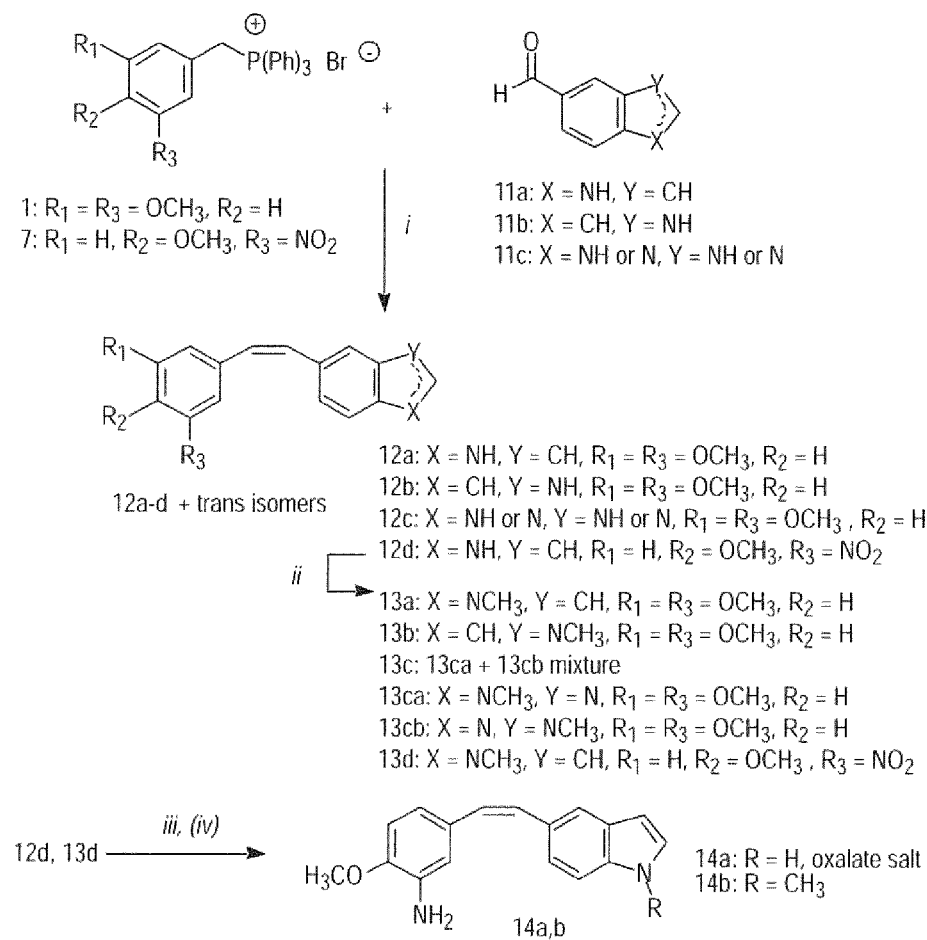
Figure 2A:
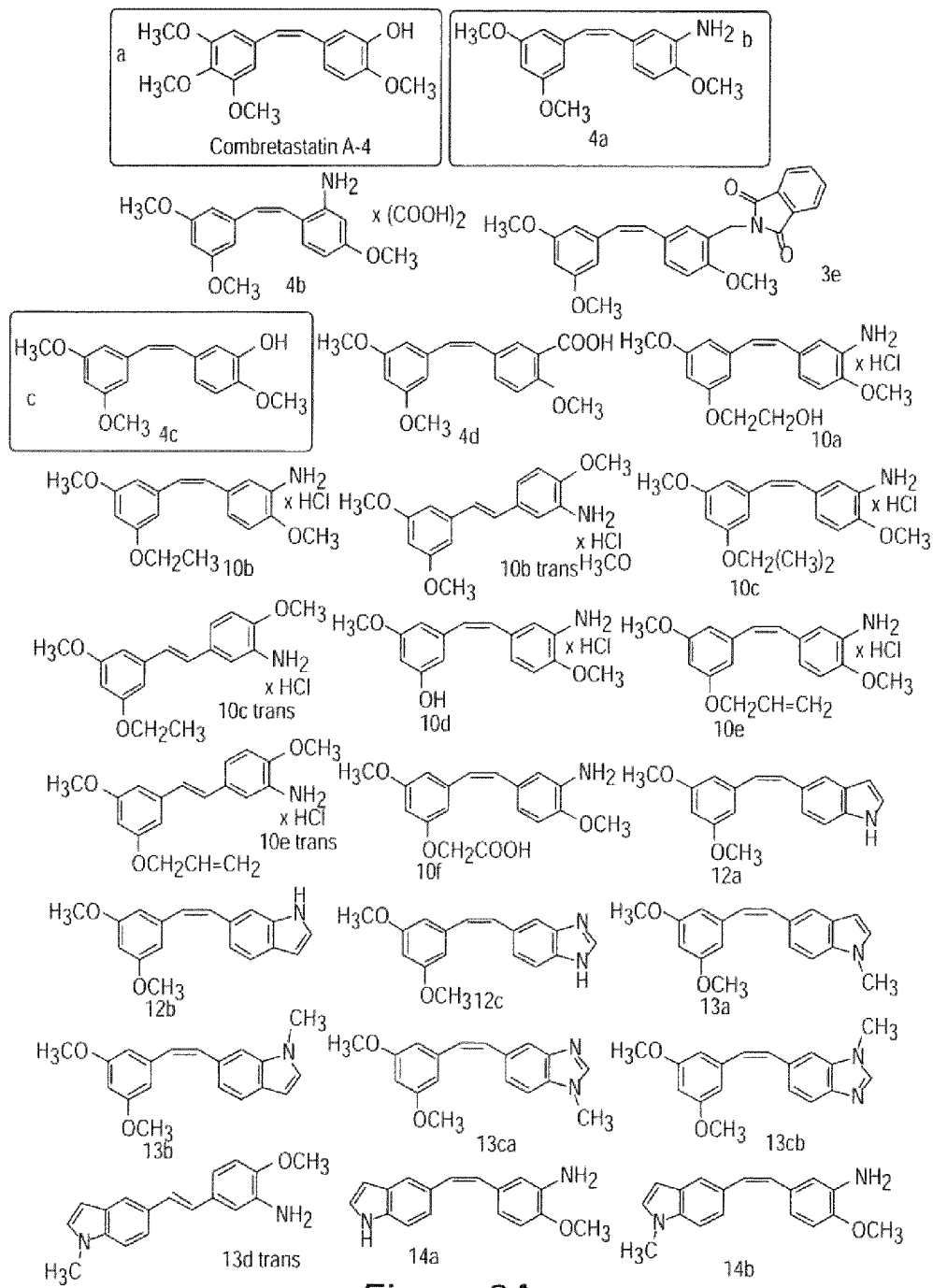
FIGS. 2a-b show the chemical structure of representative stilbene derivative.
Figure 2B:
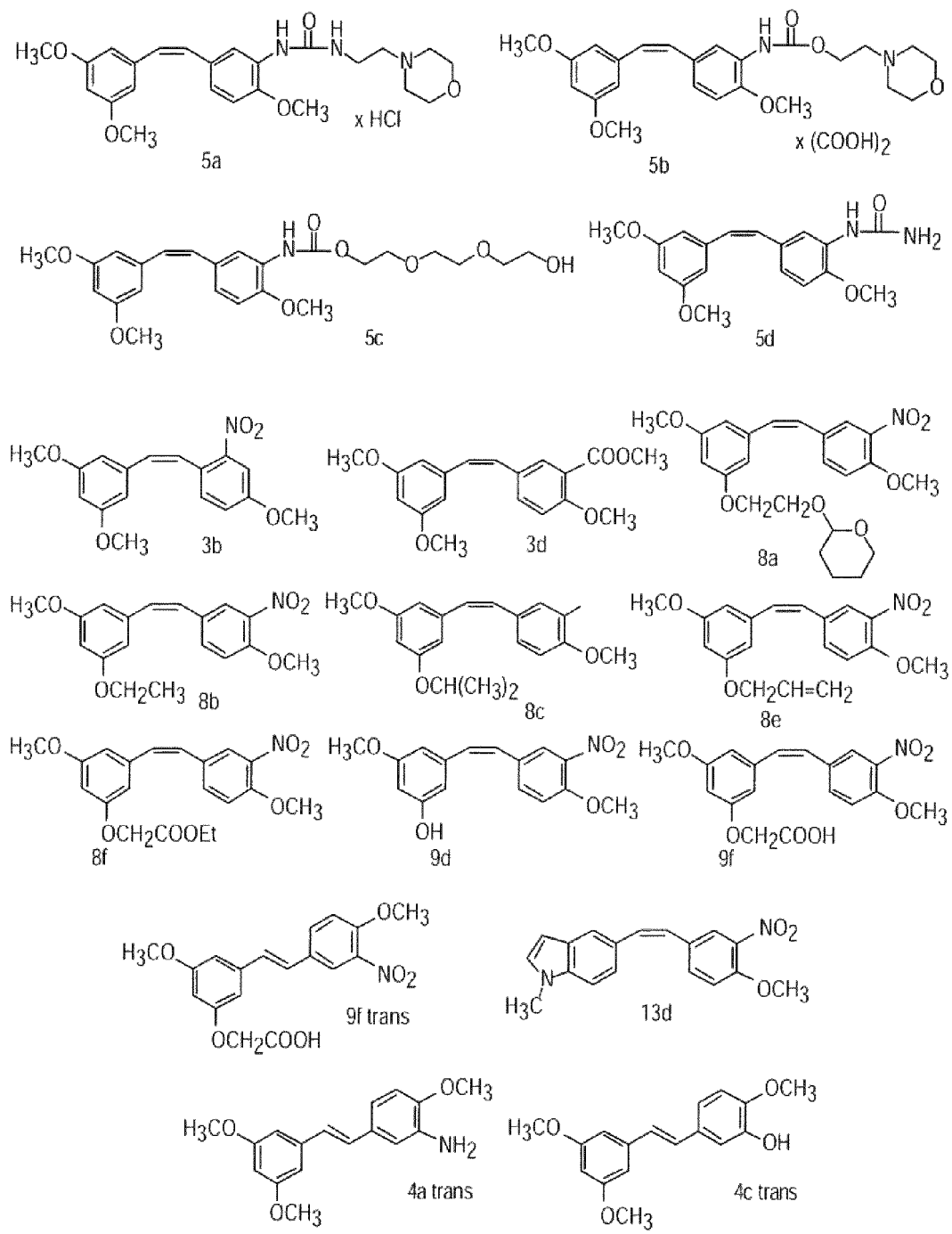

FIGS. 1a-c show different schemes for synthesizing stilbene derivatives. FIG. 2 shows exemplary stilbene derivatives which have been synthesized and tested, as is described in more detail below in the Examples section. In FIG. 2a, structure "a" depicts the known compound combretastatin A4 ((Z)-2-Methoxy-5-[2-(3,4,5-trimethoxy-phenyl)-vinyl]-phenol), "b" depicts the known compound (Z)-5-[2-(3,5-Dimethoxy-phenyl)-vinyl]-2-methoxy-phenylamine which is referred to herein as "stilbene 4a", and "c" depicts the known compound (Z)-5-[2-(3,5-Dimethoxy-phenyl)-vinyl]-2-methoxy-phenol which is referred to herein as "stilbene 4c". Several new compounds are depicted in FIG. 2a Of particular interest are stilbene derivatives that are water soluble stilbene prodrugs. FIG. 2b shows exemplary structures of certain water soluble stilbene prodrugs (5a-c). The stilbene prodrugs shown in FIG. 2b are subject to hydrolysis at the amido linkage to produce stilbene 4a, and it is believed that water soluble stilbene prodrugs are converted in vivo to stilbene 4a which is shown to have potent tumor growth suppression/tumor killing activity. Experiments set forth below demonstrate that a water soluble prodrug can suppress tumor growth in vivo by approximately 40%.

Stilbene prodrugs may be made by attaching to a stilbene derivative of interest (e.g. a stilbene derivative with anti-tumor activity), chemical groups (or moieties) that render the stilbene derivative more water soluble than before such a modification is carried out. By "water soluble" we mean that more than 20 mg compound can be fully dissolved in 1 mL of water. Further, the chemical groups that are attached to the stilbene derivative to make the derivative water soluble are labile (i.e. removable) in that, upon exposure to in vitro or in vivo hydrolyzing conditions, the chemical groups are removed or dissociated from the stilbene derivative by hydrolysis, releasing the active, anti-tumor form of the stilbene derivative. The chemical groups which are attached may themselves be biologically active, and are, at least, not biologically injurious to cells or mammals. Three exemplary prodrug forms of the stilbene derivative 4a are shown in FIG. 2b (5a-c). As can be seen, in each of these exemplary compounds, an amide bond is formed between the $NH_2$ functional group of stilbene 4a and the chemical group that is added to confer or improve aqueous solubility. As illustrated, morfolinoethyl-urea, morfolinoethyl-carbamate and triethylene glycol (TEG) groups (5a, 5b, 5c, respectively) may be used for this purpose. An example of water solubility improvement due to carbamate prodrug is reported in the following table (data at 20° C.).

| Compounds | x HCl | x $(COOH)_2$ | Free base |
|---|---|---|---|
| (structure: $H_3CO$-substituted stilbene with $NH_2$ and $OCH_3$ groups) | 6 mg/ml | <1 mg/ml | <1 mg/ml |
| (structure: stilbene carbamate with morpholinoethyl group) | 759 mg/ml | 5.9 mg/ml | <1 mg/ml |

However, those of skill in the art will recognize that other similar groups may be attached to a stilbene derivative at an $NH_2$ group, examples of which include but are not limited to amides with amino acids and small peptides, dialkylaminoalkyl groups, morfolino-alkyl groups, with polyoxydrilate chains, succinic acid (emisuccinate) and similar dicarboxylic acids, chloracetic acid and similar. Further, depending on the particular stilbene derivative, other functional groups of the stilbene may be selected for modification. For example, opportune side chain could be inserted at the benzene or heterocyclic portions (attached to a CH) for compounds of FIG. 2a, such as dialkylamino-alkyl groups, morfolino-alkyl groups, polyoxydrilate chains. Moreover carboxylic acid residues, sulfonic and sulfuric residues, phosphonic, phosphinic and phosphate residues, amines and substituted amines, alcoholic and phenolic residues can be included.

In the case of heterocyclic stilbenes, alkylamines, morfolino-alkyl groups, polyoxydrilate chains will be attached to NH. In the case of compound 4d, the carboxylic moiety will be elaborate into amides and esters with aminoacids and peptides, with dialkylamino-alkyl groups, morfolino-alkyl groups, with polyoxydrilate chains, with succinic acid and closer dicarboxylic acids. In the case of 4c, to improve its water solubility residues such as chloracetic acid, phosphates, phosphonates, esters and carbamates with dialkylamino-alkyl groups, morfolino-alkyl groups and polyoxydrilate chains, sugars to make glycosides, will be attached (37).

While such prodrugs may be made by attaching chemical groups to an active stilbene derivative, this need not be the case. Such chemical groups may be added before or after other substituents during synthesis. The water soluble prodrug stilbene derivatives may or may not have antitumor activity prior to their in vivo conversion to the active anti-tumor growth suppressing form.

Also, stilbene derivative prodrugs may be made using enzymatically cleavable chemical groups (38,39).

The invention will be better understood in view of the following definitions:

DEFINITIONS

It must be noted that as used herein and in the appended claims, the singular forms "a", "an", and "the" include plural reference unless the context clearly dictates otherwise. Thus, for example, reference to "stilbene" includes a plurality of such derivatives, reference to "the cell" is a reference to one or more cells and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The terms "higher," "increases," "enhances," "elevates," or "elevation" refer to increases above control level or basal level. The terms "low," "lower," "inhibit," "reduces," or "reduction" refer to decreases below control level or basal level. For example, basal levels are normal in vivo levels prior to, or in the absence of, addition of stilbene derivatives.

The term "test compound" is defined as any stilbene derivative to be tested.

The term "control" (e.g. "control levels" or "control cells") is defined as the standard by which a change is measured. For example, the controls are generally not subjected to the experimental variable (e.g. varying concentrations of a drug), but are instead subjected to a defined set of parameters that is the same but which does not include the experimental variable. Alternatively, a "control" may be based on pre- or post-treatment levels.

The present invention also provides pharmaceutical compositions comprising the novel compounds described herein. Generally, the compounds will be present in the compositions in the range of from about 1 to about 99%, weight/volume. Such compositions can be administered in vivo in a pharmaceutically acceptable carrier. By "pharmaceutically acceptable" is meant a material that is not biologically or otherwise undesirable, i.e., the material may be administered to a subject, without causing excessive undesirable biological effects or interacting in a deleterious manner with the components (e.g. the active ingredients) of the pharmaceutical composition in which it is contained. The carrier should be selected to minimize degradation of the active ingredient and to minimize adverse side effects in the subject, as would be well known to one of skill in the art.

Pharmaceutical carriers are known to those skilled in the art. Those most typically used would be standard carriers for administration of drugs to humans, including solutions such as sterile water, saline, and buffered solutions at physiological pH. Suitable carriers and their formulations are described, for example, in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. In addition, pharmaceutical carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of composition being administered. Pharmaceutical compositions may also include carriers, thickeners, diluents, buffers, preservatives, surface active agents and the like in addition to the compounds of the invention. Pharmaceutical compositions may also include one or more active ingredients such as antimicrobial agents, anti-inflammatory agents, anesthetics, and the like.

Preparations for parenteral administration include sterile aqueous or non-aqueous liquid solutions, suspensions, and emulsions, or solid forms suitable for solution or suspension in liquid prior to injection. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The pharmaceutical composition may be administered in a number of ways depending on whether local or systemic treatment is desired, and on the area to be treated. The compositions may be administered orally, parenterally (e.g., intravenously, for example by intravenous drip), subcutaneously, by intramuscular injection, by intraperitoneal injection, transdermally, extracorporeally, topically (including ophthalmically, and via an intracavity route such as vaginally, rectally, intranasally, etc.) or the like, including topical intranasal administration or administration by inhalant. Delivery can also be directly to any suitable area e.g. by intubation.

The compound can be given by injection into a vein (intravenously) through a cannula (a fine tube inserted into the vein). It can also be given through a central line which is inserted under the skin into a vein near the collarbone, or through a line which is inserted into a vein in the crook of the arm. It may also be injected along with embolization through a trans-arterial catheter directly into vessels feeding the tumor. In particular, such therapy is used in hepatocellular carcinoma. Parenteral administration of the composition, if used, is generally characterized by injection. A more recently revised approach for parenteral administration involves use of a slow release or sustained release system such that a constant dosage is maintained. The materials may be in solution, suspension (for example, incorporated into microparticles, liposomes, or polymers). These may be targeted to a particular cell type via antibodies, receptors, or receptor ligands. Molecular and cellular mechanisms of receptor-mediated endocytosis have been reviewed (Brown and Greene, DNA and Cell Biology 10:6, 399-409 (1991)).

The compositions of the invention can be used alone or in combination with other agents, e.g. other chemotherapeutic agents, agents which promote the health and well being of the cancer patient (medicaments to control or decrease pain, nausea, depression, etc; to treat anemia; to stimulate appetite, etc.), or dietary supplements (e.g. vitamin/mineral supplements, protein supplements, etc.), and the like. Further, the compositions may contain one or more than one of the novel compounds of the invention.

Effective dosages and schedules for administering the compositions may be determined empirically, and making such determinations is within the skill in the art. The dosage ranges for the administration of the compositions are those large enough to produce the desired effect in which the symptoms and disorders are affected. The dosage should not be so large as to cause adverse side effects, such as unwanted cross-reactions, anaphylactic reactions, and the like. Generally, the dosage will vary with the age, condition, sex and extent of the disease in the patient, route of administration, and whether or not other drugs are included in the regimen, and can be determined by one of skill in the art. The dosage can be adjusted by the individual physician in the event of any contra indications. Dosage can vary, and can be administered in one or more dose administrations daily, for one or several days. Guidance can be found in the literature for appropriate dosages for given classes of pharmaceutical products. The exact amount of the compositions required will vary from subject to subject, depending on the species, age, weight and general condition of the subject, the severity of the cancer, etc. Thus, it is not possible to specify an exact amount for every composition. However, an appropriate amount can be determined by one of ordinary skill in the art using only routine experimentation given the teachings herein.

The invention also provides methods of treating diseases in which uncontrolled cellular proliferation occurs. One example of such a disease is cancer. A non-limiting list of different types of cancers that may be treated using the compounds disclosed herein is as follows: lymphomas (Hodgkin's and non-Hodgkin's), leukemia, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general, such as B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

In addition, the compounds of the invention may be used to treat non-cancerous conditions/diseases that involve uncontrolled cellular proliferation, examples of which include but at not limited to various autoimmune diseases (e.g. psoriasis, lupus, rheumatoid arthritis and autoimmune hemolytic anemia and thrombocytopenia), liver cirrhosis, idiopathic pulmonary fibrosis.

The invention also supplies methods of killing unwanted hyperproliferating cells such as cancer cells. This method involves contacting the hyperproliferating cells with or exposing the hyperproliferating cells to one or more stilbene derivatives of the invention. During such contact or exposure, the stilbene derivative is present in an amount to cause the death of the hyperproliferating cell. Those of skill in the art will recognize that, in some cases, the cell may be killed outright. However, in other cases this may not be the case. Killing of hyperproliferating cells by the method of the invention may occur over time, or as the result of multiple exposures. Further, much benefit (e.g. to a patient who is being treated for cancer) may ensue even if the cells are not killed, but are damaged, or if their rate of growth or proliferation, or their ability to metastasize and invade other tissues, is attenuated or eliminated.

Although any methods and materials similar or equivalent to those described herein can be used in the practice or testing of the present method and compositions, the particularly useful methods, devices, and materials are as described. Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

EXAMPLES

Chemistry

General Methods and Materials. Melting points were obtained in open capillary tubes and are uncorrected. Reactions and product mixtures were routinely monitored by thin-layer chromatography (TLC) on Merck silica gel precoated F254 plates. Nuclear magnetic resonance ($^1$H-NMR, δ) spectra were determined, when not specified, in $CDCl_3$ solution using a Bruker AC-200 spectrometer and peak positions are given in parts per million downfield from tetramethylsilane as the internal standard; J values are expressed in hertz. Light petroleum ether refers to the 40-60° C. boiling range fractions. Column chromatographies were performed with Merck 60-200 mesh silica gel. All drying operations were performed over anhydrous magnesium sulphate. Column chromatography (medium pressure) was carried out using the "flash" technique. Microanalysis of all new synthesized compounds agreed within ±0.4% of calculated values.

Scheme 1.

In FIG. 1a, Scheme 1 shows the synthetic scheme for the series of 3,4',5 trimethoxy stilbene derivatives. Usual Wittig reaction between 3,5 dimethoxy benzyl triphenyl phosphonium bromide 1 and the appropriate benzaldehyde 2a-d,f is accomplished in THF using sodium hydride as base (step i). Z compounds are then separated from E stereoisomers by chromatography. Nitro derivatives 3a,b are converted into amino compounds 4a,b using zinc in glacial acetic acid solution (step ii); compound 3c, in which a phenolic group is protected as terbutyldimethylsilyl (TBDMS) ether, is treated with tetrabutylammonium fluoride (TBAF) to give 4c (step iii); alkaline hydrolisis of methyl ester 3d gives the desired carboxylic acid function of compound 4d (step iv).

Transformation of compound 4a into more water soluble prodrugs is performed using trichloroethyl chloroformate in dioxane at 60° C. for 3 hours to obtain an isocyanate intermediate (step v), which is then treated with 2-morpholino-1-ethylamine or 2-morpholino-1-ethanol or triethylen glycol, or ammonia to achieve the final urea or carbamate (step viii or ix), as 5c,d, or hydrochloric or oxalate salts 5a,b (steps vi and vii).

Example 1

Scheme 1, Step i (Z)-1-[2-(3,5-Dimethoxy-phenyl)-vinyl]-4-methoxy-2-nitrobenzene (3b)

The phosphonium salt 1 (3 mmol, 1.48 g) was suspended in 10 mL of anhydrous tetrahydrofuran (THF). The suspension is cooled in an ice bath and then NaH (55% in mineral suspension, (3.4 mmol, 148 mg) is added. After about 30 minutes, a solution of aldehyde 2b (2 mmol, 362 mg) in 5 mL of THF is added. The reaction is stirred at room temperature for 6 h, filtered on a Celite bed, and washed with THF. After solvent evaporation, the residue is dissolved in methylene chloride (20 mL), washed with water (5 mL) and brine (5 mL), dried and evaporated again. The residue is purified by flash chromatography on silica gel (30% Ethyl acetate/light petroleum) to afford the expected cis compound 3b (240 mg), and trans isomers.

Oil; Yield 38%. $^1$H NMR ($CDCl_3$): δ 3.62 (s, 6H), 3.86 (s, 3H), 6.21-6.23 (m, 2H), 6.27-6.29 (m, 1H), 6.63 (d, J=12.4, 1H), 6.83 (d, J=12.4, 1H), 6.95 (dd, J=2.6, J=8.6, 1H), 7.20 (d, J=8.6, 1H), 7.58 (d, J=2.6, 1H).

Scheme 1, Step ii

To solution of nitrostilbene 3b (1 mmol, 315 mg) in acetic acid (15 mL) is added Zn powder (100 mmol, 6.5 g). The suspension is stirred for 2 h at room temperature. The reaction mixture is filtered over Celite and concentrated. The crude material is dissolved in ethyl acetate (15 mL) and washed with sodium bicarbonate 5% (5 mL), brine (5 mL), dried ($Na_2SO_4$) and concentrated to afford the crude amino compound (285 mg), which is used for the next salification step without any further purification.

Scheme 1, Step vii (Z)2-[2-(3,5-Dimethoxy-phenyl)-vinyl]-5-methoxy-phenylamine oxalate (4b)

Compound obtained in previous step ii is dissolved in tetrahydrofuran (THF, 5 mL) and mixed with a solution of oxalic acid dihydrate (1 mmol, 126 mg) in THF (5 mL). The oxalate salt 4b separates as colourless solid that is filtered, washed with 15 mL of THF (160 mg). Recrystallized from methanol/diethyl ether. M.p. 102-105° C. Yield 43%. $^1$H NMR ($CD_3OD$): δ 3.60 (s, 6H), 3.75 (s, 3H), 6.27-6.30 (m, 1H), 6.39-6.40 (m, 3H), 6.47 (d, J=12.0, 1H), 6.50 (s, 2H), 6.58 (t, J=12, 1H), 7.0 (s, 1H).

$^{13}$C NMR: δ 55.5, 55.7, 100.7, 104.0, 107.7, 127.0, 127.5, 132.1, 132.4, 133.1, 152.3, 161.7, 162.0.

Anal. ($C_{19}H_{21}NO_7$) C, H, N.

Example 2

Scheme 1, Step iii (Z)5-[2-(3,5-Dimethoxy-phenyl)-vinyl]-2-methoxy-phenol (4c)

To a solution of silyl compound 3c (1 mmol, 400 mg) in dichloromethane (15 mL) is added tetrabutylammonium fluoride (TBAF, 1 mmol, 261 mg). The mixture is stirred at room temperature for 2 h, poured into water, and extracted with dichloromethane. The combined organic extracts are washed with brine (5 mL) and dried ($Na_2SO_4$). Removal of the solvent under reduced pressure affords a residue, which is chromatographed on silica gel, 40% ethyl acetate/light petroleum to obtain the title compound, 258 mg.

Oil. Yield 90%. $^1$H NMR ($CDC_3$): δ 3.69 (s, 3H), 3.92 (s, 3H), 4.95 (br, 1H), 6.28-6.31 (m, 2H), 6.35-6.37 (m, 1H), 6.45 (d, J=12.2, 1H), 6.57 (d, J=12.2, 1H), 6.91 (d, J=8.8, 1H), 7.40 (dd, J=2.2, J=8.8, 1H), 7.75 (d, J=2.2, 1H).

Anal. ($C_{17}H_{18}O_4$) C, H.

Example 3

Scheme 1, Step iv (Z)-5-[2-(3,5-Dimethoxy-phenyl)-vinyl]-2-methoxy-benzoic acid. (4d)

A mixture of ester 3d (1 mmol, 328 mg), methanol (10 mL), water (6 mL) and lithium hydroxide (1.5 mmol, 36 mg) is allowed to stand at 50-60° C. for 24 h. The solution is concentrated in vacuo to remove methanol, and the remaining aqueous solution is extracted with diethyl ether to separate trace amounts of unreacted ester. The aqueous solution is acidified with 1M hydrochloric acid and extracted with three portions of ethyl acetate (10 mL each). The combined organic extracts are washed with brine (5 mL) and dried ($Na_2SO_4$). Removal of the solvent under reduced pressure affords a residue, which is chromatographed on silica gel, 40% ethyl acetate/light petroleum.

Oil. 299 mg. Yield 95%. $^1$H NMR ($CDCl_3$): δ 3.68 (s, 6H), 4.04 (s, 3H), 6.35 (t, J=2.0, 1H), 6.37 (d, J=2.0, 2H), 6.52 (d, J=12.0, 1H), 6.58 (d, J=12.0, 1H), 6.87 (d, J=8.4, 1H), 7.45 (dd, J=2.0, J=8.4, 1H), 8.11 (d, J=2.0, 1H), 11.55 (br, 1H). $^{13}$C NMR: δ 55.4, 56.8, 99.9, 106.7, 111.4, 128.5, 130.6, 131.5, 134.7, 135.4, 138.8, 160.8.

Anal. ($C_{18}H_{18}O_5$) C, H.

Example 4

Scheme 1, Step v

To a mixture of amino stilbene 4a (0.6 mmol, 173 mg) and dry dioxane (5 mL) is added trichloromethyl chloroformate (0.28 mmol, 35 μL). The mixture is heated at 60° C. for 2 h. After cooling down to room temperature, the mixture is concentrated in vacuo. The crude residue is used for the next reaction without any further purification.

Scheme 1, Step vi (Z)-{5-[2-(3,5-Dimethoxy-phenyl)-vinyl]-2-methoxy-phenyl}-carbamic acid 2-morpholin-4-yl-ethyl ester To a solution of crude isocyanate (0.59 mmol, 180 mg), obtained from previous step v, in dry dioxane (5 mL) is added 4-(2-hydroxylethyl) morpholine, (0.6 mmol, 74 μL). The mixture is heated at 60° C. for 12 h. After cooling down to room temperature, the mixture is concentrated in vacuo. The residue is purified by flash chromatography (3% methanol/dichloromethane) on silica gel to afford 117 mg of the expected title compound.

Oil; Yield 45%. $^1$H NMR ($CDCl_3$): δ 2.49-2.54 (m, 4H), 2.63-2.69 (m, 2H), 3.66 (s, 6H), 3.70-3.80 (m, 4H), 3.82 (s, 3H), 4.27 (t, J=5.8, 2H), 6.30 (t, J=2.2, 1H), 6.41-6.50 (m, 4H), 6.66 (d, J=8.6, 1H), 6.91 (dd, J=2.2, J=8.6, 1H), 7.24 (s, 1H), 8.0 (d, J=2.2, 1H).

$^{13}$C NMR: δ 53.9, 55.3, 55.8, 57.5, 61.8, 69.9, 99.7, 106.7, 109.6, 119.3, 123.5, 127.3, 129.2, 130.1, 130.5, 139.4, 146.3, 160.5.

Scheme 1, Step vii (Z)-{5-[2-(3,5-Dimethoxy-phenyl)-vinyl]-2-methoxy-phenyl}-carbamic acid 2-morpholin-4-yl-ethyl ester, oxalate salt (5b)

Compound obtained in previous step vi is dissolved in tetrahydrofuran (THF, 7 mL) and mixed with a solution of oxalic acid (0.27 mmol, 34 mg) in THF (5 mL). The oxalate salt 5b separates as colorless solid that is filtrated and washed with 10 mL of THF.

122 mg. Yield 90%. M.p. 135-137° C. $^1$H NMR ($CDCl_3$): δ 3.20-3.40 (m, 6H), 3.67 (s, 6H), 3.85 (s, 3H), 4.00 (m, 4H), 4.50 (m, 2H), 6.31 (t, J=2.2, 1H), 6.42 (d, J=2.2, 2H), 6.49 (dd, J=12.0, 2H), 6.69 (d, J=8.2, 1H), 6.94 (dd, J=2.2, J=8.2, 1H), 7.30 (s, 1H), 7.92 (s, 1H).

$^{13}$C NMR: δ 52.8, 55.3, 55.9, 56.7, 64.0, 99.8, 106.7, 109.9, 119.5, 129.3, 130.1, 130.3, 139.4, 160.6, 163.2.

Anal. ($C_{26}H_{32}N_2O_{10}$) C, H, N.

Example 5

Scheme 1, Step vi (Z)1-{5-[2-(3,5-Dimethoxy-phenyl)-vinyl]-2-methoxy-phenyl}-3-(2-morpholin-4-yl-ethyl)-urea To a solution of crude isocyanate (0.61 mmol, 200 mg), obtained from previous step v, in dry dioxane (5 mL) is added 4-(2-aminoethyl) morpholine, (0.67 mmol, 88 mg). The mixture is heated at 60° C. for 12 h. After cooling down to room temperature, the mixture is concentrated in vacuo. The residue is purified by flash chromatography (3% methanol/dichloromethane) on silica gel to afford 105 mg of the expected title compound.

Oil; Yield 39%. $^1$H NMR ($CDCl_3$): δ 2.43-2.52 (m, 6H), 3.32-3.37 (m, 2H), 3.66 (s, 6H), 3.70-3.72 (m, 4H), 3.82 (s, 3H), 6.30 (t, J=2.6, 1H), 6.42 (d, J=2.6, 2H), 6.43 (d, J=12.2, 1H), 6.53 (d, J=12.0, 1H), 6.53 (d, J=12.2, 1H), 6.68 (d, J=8.4, 1H), 6.74 (s, 1H), 6.93 (dd, J=2.2, J=8.4, 1H), 7.86 (d, J=2.2, 1H).

$^{13}$C NMR: δ 36.6, 53.4, 55.3, 55.8, 57.6, 67.0, 99.7, 106.7, 109.1, 120.8, 123.3, 128.2, 129.1, 130.2, 130.5, 139.5, 147.6, 155.3, 160.5.

Scheme 1, Step vii (Z)1-{5-[2-(3,5-Dimethoxy-phenyl)-vinyl]-2-methoxy-phenyl}-3-(2-morpholin-4-yl-ethyl)-urea, hydrochloride (5a)

Compound obtained in previous step vi is dissolved in ethyl acetate containing a slight excess of HCl and the solution is stirred about 10 min. The solvent is evaporated in vacuo and the solid residue is washed twice with few mL of diethyl ether to give 80 mg of title compound.

Yield 70%. $^1$H NMR ($CDCl_3$): δ 2.83-3.02 (m, 2H), 3.15-3.30 (m, 2H), 3.46-3.66 (m, 8H), 3.67-3.78 (m, 2H), 3.81 (s, 3H), 3.94-4.10 (m, 2H), 4.16-4.35 (m, 2H), 6.26 (t, J=2.4, 1H), 6.40 (d, J=12.6, 1H), 6.42 (d, J=2.4, 2H), 6.52 (d, J=12.6, 1H), 6.63, 6.67 (m, 1H), 6.90 (dd, J=1.6, J=8.4, 1H), 7.39 (s, 1H), 8.0 (s, 1H).

$^{13}$C NMR: δ 36.0, 53.8, 55.8, 56.5, 60.2, 65.2, 100.8, 108.0, 111.4, 121.8, 125.1, 129.3, 130.4, 131.4, 131.7, 140.8, 149.5, 159.4, 162.2.

Anal. ($C_{24}H_{32}ClN_3O_5$) C, H, Cl, N.

Example 6

Scheme 1, Step viii (Z)-{5-[2-(3,5-Dimethoxy-phenyl)-vinyl]-2-methoxy-phenyl}-carbamic acid-2-[2-(2-hydroxy-ethoxy)-ethoxy]-ethyl ester (5c)

To solution of triethylene glycol (TEG, 5 mmol, 0.67 mL) in dry dioxane (5 mL) is added dropwise the crude isocyanate (0.49 mmol, 160 mg) dissolved in dry dioxane (3 mL). The reaction mixture was heated at 60° C. for 48 h. After cooling down to room temperature, the mixture was concentrated in vacuo. The residue was purified by flash chromatography (3% methanol/dichloromethane) on silica gel to afford the expected compound.

Oil, 200 mg; Yield 89%. $^1$H NMR (CDCl$_3$): δ 3.61-3.76 (m, 13H), 3.81 (s, 3H), 4.29-4.34 (m, 2H), 6.30 (t, J=2.2, 1H), 6.43 (d, J=12.0, 1H), 6.44 (d, J=2.2, 2H), 6.53 (d, J=12.0, 1H), 6.56 (d, J=8.4, 1H), 6.92 (d, J=2.2, J=8.4, 1H), 7.93 (s, 1H), 8.02 (d, J=2.2, 1H).

$^{13}$C NMR: δ 55.3, 55.8, 61.8, 64.0, 69.5, 70.4, 70.6, 72.5, 99.8, 106.7, 109.7, 119.3, 123.5, 127.3, 129.1, 130.1, 130.5, 139.4, 146.9, 153.2, 160.5.

Anal. (C$_{24}$H$_{31}$NO$_8$) C, H, N.

Example 7

Scheme 1, Step ix

{5-[2-(3,5-Dimethoxy-phenyl)-vinyl]-2-methoxy-phenyl}-urea (5d)

To the solution of crude isocyanate obtained from compound 4a (0.52 mmol, 150 mg) in dioxane, obtained from previous step v, is bubbled ammonia until saturation, and the mixture is stirred 1 h at room temperature. A white solid appears in the solution. After evaporation of dioxane, the residue is added of water and extracted three times with ethyl acetate. The combined organic phases are dried (sodium sulfate), the solvent removed in vacuo, and the residue is purified by chromatography (5% methanol/chloroform) to obtain 164 mg of title compound.

Yield 95%. $^1$H NMR (CDCl$_3$): δ 3.67 (s, 3H), 3.70 (s, 6H), 4.69 (s, 2H), 6.30 (t, J=2.4, 2H), 6.42 (d, J=2.4, 2H), 6.46 (d, J=12.4, 1H), 6.53 (d, J=12.4, 1H), 6.71 (d, J=8.4, 1H), 6.78 (s, 1H), 6.95 (dd, J=8.4, J=2.4, 1H), 7.69 (d, J=2.4, 1H).

$^{13}$C NMR: δ 55.3, 55.8, 99.4, 106.8, 110.3, 121.5, 124.6, 129.3, 130.1, 130.3, 139.6, 148.3, 156.1, 160.7.

Anal. (C$_{18}$H$_{20}$N$_2$O$_4$) C, H, N.

Example 8

4-Methoxy-3-[(1,3-dioxoisoindolin-2-yl)methyl]benzaldehyde (2f)

To a solution of chloro derivative 2e (0.54 mmol, 100 mg) in DMF (5 mL) are added potassium phthalimide (1.3 mmol, 240 mg). The mixture is stirred at 65° C. for 5 h. After cooling down to room temperature the solution is diluted with water (10 mL), filtered and the filtrate extracted with methylene chloride (2×5 mL). Next, the organic phase is washed with brine (5 mL), dried, the solvent evaporated to afford the expected product.

M.p. 109-111° C. Yield 78% (125 mg).

$^1$H NMR (CDCl$_3$) 3.95 (s, 3H), 4.93 (s, 2H), 6.97 (d, J=8.0, 1H), 7.64 (d, J=2, 1H), 7.72-7.79 (m, 3H), 7.81-7.90 (m, 2H), 9.81 (s, 1H).

Other Compounds Obtained from Scheme 1.

(Z)-5-[2-(3,5-Dimethoxy-phenyl)-vinyl]-2-methoxy-benzoic acid methyl ester (3d)

$^1$H NMR (CDCl$_3$): δ 3.67 (s, 6H), 3.85 (s, 3H), 3.88 (s, 3H), 6.33 (t, J=2.4, 1H), 6.41 (d, J=2.4, 2H), 6.49 (d, J=12.4, 1H), 6.52 (d, J=12.4, 1H), 6.81 (d, J=8.4, 1H), 7.36 (dd, J=2.4, J=8.4, 1H), 7.75 (d, J=2.4, 1H).

$^{13}$C NMR: δ 52.1, 55.3, 56.1, 100.0, 106.6, 111.7, 119.7, 129.1, 129.2, 129.9, 132.5, 134.1, 139.1, 158.2, 160.7, 166.5.

(Z)-2-{5-[2-(3,5-Dimethoxy-phenyl)-vinyl]-2-methoxy-benzyl}-isoindole-1,3-dione (3e)

$^1$H NMR (CDCl$_3$) 3.58 (s, 6H), 3.83 (s, 3H), 4.79 (s, 2H), 6.01 (t, J=2.2, 1H), 6.27 (d, J=2.2, 2H), 6.35 (d, J=12, 1H), 6.73 (d, J=8.6, 1H), 6.93 (d, J=2.2, 1H), 7.13 (dd, J=2.2, J=8.4, 1H), 7.70-7.74 (m, 2H), 7.81-7.85 (m, 2H).

Anal. (C$_{26}$H$_{23}$NO$_3$) C, H, N.

Scheme 2.

In FIG. 1b, Scheme 2 shows the synthesis of stilbenes modified at the oxygenated function in position 3. 3-Hydroxy-5-methoxy benzaldehyde is either protected at phenol function as terbutyldimethylsilyl (TBDMS) ether, or variously alkylated as described in literature and not reported in scheme. Wittig reaction is carried out from these aldehyde derivatives 6a-f and 4-Methoxy-3-nitrobenzyl triphenyl phosphonium bromide 7 with sodium hydride in THF solution (step i, as described in step i of scheme 1). After separation of Z compound from E isomer, the former is treated to take away any present protective group. p-Toluenesulfonic acid for the tetrahydropyranyl (THP) protection of 8a (step ii), tetrabutyl ammonium fluoride (TBAF) is used for the TBDMS group of 8d (step iii, as described in step iii of scheme 1), sodium hydroxide in water/methanol solution for the ester hydrolysis of 8f (step iv, as described in step iv of scheme 1). Finally, reduction of nitro to amino group is obtained with zinc in acetic acid solution (step v, as described in step ii of scheme 1), followed by hydrochloric salt formation (step vi, as described in step vii of scheme 1).

Example 9

Scheme 2, Step ii (Z)-2-{3-Methoxy-5-[2-(4-methoxy-3-nitro-phenyl)-vinyl]-phenoxy}-ethanol (9a)

The pyranil derivative 8a (0.5 mmol, 214 mg) is dissolved in 20 mL methylene chloride, and the resulting solution is stirred at room temperature with a catalytic amount (about 10 mg) of p-toluenesulfonic acid for 2 h. The solution is washed with 5% sodium bicarbonate, brine (5 mL each), dried (Na$_2$SO$_4$) and concentrated. The residue is purified by flash chromatography on silica gel (40% ethyl acetate/light petroleum) to afford the expected compound.

Yield 90% (194 mg). $^1$H NMR (CDCl$_3$): δ 2.2 (br, 1H), 3.92 (s, 3H), 3.90-3.93 (m, 5H), 3.95-3.97 (m, 2H), 6.38 (t, J=2.0, 1H), 6.40 (t, J=2.0, 2H), 6.47 (d, J=12.4, 1H), 6.60 (d, J=12.4, 1H), 6.92 (d, J=8.8, 1H), 7.40 (dd, J=2.4, J=8.8, 1H), 7.76 (d, J=2.4, 1H).

From procedures described in scheme 2 the following new compounds have been obtained:

(Z)-2-{3-[2-(3-Amino-4-methoxy-phenyl)-vinyl]-5-methoxy-phenoxy}-ethanol, hydrochloride (10a)

Recrystallized from methanol/diethyl ether. M.p. 157-159° C. $^1$H NMR (CD$_3$OD): δ 3.67 (s, 3H), 3.80-3.82 (m, 2H), 3.88-3.90 (m, 2H), 3.96 (s, 3H), 6.38-6.40 (m, 3H), 6.54 (d, J=12.4, 1H), 6.60 (d, J=12.4, 1H), 7.12 (d, J=8.4, 1H), 7.25 (d, J=2.4, 1H), 7.35 (dd, J=2.4, J=8.4, 1H), 7.76 (d, J=2.4, 1H).

Anal. (C$_{18}$H$_{22}$ClNO$_4$) C, H, Cl, N.

(Z)-5-[2-(3-Ethoxy-5-methoxy-phenyl)-vinyl]-2-methoxy-phenylamine, hydrochloride (10b)

Recrystallized from methanol/diethyl ether. M.p 127-131° C. $^1$H NMR (CD$_3$OD): δ 1.30 (t, J=7.2 3H), 3.66 (s, 3H), 3.88 (q, J=7.2, 2H), 3.96 (s, 3H), 6.33-6.35 (m, 3H), 6.54 (d, J=12.0, 1H), 6.60 (d, J=12.0, 1H), 7.12 (d, J=8.8, 1H), 7.23 (d, J=2.2, 1H), 7.33 (dd, J=2.2, J=8.8 1H).
$^{13}$C NMR: δ 15.2, 55.7, 56.9, 64.6, 101.2, 107.6, 108.1, 113.2, 125.1, 129.5, 132.0, 132.1, 140.2, 153.1, 161.7, 162.4.
Anal. (C$_{18}$H$_{22}$ClNO$_3$) C, H, Cl, N.

(Z)-5-[2-(3-Isopropoxy-5-methoxy-phenyl)-vinyl]-2-methoxy-phenylamine, hydrochloride (10c)

Recrystalized from methanol/diethyl ether. M.p. 120-122° C. $^1$H NMR (CD$_3$OD): δ 1.20 (d, J=6.2, 6H), 3.65 (s, 3H), 3.95 (s, 3H), 4.35-4.48 (m, 1H), 6.31-6.35 (m, 3H), 6.53 (d, J=12.2, 1H), 6.60 (d, J=12.2, 1H), 7.11 (d, J=8.6, 1H), 7.22 (d, J=2.0, 1H), 7.33 (dd, J=2.0, J=8.6 1H).
$^{13}$C NMR: δ 22.5, 55.8, 57.1, 71.2, 102.7, 107.9, 109.8, 112.5, 113.4, 125.3, 129.5, 132.3, 133.3, 140.3, 153.2, 160.1, 162.6.
Anal. (C$_{19}$H$_{24}$ClNO$_3$) C, H, N.

(Z)-3-[2-(3-Amino-4-methoxy-phenyl)-vinyl]-5-methoxy-phenol, hydrochloride (10d)

Recrystallized from methanol/diethyl ether. $^1$H NMR (CD$_3$OD): δ 3.77 (s, 3H), 3.85 (s, 3H), 6.24 (s, J=2.2, 2H), 6.53-6.54 (m, 3H), 6.82-6.85 (m, 3H), 6.91 (s, 1H), 6.97 (d, J=2.2, 1H).
Anal. (C$_{16}$H$_{18}$ClNO$_3$) C, H, Cl, N

(Z)-5-[2-(3-Allyloxy-5-methoxy-phenyl)-vinyl]-2-methoxy-phenylamine, hydrochloride (10e)

Recrystallized from methanol/diethyl ether. M.p. 122-125° C.; $^1$H NMR (CD$_3$OD): δ 3.65 (s, 3H), 3.96 (s, 3H), 4.40 (dt, J=1.6, J=5.2, 2H), 5.18 (dq, J=1.4, J=10.4, 1H), 5.34 (dq, J=1.4, J=17.2, 1H), 5.88-6.07 (m, 1H), 6.37 (s, 3H), 6.53 (d, J=12.2, 1H), 6.60 (d, J=12.2, 1H), 7.11 (d, J=8.4, 1H), 7.25 (d, J=2.0, 1H), 7.34 (dd, J=2.0, J=8.4 1H).
$^{13}$C NMR: δ 55.9, 57.1, 70.0, 101.6, 108.1, 108.7, 113.4, 117.6, 125.4, 129.6, 132.1, 132.5, 135.0, 140.3, 153.3, 161.5, 162.6.
Anal. (C$_{19}$H$_{22}$ClNO$_3$) C, H, Cl, N.

(Z)-{3-[2-(3-Amino-4-methoxy-phenyl)-vinyl]-5-methoxy-phenoxy}-acetic acid (10f)

$^1$H NMR (DMSO) 3.60 (s, 6H), 3.73 (s, 3H), 4.43 (s, 2H), 6.29 (t, J=2.0, 1H), 6.37 (d, J=12.6, 1H), 6.41-6.50 (m, 4H), 6.63 (d, J=1.8, 1H), 6.71 (d, J=8.4, 1H). Anal. (C$_{18}$H$_{19}$NO$_5$) C, H, N.

Other Compounds Obtained from Scheme 2.

(Z)-2-(2-{3-Methoxy-5-[2-(4-methoxy-3-nitro-phenyl)-vinyl]-phenoxy}-ethoxy)-tetrahydro-pyran (8a)

$^1$H NMR (CDCl$_3$): δ 1.53-160 (m, 4H), 1.70-175 (m, 1H), 1.78-1.84 (m, 1H), 3.48-3.55 (m, 1H), 3.69 (s, 3H), 3.72-3.78 (m, 1H), 3.85-3.91 (m, 1H), 3.97 (s, 3H), 3.99-4.02 (m, 3H), 4.66-4.68 (m, 1H), 6.37-6.40 (m, 3H), 6.45 (d, J=12.0, 1H), 6.59 (d, J=12.0, 1H), 6.91 (d, J=8.4, 1H), 7.42 (dd, J=2.0, J=8.4, 1H), 7.76 (d, J=2.4, 1H).

(Z)-5-[2-(3-Ethoxy-5-methoxy-phenyl)-vinyl]-2-methoxy-nitrobenzene (8b)

$^1$H NMR (CDCl$_3$): δ 1.35 (t, J=7.0 3H), 3.69 (s, 3H), 3.90 (q, J=7.0, 2H), 3.92 (s, 3H), 6.35-6.38 (m, 3H), 6.45 (d, J=1.8, 1H), 6.60 (d, J=11.8, 1H), 6.91 (d, J=8.8, 1H), 7.40 (dd, J=2.2, J=8.8 1H), 7.75 (d, J=2.2, 1H), 7.76 (d, J=2.4, 1H).
$^{13}$C NMR: δ 14.9, 55.4, 56.4, 63.6, 100.9, 106.6, 107.1, 113.1, 126.1, 127.5, 129.7, 131.5, 134.7, 138.4, 151.7, 160.3, 160.9.

(Z)-5-[2-(3-Isopropoxy-5-methoxy-phenyl)-vinyl]-2-methoxy-nitrobenzene (8c)

$^1$H NMR (CDCl$_3$): δ 1.24-1.26 (m, 6H), 3.69 (s, 3H), 3.92 (s, 3H), 4.35-4.40 (m, 1H), 6.33-6.35 (m, 3H), 6.46 (d, J=12.0, 1H), 6.60 (d, J=12.0, 1H), 6.91 (d, J=8.8, 1H), 7.40 (dd, J=2.0, J=8.8 1H), 7.76 (d, J=2.0, 1H).
$^{13}$C NMR: δ 22.1, 56.3, 56.6, 70.1, 101.9, 106.5, 108.3, 113.2, 125.2, 127.1, 129.8, 131.6, 134.7, 138.4, 151.8, 159.2, 160.9.

(Z)-5-[2-(3-Allyloxy-5-methoxy-phenyl)-vinyl]-2-methoxy-nitrobenzene (8e)

$^1$H NMR (CDCl$_3$): δ 3.69 (s, 3H), 3.92 (s, 3H), 4.13 (dt, J=1.4, J=5.2, 2H), 5.23 (dq, J=1.2, J=10.6, 1H), 5.34 (dq, J=1.4, J=18.0, 1H), 5.89-6.08 (m, 1H), 6.38 (s, 3H), 6.46 (d, J=12.2, 1H), 6.59 (d, J=12.2, 1H), 6.91 (d, J=8.8, 1H), 7.40 (dd, J=2.2, J=8.8 1H), 7.75 (d, J=2.2, 1H).

(Z)-{3-Methoxy-5-[2-(4-methoxy-3-nitro-phenyl)-vinyl]-phenoxy}-acetic acid ethyl ester (8f)

$^1$H NMR (CDCl$_3$): δ 1.23 (t, J=7.2, 3H), 3.69 (s, 3H), 3.93 (s, 3H), 4.21 (t, J=7.2, 2H), 4.49 (s, 2H), 6.33-6.35 (m, 1H), 6.39 (t, J=2.2, 1H), 6.40-6.42 (m, 1H), 6.46 (d, J=12.4, 1H), 6.59 (d, J=12.4, 1H), 6.91 (d, J=8.8, 1H), 7.06 (dd, J=2.2, J=8.8 1H), 7.74 (d, J=2.2, 1H).

(Z)-2-{3-Methoxy-5-[2-(4-methoxy-3-nitro-phenyl)-vinyl]-phenoxy}-ethanol (9a)

$^1$H NMR (CDCl$_3$): δ 2.2 (br, 1H), 3.92 (s, 3H), 3.90-3.93 (m, 5H), 3.95-3.97 (m, 2H), 6.38 (t, J=2.0, 1H), 6.40 (t, J=2.0, 2H), 6.47 (d, J=12.4, 1H), 6.60 (d, J=12.4, 1H), 6.92 (d, J=8.8, 1H) 7.40 (dd, J=2.4, J=8.8, 1H), 7.76 (d, J=2.4, 1H).

(Z)-3-Methoxy-5-[2-(4-methoxy-3-nitro-phenyl)-vinyl]-phenol (9d)

$^1$H NMR (CDCl$_3$): δ 3.69 (s, 3H), 3.92 (s, 3H), 4.95 (br, 1H), 6.28-6.31 (m, 2H), 6.35-6.37 (m, 1H), 6.45 (d, J=12.2, 1H), 6.57 (d, J=12.2, 1H), 6.91 (d, J=8.8, 1H), 7.40 (dd, J=2.2, J=8.8, 1H), 7.75 (d, J=2.2, 1H).

(Z)-{3-Methoxy-5-[2-(4-methoxy-3-nitro-phenyl)-vinyl]-phenoxy}-acetic acid (9f)

$^1$H NMR (CDCl$_3$): δ 3.71 (s, 3H), 3.93 (s, 3H), 4.54 (s, 2H), 6.29-6.31 (m, 1H), 6.40 (t, J=2.2, 1H), 6.44 (s, 1H), 6.48 (d, J=12.0, 1H), 6.69 (d, J=12.0, 1H), 6.94 (d, J=8.8, 1H), 7.37 (dd, J=2.6, J=8.8 1H), 7.71 (d, J=2.6, 1H), 11.45 (br, 1H).

(E)-{3-Methoxy-5-[2-(4-methoxy-3-nitro-phenyl)-vinyl]-phenoxy}-acetic acid (9f trans)

$^1$H NMR (DMSO): δ 3.77 (s, 3H), 3.96 (s, 3H), 4.70 (s, 2H), 6.40-6.42 (m, 1H), 6.76-6.80 (m, 2H), 7.20 (d, J=16.2, 1H), 7.32 (d, J=16.2, 1H), 7.40 (d, J=8.0, 1H), 7.89 (d, J=2.2, J=8.0, 1H), 7.11 (d, J=2.6, 1H), 11.71 (br, 1H).

(E)-5-[2-(3-Ethoxy-5-methoxy-phenyl)-vinyl]-2-methoxy-phenylamine, hydrochloride (10b trans)

M.p 147-149° C. $^1$H NMR (CD$_3$OD): δ 1.40 (t, J=7.2 3H), 3.81 (s, 3H), 4.0 (s, 3H), 4.05 (q, J=7.2, 2H), 6.40 (d, J=2.0, 1H), 6.68-6.69 (m, 2H), 7.02 (d, J=16.4, 1H), 7.11 (d, J=16.4, 1H), 7.20 (d, J=8.4, 1H), 7.51 (d, J=2.4, 1H), 7.60 (dd, J=2.4, J=8.8 1H). $^{13}$C NMR: δ 15.2, 55.7, 56.9, 64.6, 101.5, 105.4, 106.2, 113.6, 122.3, 127.9, 129.6, 129.9, 132.5, 140.4, 153.5, 161.8, 162.5.

(E)-5-[2-(3-Isopropoxy-5-methoxy-phenyl)-vinyl]-2-methoxy-phenylamine, hydrochloride (10c trans)

M.p. 134-136° C. $^1$H NMR (CD$_3$OD): δ 1.32 (d, J=6.0, 6H), 3.80 (s, 3H), 4.0 (s, 3H), 4.56-4.69 (m, 1H), 6.39 (t, J=2.2 1H), 6.66-6.68 (m, 2H), 6.99 (d, J=16.2, 1H), 7.11 (d, J=16.2, 1H), 7.20 (d, J=8.6, 1H), 7.51 (d, J=2.0, 1H), 7.61 (dd, J=2.0, J=8.6 1H).
$^{13}$C NMR: δ 22.4, 55.8, 56.9, 71.0, 102.8, 105.4, 107.8, 113.5, 122.1, 127.9, 129.9, 152.1, 159.7, 162.1

(E)-5-[2-(3-Allyloxy-5-methoxy-phenyl)-vinyl]-2-methoxy-phenylamine, hydrochloride (10e trans)

M.p. 137-140° C. $^1$H NMR (CD$_3$OD): δ 3.80 (s, 3H), 4.0 (s, 3H), 4.56 (dt, J=1.4, J=5.2, 2H), 5.25 (dq, J=1.4, J=10.4, 1H), 5.41 (dq, J=1.4, J=17.4, 1H), 5.98-6.17 (m, 1H), 6.43 (t, J=2.2, 1H), 6.71 (d, J=2.2, 1H), 7.01 (d, J=16.2, 1H), 7.13 (d, J=16.2, 1H), 7.21 (d, J=8.6, 1H), 7.54 (d, J=8.6, 1H), 7.64 (dd, J=2.2, J=8.6 1H).

Scheme 3.

In FIG. 1c, Scheme 3 shows the synthesis of compounds in which one of the phenyl rings in the stilbene backbone is replaced by an heterocyclic moiety. The suitable heterocyclic aldehyde 11a-c is reacted with a benzyl triphenyl phosphonium bromide 1 or 7 as described in schemes 1 and 2 (step i, as described in step i, scheme 1). After separation from E isomers, the Z stilbenes may be then methylated at heterocyclic nitrogen with methyl iodide and potassium hydroxide in dimethylsulfoxide solution (step ii). Methylation at benzimidazole nitrogen gives two regioisomers that are not separated, whose mixture is named as 13c. Nitro compounds 12d and 13d are then reduced and salified to 14a,b with zinc in acetic acid (steps iii and iv, as described in steps ii and vii, scheme 1).

Example 10

Scheme 3, Step ii

(Z)-5-[2-(3,5-Dimethoxy-phenyl)-vinyl]-1-methyl-1H-indole (13a)

A suspension of KOH (2 mmol, 112 mg) in DMSO (5 mL) is stirred for 5 min. Then, compound 12a (1 mmol, 279 mg) and iodomethane (1.2 mmol, 75 μL) are added to the solution. The mixture is stirred at room temperature for 30 min, poured into water/ice, and extracted with ethyl acetate. The combined organic extracts are washed with brine (5 mL) and dried (Na$_2$SO$_4$). Removal of the solvent under reduced pressure affords a residue, which is chromatographed on silica gel (20% ethyl acetate/light petroleum).

Oil, 274 mg. Yield 93%. $^1$H NMR (CDCl$_3$): δ 3.63 (s, 6H), 3.76 (s, 3H), 6.32 (t, J=2.2, 1H), 6.40-643 (m, 2H), 6.46-6.52 (m, 2H), 7.73 (d, J=12.2, 1H), 7.0 (d, J=2.2, 1H), 7.17-7.19 (m, 2H), 7.58-7.59 (m, 1H).
$^{13}$C NMR: δ 33.0, 55.4, 99.7, 101.3, 104.7, 106.7, 108.8, 121.7, 123.0, 127.8, 129.1, 132.0, 139.9, 160.5.
Anal. (C$_{19}$H$_{19}$NO$_2$) C, H, N.

From procedures described in scheme 3 the following new compounds have been obtained:

(Z)-5-[2-(3,5-Dimethoxy-phenyl)-vinyl]-1H-indole (12a)

$^1$H NMR (CDCl$_3$): δ 3.61 (s, 6H), 6.31 (t, J=2.2, 1H), 6.43-6.49 (m, 3H), 6.73 (d, J=12.2, 1H), 7.13-7.21 (m, 3H), 8.10 (br, 1H).
$^{13}$C NMR: δ 55.2, 99.7, 102.9, 106.8, 110.6, 121.5, 123.5, 124.5, 127.7, 128.0, 128.8, 132.0, 139.8, 160.5.
Anal. (C$_{18}$H$_{17}$NO$_2$) C, H, N.

(Z)-6-[2-(3,5-Dimethoxy-phenyl)-vinyl]-1H-indole (12b)

$^1$H NMR (CDCl$_3$): δ 3.61 (s, 6H), 6.31 (t, J=2.4, 1H), 6.47-6.51 (m, 4H), 6.72 (d, J=12.4, 1H), 7.08 (dd, J=1.6, J=8.0 1H), 7.17-7.18 (m, 1H), 7.32 (s, 1H), 7.49 (d, J=8.0 1H), 8.05 (br, 1H).
$^{13}$C NMR: δ 55.3, 99.8, 102.7, 106.8, 111.4, 120.3, 121.6, 124.9, 127.3, 128.7, 131.8, 139.9, 160.6.
Anal. (C$_{18}$H$_{17}$NO$_2$) C, H, N.

(Z)-5-[2-(3,5-Dimethoxy-phenyl)-vinyl]-1H-benzoimidazole (12c)

$^1$H NMR (CDCl$_3$): δ 3.04 (br, 1H), 3.61 (s, 6H), 6.31 (t, J=2.2, 1H), 6.41 (d, J=2.2, 2H), 6.54 (d, J=12.2, 1H), 6.73 (d, J=12.2, 1H), 7.25-7.29 (m, 1H), 7.53-7.56 (m, 2H), 8.20 (s, 1H).
Anal. (C$_{17}$H$_{16}$N$_2$O$_2$) C, H, N.

(Z)-6-[2-(3,5-Dimethoxy-phenyl)-vinyl]-1-methyl-1H-indole (13b)

$^1$H NMR (CDCl$_3$): δ 3.62 (s, 6H), 3.68 (s, 3H), 6.33 (t, J=2.2, 1H), 6.41 (d, J=3.2, 1H), 6.45 (d, J=3.2, 1H), 6.50-6.54 (m, 3H), 6.74 (d, J=12.0, 1H), 7.02 (d, J=3.2, 1H), 7.09 (d, J=8.4, 1H), 7.46 (d, J=8.4, 1H).
$^{13}$C NMR: δ 32.7, 55.3, 99.8, 100.0, 101.0, 106.8, 109.8, 120.3, 121.0, 128.6, 129.5, 131.9, 139.9, 160.6.
Anal. (C$_{19}$H$_{19}$NO$_2$) C, H, N.

(Z)-5-[2-(3,5-Dimethoxy-phenyl)-vinyl]-1-methyl-1H-benzoimidazole (13ca)

and

(Z)-6-[2-(3,5-Dimethoxy-phenyl)-vinyl]-1-methyl-1H-benzoimidazole (13cb)

are obtained as unseparable mixture from 12c methylation (step iii, scheme 3). Spectroscopic data are consistent with the mixture of the two regioisomers.

(Z)-5-[2-(1H-Indol-5-yl)-vinyl]-2-methoxy-phenylamine, oxalate salt (14a)

Recrystalized methanol/diethyl ether. M.p. 112-115° C. $^1$H NMR (CD$_3$OD): δ 3.91 (s, 3H), 6.32 (dd, J=1.0, J=2.2, 1H), 6.41 (d, J=12.2, 1H), 6.60 (s, 1H), 6.61 (d, J=12.2, 1H), 6.96-7.02 (m, 3H), 7.15-7.16 (m, 1H), 7.18-7.21 (m, 1H), 7.23-7.25 (m, 1H), 7.44 (s, 1H).
Anal. (C$_{19}$H$_{18}$N$_2$O$_5$) C, H, N.

(Z)-2-Methoxy-5-[2-(1-methyl-1H-indol-5-yl)-vinyl]-phenylamine (14b)

$^1$H NMR (CDCl$_3$): δ 3.76 (s, 3H), 3.82 (s, 3H), 6.40 (d, J=12.2, 1H), 6.41 (d, J=3.2, 1H), 6.61 (d, J=12.2, 1H), 6.65-6.67 (m, 2H), 6.71 (m, 1H), 7.00 (d, J=3.2, 1H), 7.17 (m, 2H), 7.57 (s, 1H).
Anal. (C$_{18}$H$_{18}$N$_2$O) C, H, N.

Other compounds obtained from Scheme 3.

(Z)-2-Methoxy-5-[2-(1-methyl-1H-indol-5-yl)-vinyl]-phenylamine (13d)

$^1$H NMR (CDCl$_3$): δ 3.77 (s, 3H), 3.90 (s, 3H), 6.37-6.46 (m, 2H), 6.79 (d, J=12.4, 1H), 6.85 (d, J=8.8, 1H), 7.03 (d, J=3.2, 1H), 7.10 (d, J=1.4, 1H), 7.16 (s, 1H), 7.42 (dd, J=2.2, J=8.8, 1H), 7.50 (s, 1H), 7.8 (d, J=2.2, 1H).

(E)-2-Methoxy-5-[2-(1-methyl-1H-indol-5-yl)-vinyl]-phenylamine (13d trans)

$^1$H NMR (CDCl$_3$): δ 3.77 (s, 3H), 3.82 (s, 3H), 6.38 (d, J=3.2, 1H), 6.39 (d, J=12.2, 1H), 6.64-6.68 (m, 3H), 7.0 (d, J=1.4, 1H), 7.17-7.19 (m, 2H), 7.57 (s, 1H).

Example 11

Disruption of Tubulin Polymerization by Stilbenes

Methods
The tubulin polymerization assay kit was purchased from Cytoskeleton (Denver, Colo.). Tubulin (>99% pure) was mixed with general tubulin buffer (GTB, 80 mM PIPES pH 6.9, 2 mM MgCl$_2$, 0.5 mM EGTA, and 1 mM GTP) in a 96-well plate at 37° C. Absorbance at 340 nm was measured every 1 min for 60 min by SpectraMAX 250 (Molecular Devices, Sunnyville, Calif.). Analysis of the results was performed by SoftMAX Pro version 1.2.0 from the same company.

To test whether stilbenes interact with tubulin at the colchicine site, tubulin was incubated with [$^3$H]-colchicine along with various concentrations of non-radioactive colchicine or stilbenes in the GTB buffer at 37° C. for 20 min. The mixtures were loaded into Microcon-YM30 and centrifuged at 12,500 rpm to separate the unbound [$^3$H]-colchicine. Tubulin retained in the Microcon was washed three times with PBS. The radioactivity of the final concentrated tubulin was determined by a scintillation counter.

Computational Docking of Stilbenes to Tubulin
We characterized the binding site by docking and scoring of the stilbene 4a and 4c analogues in what is termed the colchicine-binding cavity of the tubulin dimer, thereby describing the strong ligand-binding features at the active site. The X-ray crystal structure of αβ-tubulin complexed with DAMA-colchicine (PDB code ISA0 [34]) was the starting point. Both α and β subunits were retained, while the stathmin-like domain and the C and D subunits were removed. Hydrogen atoms were added and optimized, i.e., all protein side-chain and backbone atoms were kept fixed, using the Tripos force field, as incorporated in Sybyl 7.1 with 10000 steps of Fletcher-Powell optimization until an energy gradient of 0.005 kcal-Å/mol was reached. The binding models for stilbenes 4a and 4c were constructed using the model of CA4 [35] as a template and reference ligand in the binding site. Computational docking was carried out using GOLD 3.0 [36]. Docking models highly ranked by the Goldscore function were selected for characterizing the binding site. With this procedure stilbenes 4a and 4c apparently bind in the same mode as combretastatin at the colchicine binding site.

Results

Figure 3A:
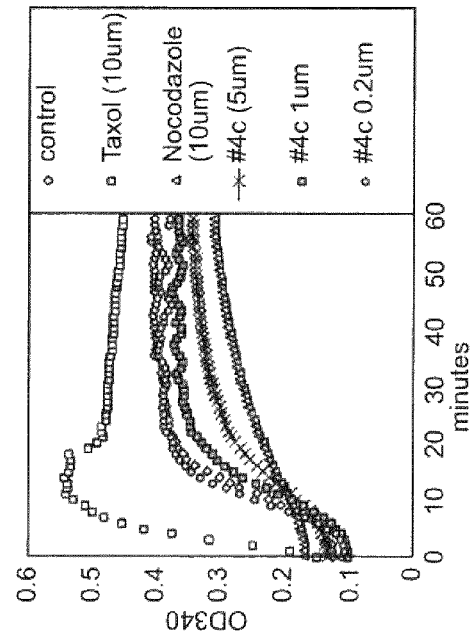
FIG. 3a-d. Stilbenes inhibit tubulin polymerization. (a) Effect of stilbene 4a. Pure tubulin was incubated with various concentrations of stilbene 4a, 10 μM nocodazole, and 10 μM paclitaxel in the polymerization buffer. The OD at 340 nm was monitored every minute by SpectraMAX 250 and plotted against time. (b) Effect of stilbene 4c. (c) Comparison of same concentrations of stilbenes 4a, 4a trans, 4c and 4c trans with control. (d) Stilbene 4a competes with colchicine in binding tubulin. Tubulin was incubated with [$^3$H]-colchicine and various concentrations of different stilbenes for 20 min. Tubulin was then separated from the unbound [$^3$H]-colchicine by Microcon-30 and washed three times with PBS. The radioactivity of the tubulin was counted. The activity of the tubulin without competing colchicines or stilbenes was counted as 100% for evaluation of the competition between colchicine and stilbenes. All experiments were done in triplicates.
Figure 3B:
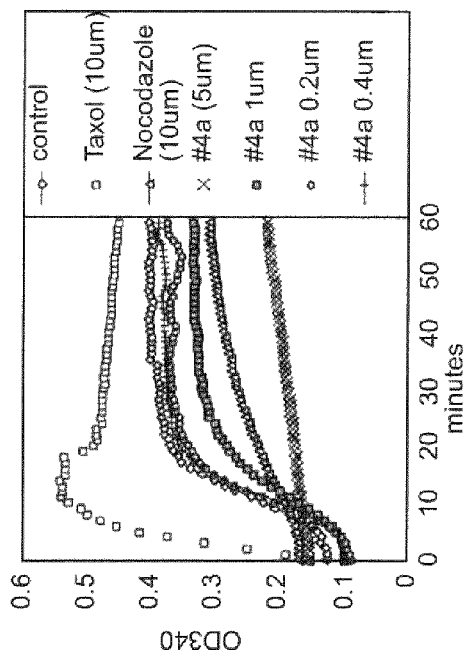
Figure 3C:
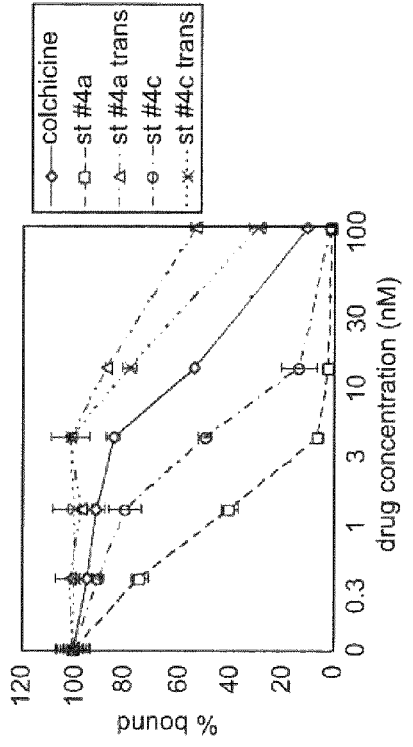

Stilbenes 4a and 4c Interfere with Polymerization of Tubulin
Because microtubule is a complexed structure composed of α, β tubulin and other microtubule-associated proteins (MAPs), we investigated whether stilbenes 4a and 4c directly interfered with tubulin polymerization. Tubulin with more than 99% purity was used for this study in order to eliminate the contribution from MAPs. Polymerization was monitored by OD340 nm. As controls for polymerization, paclitaxel enhanced, whereas nocodazole suppressed, polymerization. Stilbene 4a suppressed polymerization in a dose-dependent manner (FIG. 3a). Stilbene 4c also suppressed tubulin polymerization in a dose-dependent manner but less potent than stilbene 4a (FIG. 3b). The trans-stilbenes 4a trans and 4c trans could not suppress tubulin polymerization as expected (FIG. 3c).

Figure 3D:
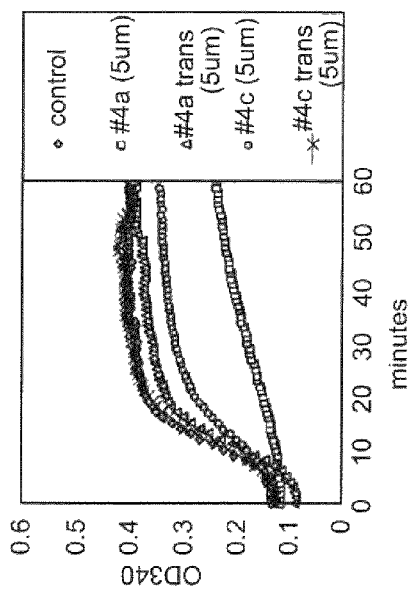

Stilbenes 4a and 4c Compete with Colchicine to Bind Tubulin.
There are three sites in tubulin molecules that bind microtubule-interfering agents. Taxanes bind on the surface of microtubules. Colchicine binds on the interface between α and β subunits of tubulin within the heterodimer, whereas vinca alkaloids bind at the interface between heterodimers. To identify the binding site of tubulin that interacts with stilbenes, we used [$^3$H]-colchicine for a competition study and tested whether stilbenes can compete with colchicine to interact with tubulin. When the radioactive colchicine was incubated with various concentrations of stilbenes 4a and 4c, there was a dose-dependent suppression of tubulin-colchicine interaction by stilbenes, indicating that stilbenes and colchicine may bind at the same site of tubulin to disrupt tubulin polymerization (FIG. 3d). Stilbene 4a is more potent than stilbene 4c, and the trans-stilbenes 4a trans and 4c trans are much weaker than colchicine.

Figure 4A:
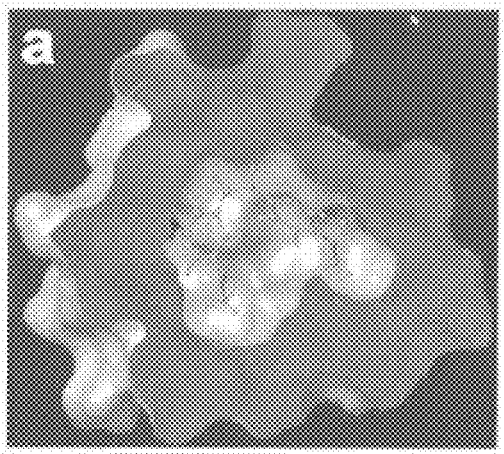
FIG. 4a-c. Structural modeling of stilbene and tubulin. (a) Computational docking of stilbene 4a into colchicine site of tubulin. (b) Overlaying of the docking of stilbene 4a and CA-4 into the colchicine-binding pocket of tubulin. The α-tubulin is at right and the β-tubulin is at left. The carbons of stilbene 4a are shown in dark gray and those of combretastatin A-4 are in light gray. (c) Ball and stick model of stilbene 4a and the surrounding tubulin. The hydrogen bond formed by the amino group of stilbene 4a and Val-181 of α-tubulin is shown in dash.
Figure 4B:
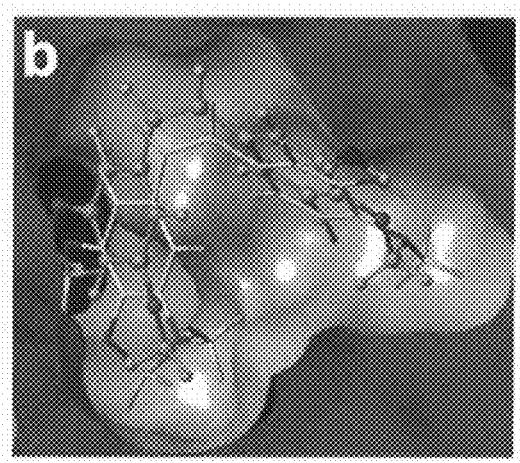
Figure 4C:
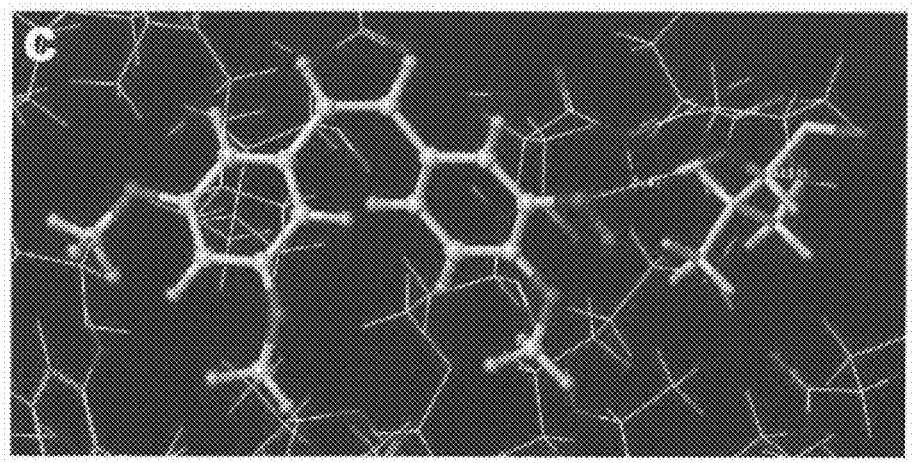
Figure 5A:
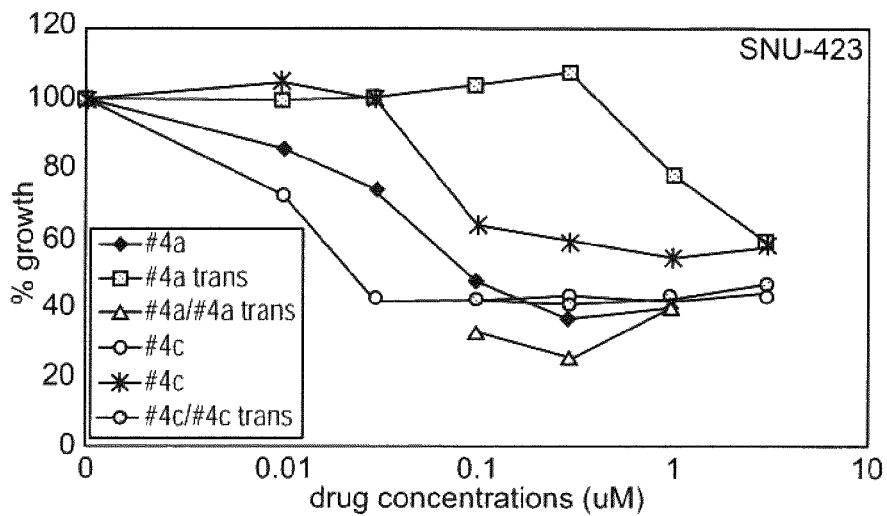
FIGS. 5a-e shows the potency of the representative stilbene derivatives in suppressing tumor cell growth in SNU-423 hepatocellular carcinoma cells. Cells were incubated with the indicated concentrations of the compounds listed in FIG. 2 for 48 hours. Other compounds including the trans derivative of compounds 4a and 4c (4a trans and 4c trans) and standard chemotherapeutic agents, vincristine, doxorubicin, and existing microtubule-interfering agents colchicine and combretastatin A-4 were also compared. Cell growth was measured by Alamar Blue™ staining and the OD absorbance at 570 and 600 nm was determined by a microplate reader [16]. The percentage of cell growth inhibition was calculated and compared with the control cells that were treated with 0.1% DMSO, the vehicle for the stilbene compounds.
Figure 5B:
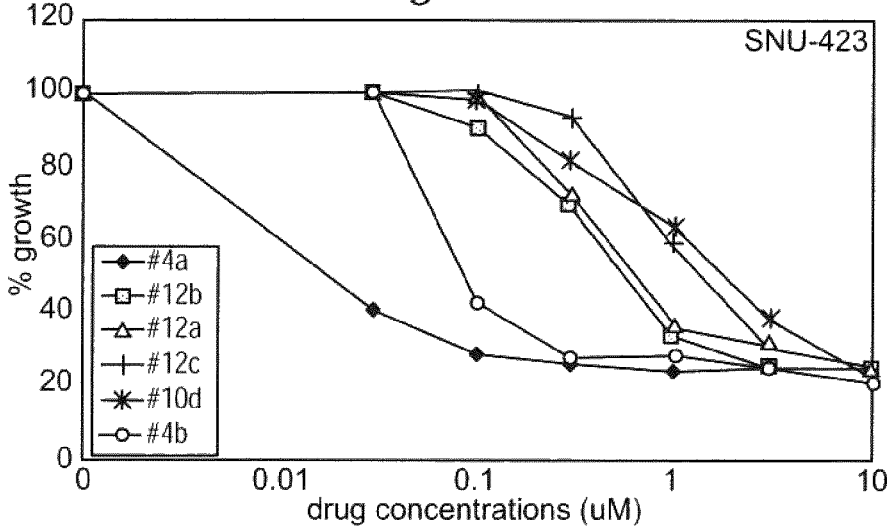
Figure 5C:
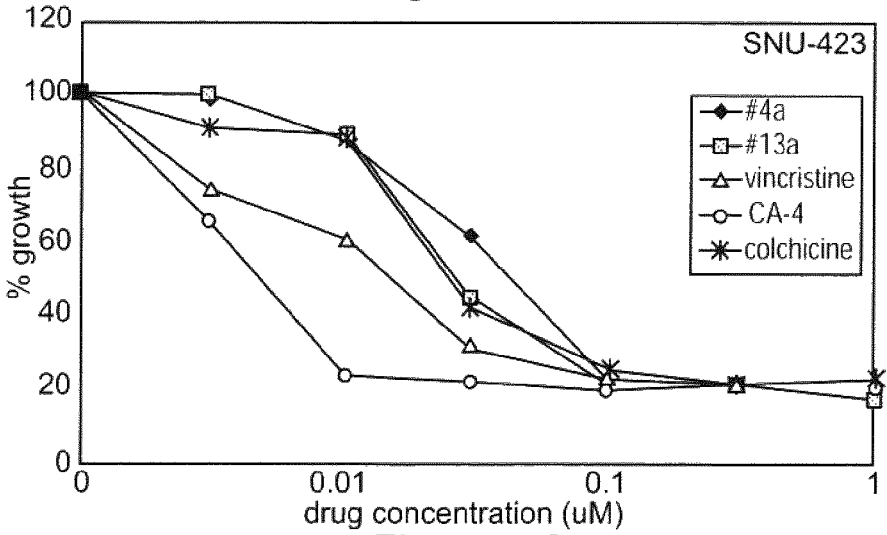
Figure 5D:
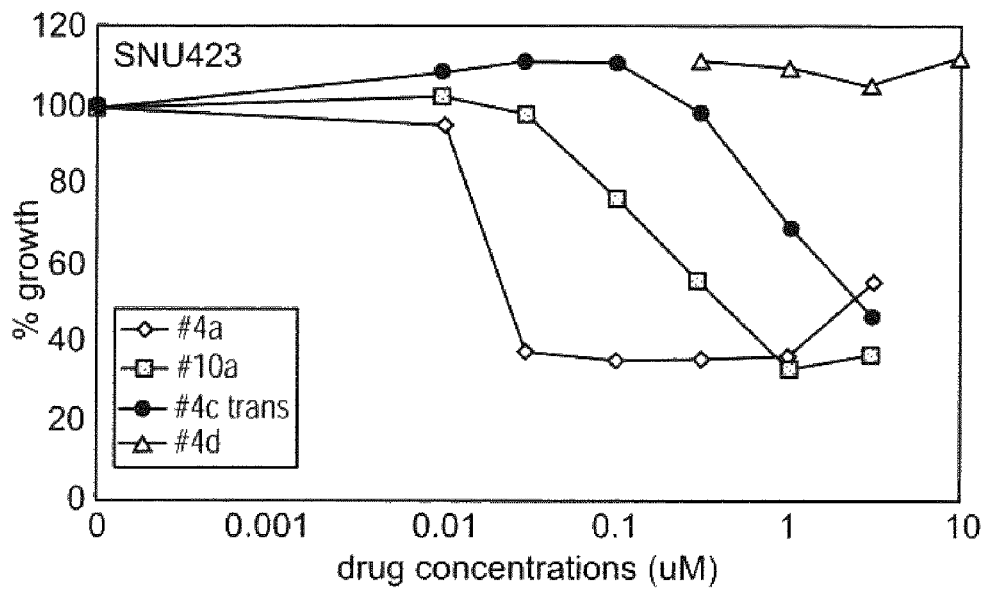
Figure 5E:
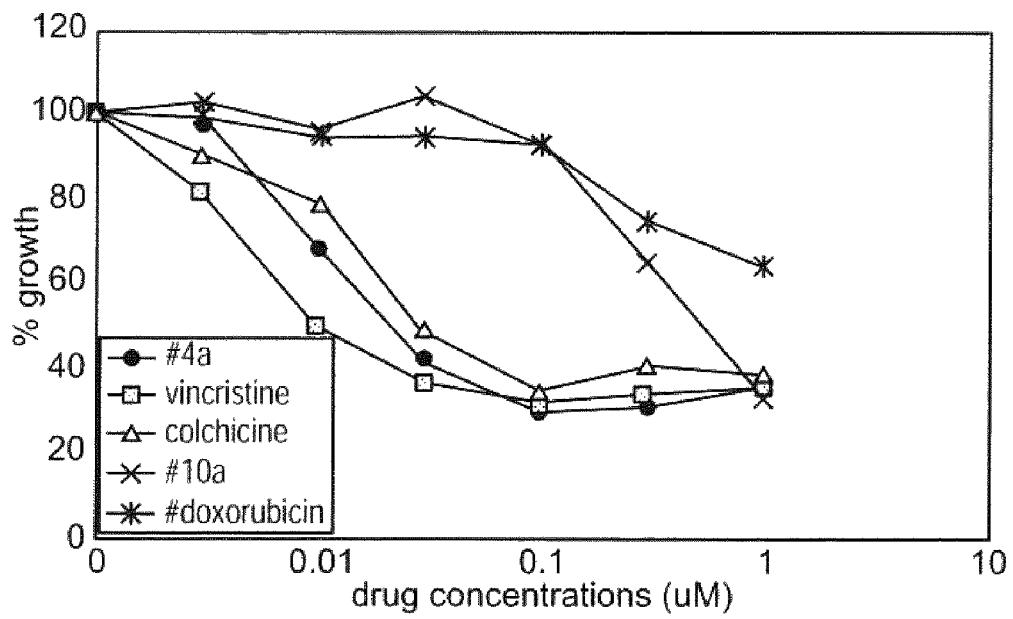

Docking of Stilbenes into Colchicine Binding Pocket of Tubulin
Since the structure of tubulin complexed with colchicine is solved [34], we performed computational docking of stilbenes into tubulin structure to confirm that stilbenes can fit into the colchicine-binding pocket of tubulin (FIG. 4a). Combretastatin-A4 (CA4), another colchicine site inhibitor, was used for comparison. Stilbene 4c, which differs from CA4 by lacking the 4-methoxyl group, overlaps perfectly with CA4. In contrast, stilbene 4a, due to the 3'-amino group instead of the hydroxyl group in stilbene 4c, shifts by about 1 Å closer to the β-tubulin (FIG. 4b). A hydrogen bond can be formed between the nitrogen of the amino group and Val181 of the neighboring α-tubulin (FIG. 4c). This docking study thus confirms that stilbenes can bind the colchicine site of tubulin, and the 4-methoxyl group of colchicine and CA4 is not essential for tubulin interaction.

Example 12

Anti-Tumor Activity of Stilbene Derivatives

Methods

Various cancer cell lines were grown in 96-well plates for drug sensitivity assays. Once cells achieved 50% confluence, the incubation media was changed to the same cell growth media with different concentrations of the tested compounds or vehicle alone. Cells were then incubated for 48 hours before the cell growth inhibition study. To determine the degree of cell growth inhibition, 1/10 volume of Alamar Blue™ solution was added to each well and optical density (OD) at 570 and 600 nm was determined. The percentage of growth inhibition was calculated according to the manufacturer's formula as follows: The percentage of growth is $[(117216 \times A_{570}) - (80586 \times A_{600})]/[(117216 \times A^{o}_{570}) - (80586 \times A^{o}_{600})] \times 100$. In this formula, $A_{570}$ is the absorbance of the treated samples at 570 nm; $A_{600}$ is the absorbance of the treated samples at 600 nm; $A^{o}_{570}$ is the absorbance of the treated samples at 570 nm; and $A^{o}_{600}$ is the absorbance of the untreated samples at 600 nm. The two constants, 117216 and 80586, are the extinction coefficients of Alamar Blue™ at 570 and 600 nm respectively. Each concentration was repeated in triplicate to minimize the error.

In order to establish that stilbene suppresses tumor perfusion by damaging tumor endothelial cells, we first incubated human vascular endothelial cells with various concentrations of stilbenes in vitro. After 24 hours of incubation, cells were then fixed with 2% paraformaldehyde and stained with anti-tubulin antibody to examine the tubulin disruption and with DAPI to analyze nuclear fragmentation. Dynamic-contrast enhanced magnetic resonance imaging (MRI) scanning was used to investigate tumor perfusion in vivo. Immunodeficient nude mice were first injected with Hep3B hepatocellular carcinoma cells subcutaneously. When the tumor reached a diameter of 0.8 cm in diameter, mice were treated with stilbene 4a at 50 mg/kg or vehicle (DMSO) intraperitoneally for 16 hours. Before the MRI scan, an intravenous catheter was placed in the neck jugular vein for injection of the contrast medium. A regular sequence MRI was performed first for visualization of the tumor before injection of the contrast medium. Gadolinium (OmniScan) 0.1 cc (including the dead space of flushing the IV catheter) was injected through the IV catheter for the DCE-MRI study. Images were obtained every second for a minimal of 2 minutes. A region of interest (ROI) was chosen from the scan and the MRI signal in the ROI was plotted against time and the initial steepest slope of the curve was calculated to represent the maximal perfusion of the ROI. A separate ROI was chosen in the normal muscle to be used as an internal control for the mouse. The perfusion rate of the muscle region was normalized and set at 100% and the rate of perfusion in tumor was calculated versus the muscle.

In vitro Efficacy of Stilbenes Derivatives and Comparison with Existing Conventional Chemotherapeutic Agents.

We first tested the cytotoxic effect of various stilbene derivatives for their in vitro efficacy of suppressing tumor cell proliferation. Cells were first plated in 96-well plates at 50% confluence and treated with 0, 0.01, 0.03, 0.1, 0.3, 1.0, 3.0, 10 µM concentrations of stilbene derivatives for 48 hours in triplicate. Alamar Blue™ reagent was added into each well at 1/10 volume and incubated for 2 hours before quantification of the absorbance at 570 and 600 nm. Several well established cytotoxic agents, including colchicine, vincristine, combretastatin A-4 and doxorubicin were included for comparison of their efficacy in cytotoxicity.

First we tested SNU423 hepatocellular carcinoma cells. As shown in FIGS. 5a-e, the cis-stilbenes 4a and 4c are much more potent than the trans counterparts 4a trans and 4c trans. Both stilbenes 4a and 4c are effective in blocking cell proliferation at 0.03-0.1 µM. 10a is less effective than stilbene 4a and 4c and require a concentration up to 0.3 µM to achieve 50% growth inhibition. 4d is not effective even at 10 µM. Other stilbene derivatives 10d and 12a-c are also less effective than stilbenes 4a and 4b with $IC_{50}$ at the range of 0.3-1 µM. Comparing the efficacy of stilbene 4a with existing chemotherapeutic agents such as vincristine, colchicine showed that they are equivalent, but stilbene 4a is more potent than doxorubicin, which has a potency similar to that of 10a. The most potent compound was combretastatin A4 (CA-4), which is effective at 0.003 µM. However, the two most potent stilbenes 4a and 13a were very potent at 0.03 µM.

Figure 6A:
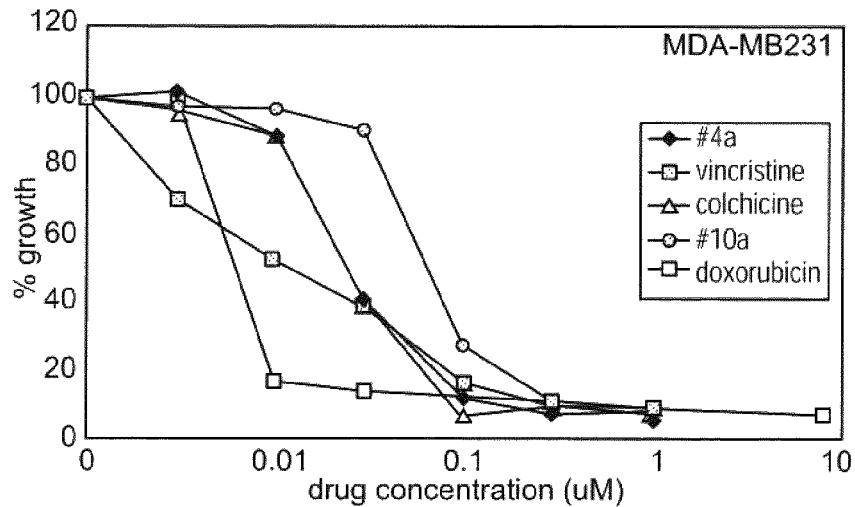
FIGS. 6a-c shows the potency of representative stilbene derivatives in suppressing tumor cell growth in MDA-MB231 breast cancer cells. Cells were incubated with the indicated concentrations of the compounds listed in FIG. 2 for 48 hours. Other compounds including standard chemotherapeutic agents, vincristine, doxorubicin, and existing microtubule-interfering agents colchicine and combretastatin A-4 were also compared. Cell growth was measured by Alamar Blue™ staining and the percentage of cell growth inhibition was calculated and compared with control cells that were treated with 0.1% DMSO, the vehicles for the stilbene compounds.
Figure 6B:
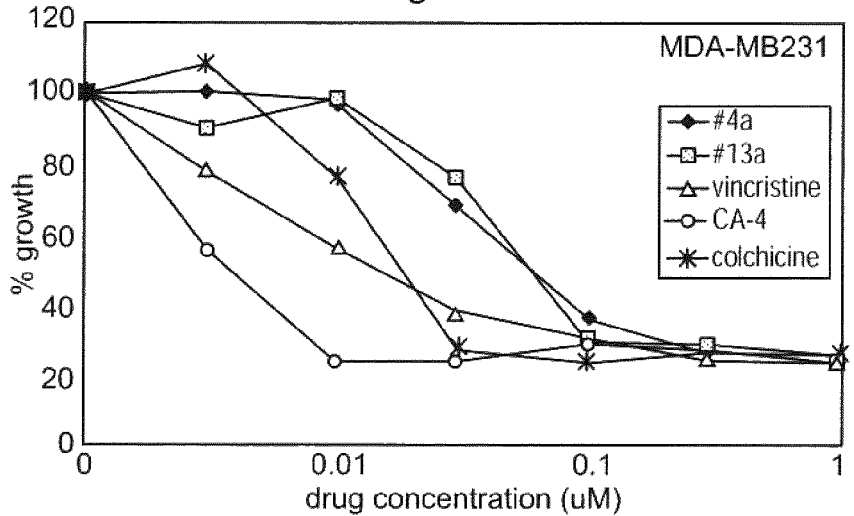
Figure 6C:
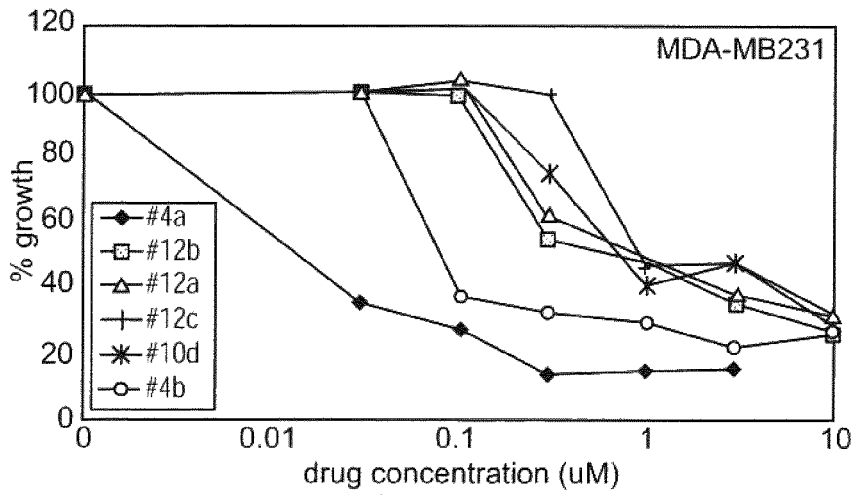
Figure 7A:
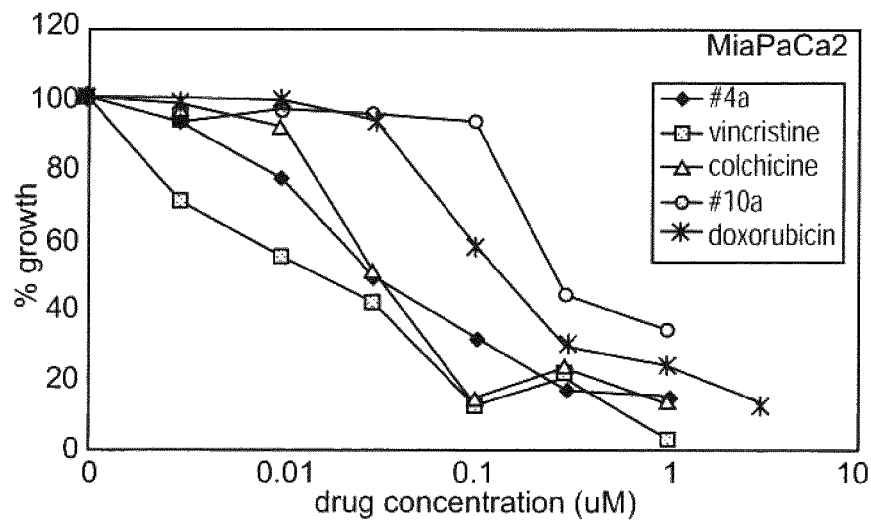
FIG. 7a-c shows the potency of representative stilbene derivatives in suppressing tumor cell growth in UCI101 ovarian cancer cells. Cells were incubated with the indicated concentrations of the compounds listed in FIG. 2 for 48 hours. Other compounds including standard chemotherapeutic agents, vincristine, doxorubicin, and existing microtubule-interfering agents colchicine and combretastatin A-4 were also compared. Cell growth was measured by AlamarBlue™ staining and the percentage of cell growth inhibition was calculated and compared with the control cells that were treated with 0.1% DMSO, the vehicles for the stilbene compounds.
Figure 7B:
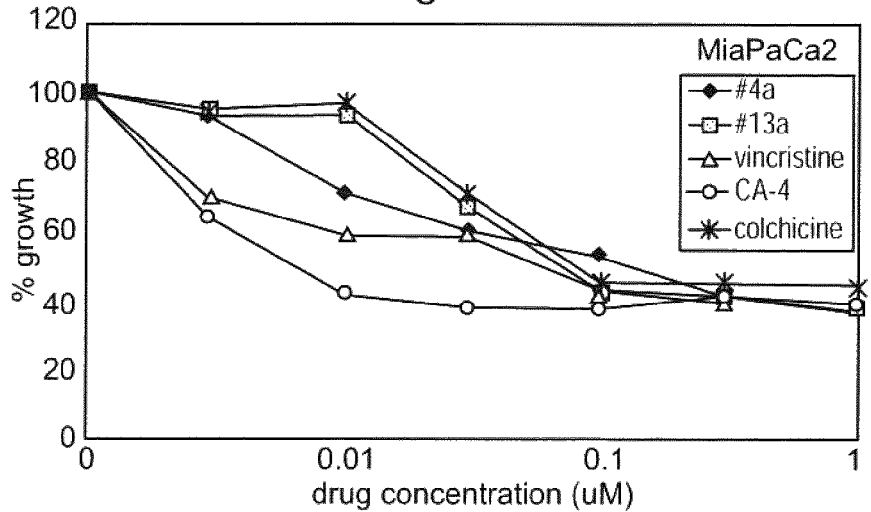
Figure 7C:
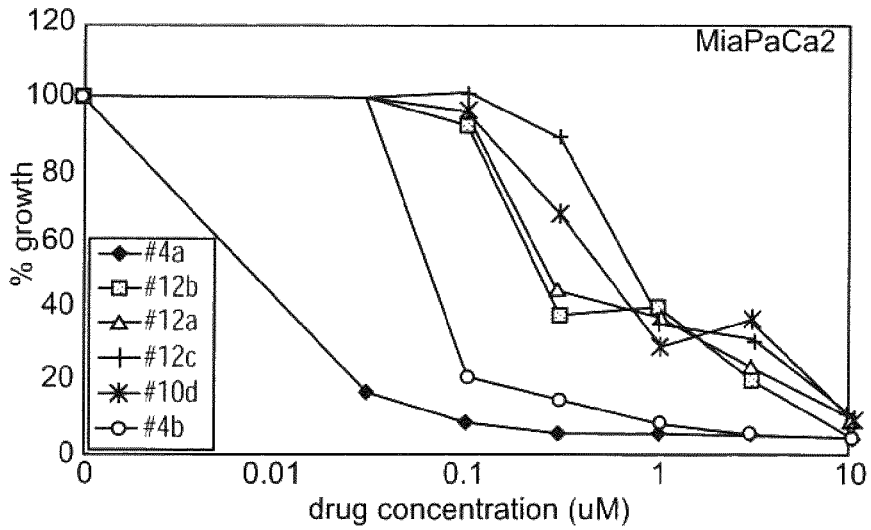

Next we tested breast cancer cells MDA-MB231 (FIGS. 6a-c) and pancreatic cancer cells MiaPaCa2 (FIGS. 7a-c). Basically they follow the same trend as was seen in SNU423 hepatocellular carcinoma cells. CA-4 is still the most effective, and stilbene 4a, 4b and 13a all have potency similar to that of vincristine and colchicine, being effective at concentrations less than 0.1 µM. 10d and 12a-c are effective at concentrations above 0.3 µM.

Figure 8A:
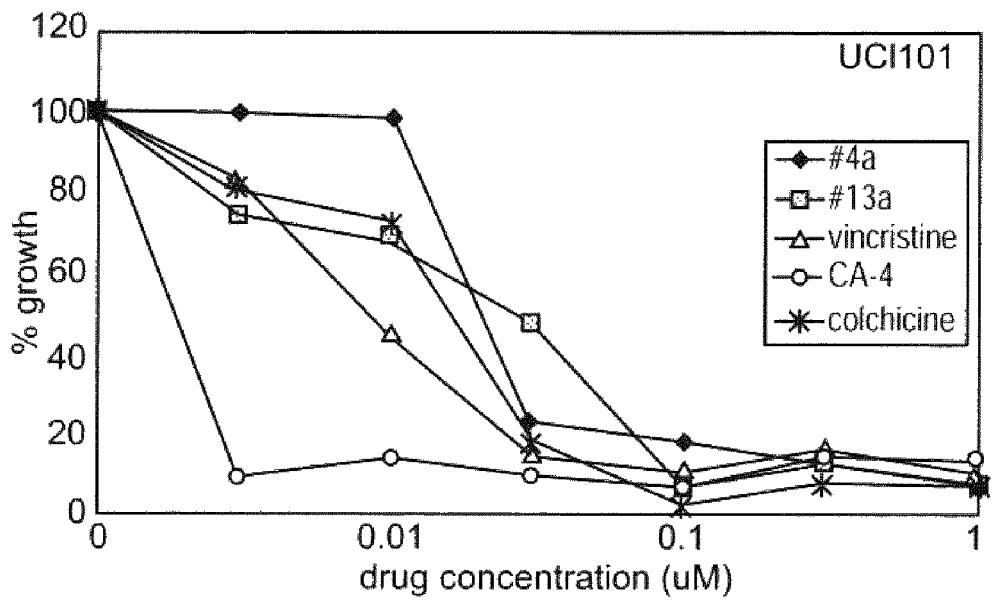
FIG. 8a-b shows the potency of representative stilbene derivatives in suppressing tumor cell growth in UCI101 ovarian cancer cells. Cells were incubated with the indicated concentrations of the compounds listed in FIG. 2 for 48 hours. Other compounds including standard chemotherapeutic agents, vincristine, doxorubicin, and existing microtubule-interfering agents colchicine and combretastatin A-4 were also compared. Cell growth was measured by AlamarBlue™ staining and the percentage of cell growth inhibition was calculated and compared with the control cells that were treated with 0.1% DMSO, the vehicles for the stilbene compounds.
Figure 8B:
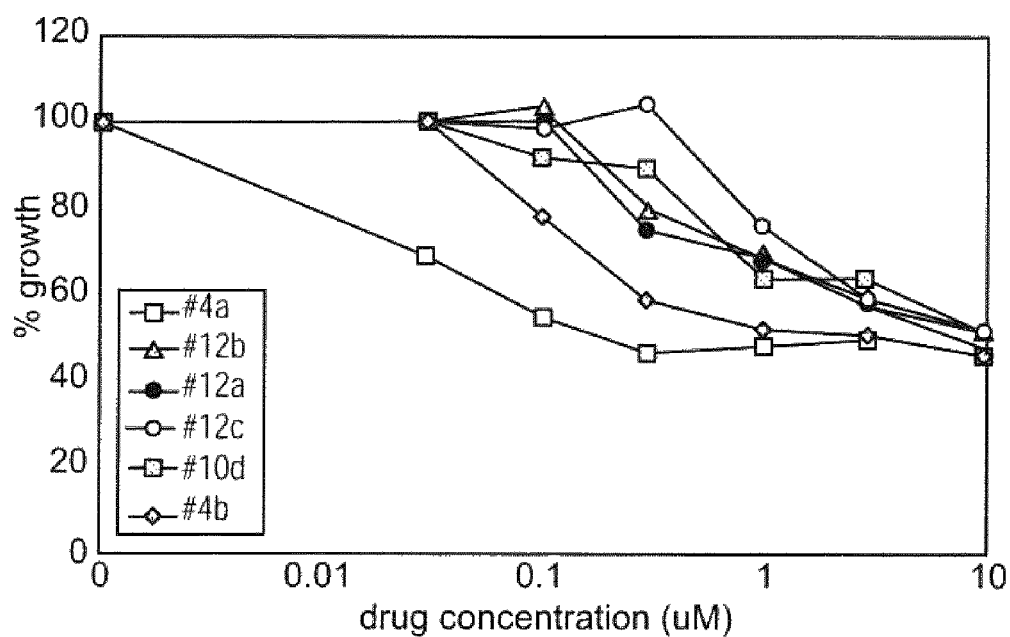
Figure 9A:
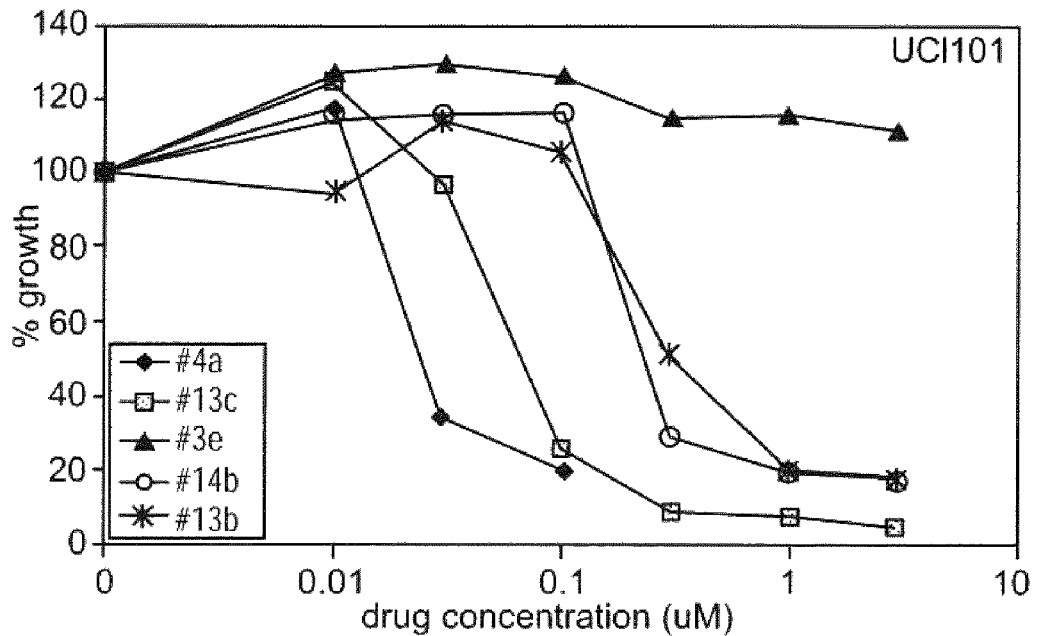
FIG. 9a-b shows the potency of representative stilbene derivatives in suppressing tumor cell growth in UCI-101 ovarian cancer cells. Cells were treated with the tested drug for 2 days before analysis of cell growth by Alamar Blue™ staining. Cells treated with 0.1% DMSO were used as control and set as 100%.
Figure 9B:
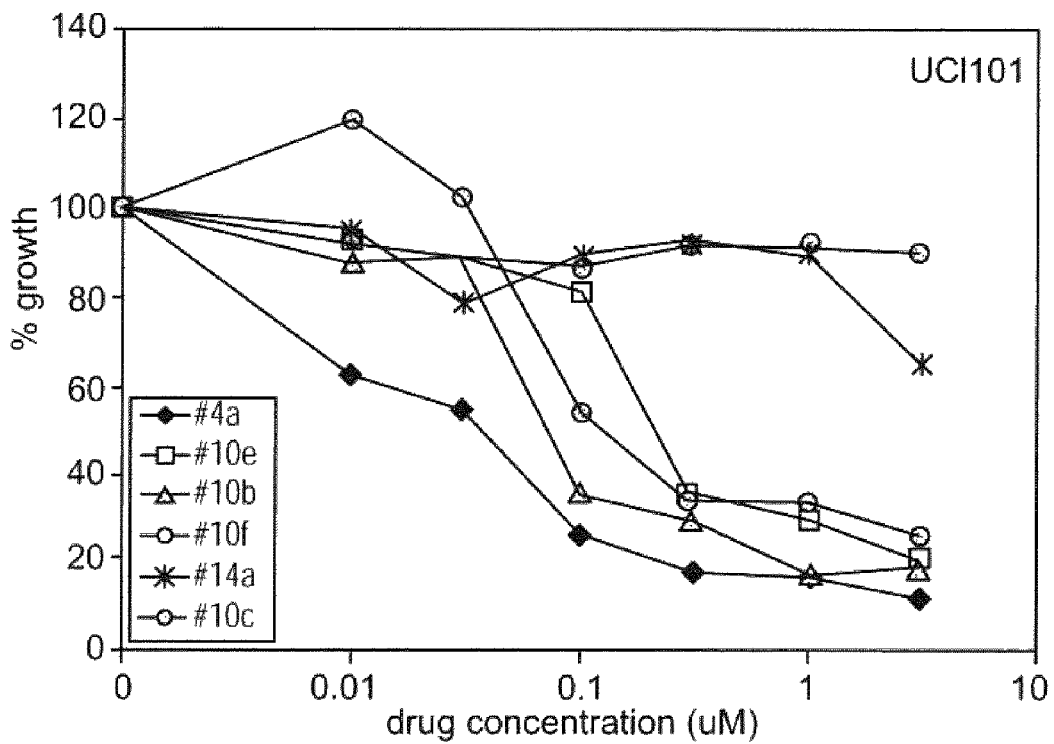
Figure 10A:
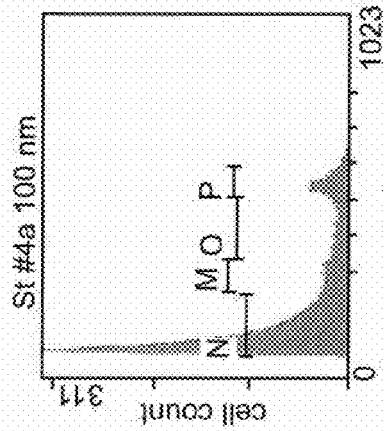
FIG. 10a-f shows the cell cycle analysis of UCI101 cells treated with stilbene 4a at 30 and 100 nM or 5b at 1, 3, 10 μM for 24 hours. Cells were stained with propidium iodide and analyzed with FACScan. Both 5b at 3 μM and stilbene 4a at 30 nM induce a subG0/1 population that represents the dead population. At higher concentrations of either compound, nearly all cells are dead.
Figure 10B:
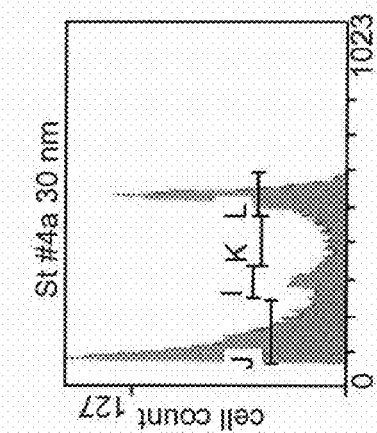
Figure 10C:
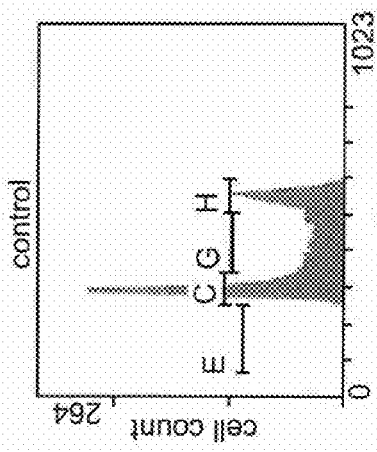
Figure 10D:
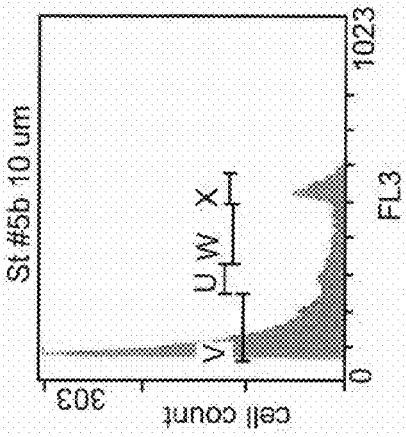
Figure 10E:
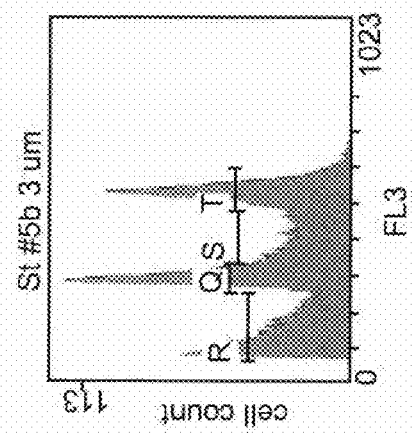
Figure 10F:
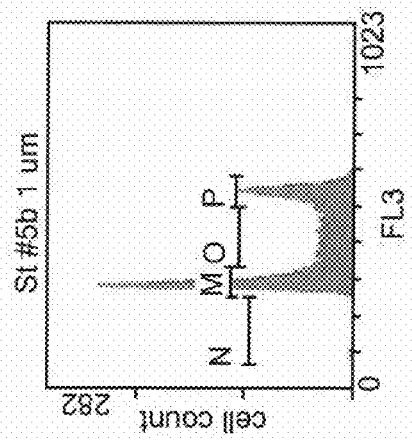

Ovarian cancer UCI101 cells were also tested. FIG. 8a-b shows a comparison among stilbene 4a, 13a, combretastatin A4, colchicine and vincristine. As shown earlier, CA4 is the most active compound and colchicine the second most active. Stilbene 4a, 13a and vincristine are about equal in their potency. Compounds 4b, 10d and 12a-c are less active than stilbene 4a. FIG. 9a-b shows a comparison of stilbene 4a with other compounds. 13c has a potency similar to that of stilbene 4a. 13b,c and 14b were less potent than stilbene 4a by one log, and 3e was not active even up to concentrations of 3 µM. 10b,e were active but less effective than stilbene 4a. 10f and 14a were not active.

Finally, the three potential prodrugs 5a-c were tested and were found to be much less potent. 5a and 5c showed no activity, and 5b was effective only at concentrations of at least 3 µM (FIG. 20a). Based on structural modeling, it should be impossible for 5b to fit into the colchicine binding site of tubulin. Therefore, the most likely mechanism for 5b activity is intracellular conversion into stilbene 4a, the active form.

To confirm that the effect of 5b is mediated by a similar mechanism as stilbene 4a, we performed cell cycle analysis to study whether 5b also blocked cell cycle in G2/M phase similar to stilbene 4a (FIGS. 10a-f). Cells were treated stilbene 4a at 30, 100 nM or 5b at 1, 3, 10 µM. As anticipated, stilbene 4a induced G2/M cell cycle arrest and accumulation of the subG1/0 population that represented cell death population in a dose-dependent manner. 5b, although less potent than stilbene 4a, induced similar cell cycle arrest as stilbene 4a. The effect of 10 µM 5b was equivalent to that of 100 nM of stilbene 4a, indicating that the potency of 5b is 100 fold less than that of stilbene 4a in vitro.

Figure 11:
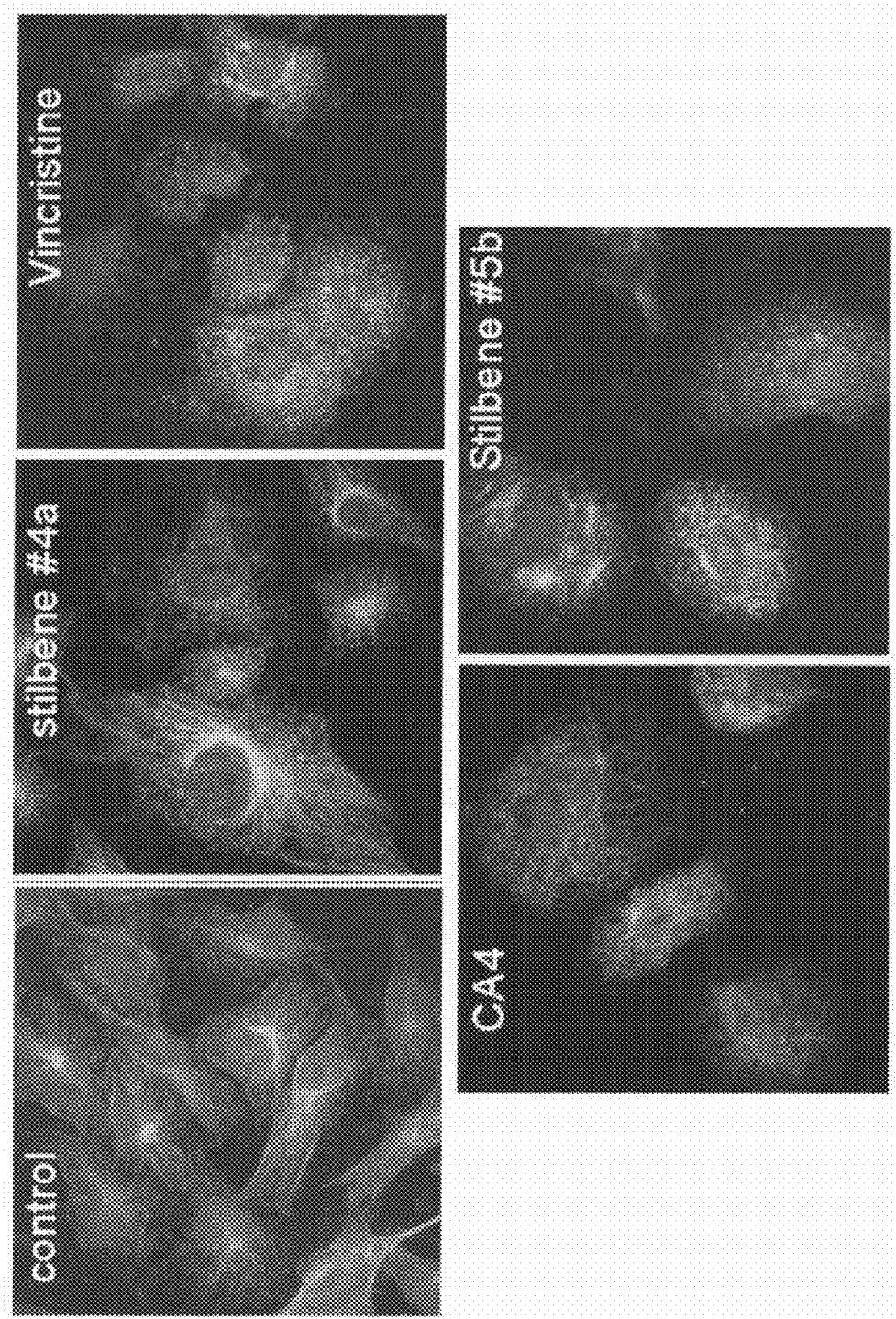
FIG. 11 shows the immunofluorescent staining of tubulin in MDA-MB231 cells treated with combretastatin A4 (CA4) (10 nM), stilbene 4a (100 nM), vincristine (100 nM) or 5b (3 μM) for 16 hours. Nuclei were stained with 4',6-diamidino-2-phenylindole (DAPI). Control cells show the reticular pattern of the microtubule network. Cells treated with other compounds exhibit partial disorganization of microtubules. Interestingly, the left upper 5b treated cell showed multiple microtubule organization centers and the right lower cell showed near complete depolymerization of microtubules.
Figure 12:
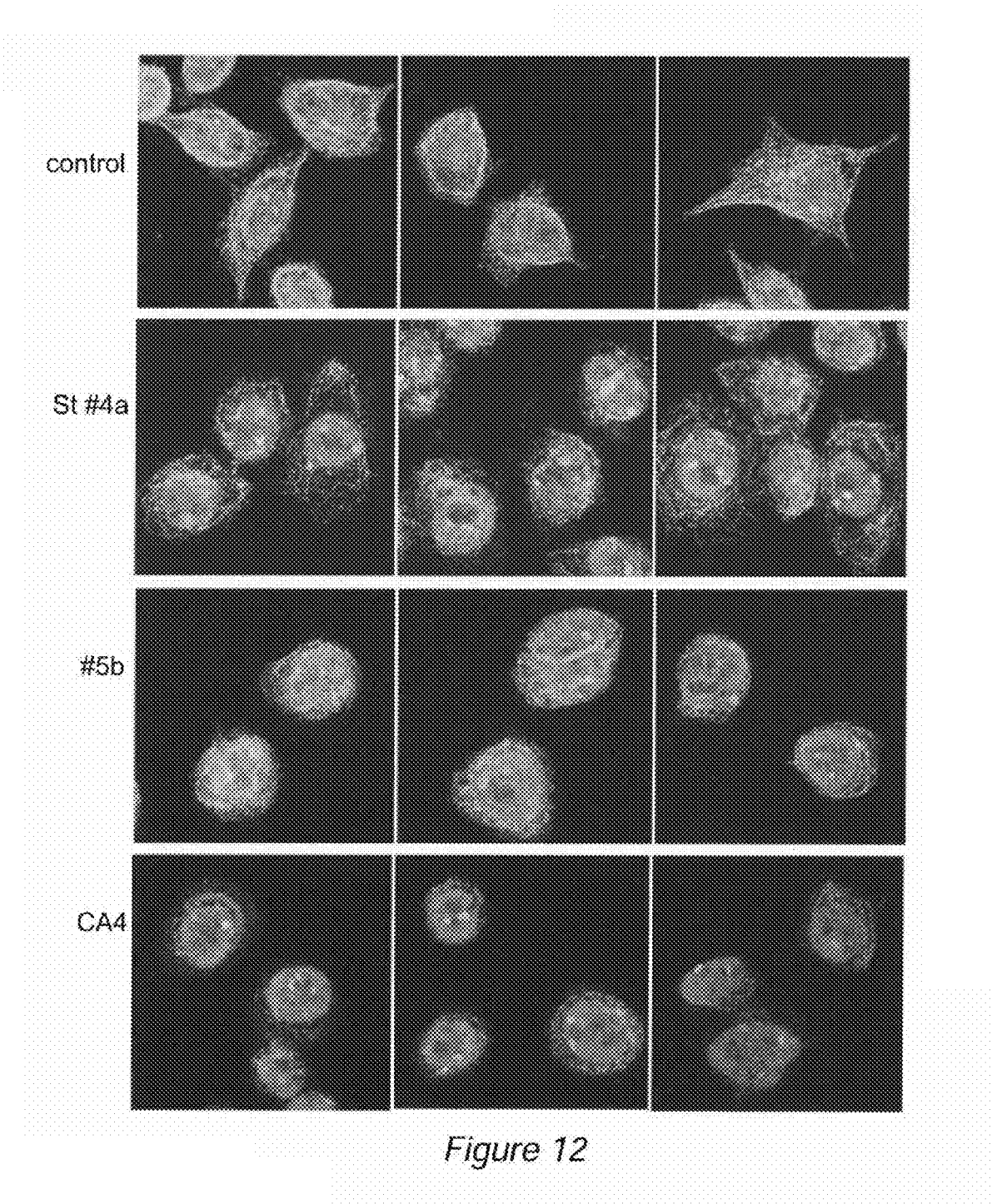
FIG. 12 shows UCI101 cells treated with CA4 (10 nM), stilbene 4a (100 nM), or 5b (3 μM) for 16 hours, and stained with tubulin antibody. Nuclei were stained with DAPI. After cells were treated with 5b and stilbene 4a, cells rounded up due to partial disruption of microtubules. Cells treated with CA4 also rounded up and exhibited complete disruption of microtubules.

We also stained the microtubules of MDA-MB231 cells treated with stilbene 4a, CA4 or 5b for comparison (FIG. 11). In the control cells, the pattern of microtubules appeared to be organized around a microtubule organizing center and in a network pattern. The positive control with vincristine had a fine granular pattern without formation of microtubules. Both CA4 and stilbene 4a did not completely disrupt microtubule formation, but cells treated with these two compounds exhibited multiple micronuclei after overnight treatment. 5b completely disrupted microtubule formation in the cell at the right lower corner. In cells in which microtubule formation was not completed disrupted, exposure to 5b resulted in the appearance of multiple microtubule organizing centers (the cell at the left upper corner). When the same experiment was carried out with UCI-101 cells, the results showed the same patterns of microtubule staining (FIG. 12). These data suggest that 5b may have a unique ability to block cell cycle arrest either kinetically through conversion to stilbene 4a, or dynamically through a differential effect on tubulin isomers.

Figure 13A:
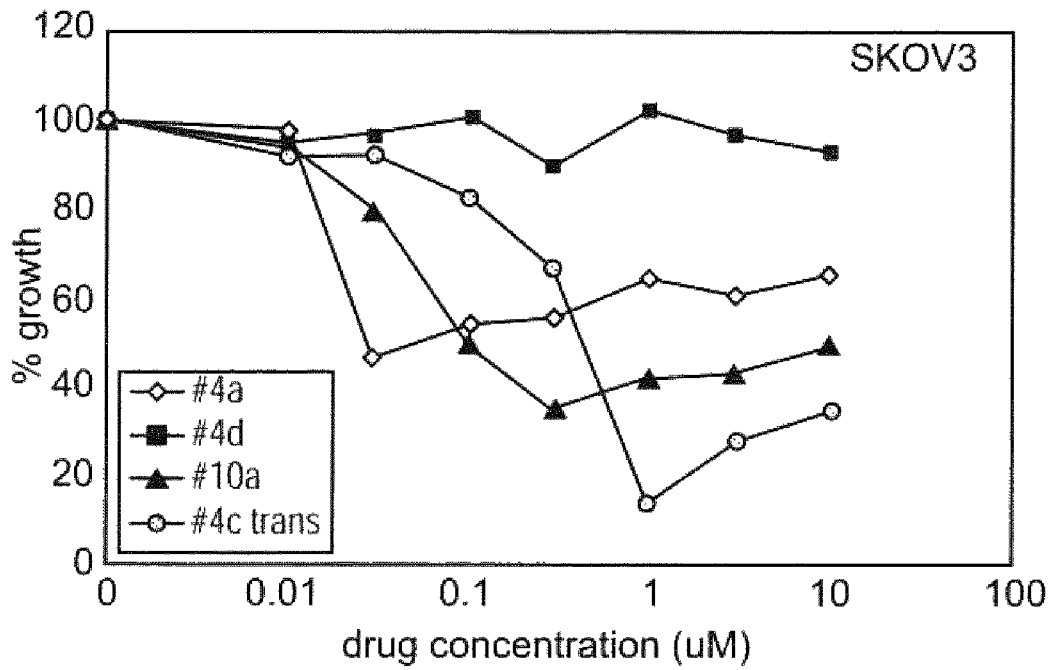
FIG. 13a-b shows SKOV3 ovarian cancer cells treated with various microtubule interfering agents. Cells were incubated with various concentrations of the compounds for 48 hours. Cell growth was measured by Alamar Blue™ staining and the percentage of cell growth inhibition was calculated and compared with the control cells that were treated with 0.1% DMSO, the vehicle for the stilbene compounds. SKOV-3 cells are most sensitive to CA4 with an effective concentration at 0.01 μM, whereas other compounds, including stilbene 4a, vincristine, colchicine, and 13a, were effective at 0.1 μM. Other derivatives, 10a and stilbene 4c trans were also effective, but 4d was not.
Figure 13B:
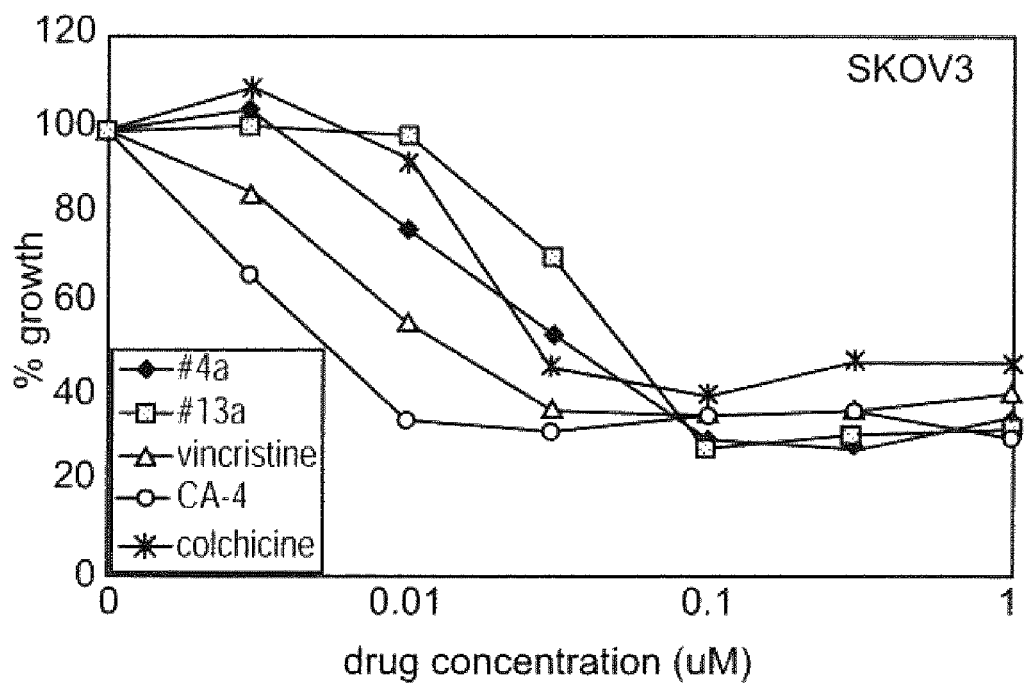

Finally, some compounds were tested in SKOV ovarian cancer cells and similar results were obtained. CA4 was the most potent compound and effective at 10 nM. Colchicine, vincristine, stilbene 4a and 13a had similar activities and displayed an $IC_{50}$ between 50-100 nM (FIG. 13a). Two compounds with other side chain modifications, 4d and 10a, showed that 10a maintains activity at 0.1 µM whereas 4d is not active (FIG. 13a-b). In addition, the trans isomer of stilbene 4c (another active form of stilbene 4c trans), was also active at a concentration of 0.3-1 µM (FIG. 13a-b)

Example 13

Disruption of Tumor Vascular Perfusion by Stilbenes

Method

In order to establish that stilbenes suppress tumor perfusion by damaging tumor endothelial cells, we first incubated human vascular endothelial cells (HUVECs) with various concentrations of stilbenes in vitro. After 24 hours of incubation, cells were processed for flow cytometry analysis with propidium iodide staining. Cells were also fixed with 2% paraformaldehyde and stained with anti-tubulin antibody to examine tubulin disruption and with DAPI to analyze nuclear fragmentation.

Dynamic-contrast enhanced magnetic resonance imaging (DCE-MRI) scanning was used to investigate tumor perfusion in vivo. Immunodeficient nude mice were first injected with Hep3B hepatocellular carcinoma cells subcutaneously. When the tumor reached a diameter of 0.8 cm or larger, mice were imaged with MRI to establish a pre-treatment baseline with and without intravenous injection of gadolinium contrast (0.02 cc from tail vein). The post gadolinium images were collected every minute for total 30 min. One day after the first imaging and gadolinium was washed out, mice were treated with stilbene 4a at 50 mg/kg intraperitoneally. Four hours later, images were obtained using the same protocol every minute for 30 minutes. Images with and without stilbene treatment from the same mice were compared directly to avoid any variation between different mice.

Results

Figure 14A:
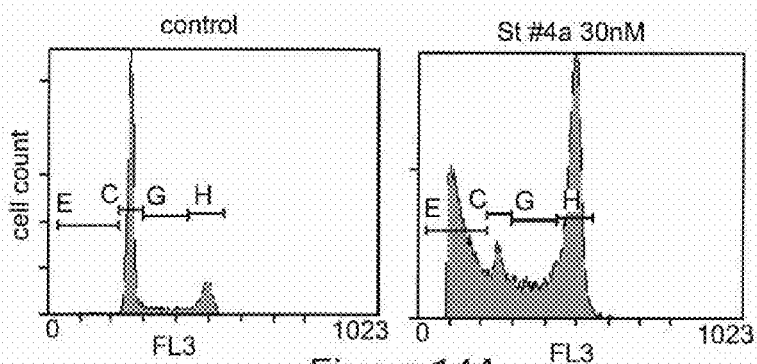
FIG. 14a-b shows that human umbilical vein endothelial cells (HUVECs) are highly sensitive to stilbenes 4a and 4c. (a) Flow cytometry analysis. HUVECs were treated with 30 nM of stilbene 4a for 16 hours followed by staining with PI and subjected to flow cytometry analysis. A large subG0/1 population, representing apoptotic cells, appeared along with reverse of the G1/G2 ratio. (b) Immunofluorescent staining of the HUVECs with antibody against tubulin. Nuclei were counter-stained with DAPI. Stilbene 4a disrupted microtubules at a concentration of 30 nM or higher. Stilbene 4c disrupted microtubules at 100 nM. Nuclei also showed fragmentation, a feature of apoptotic cells.
Figure 14B:
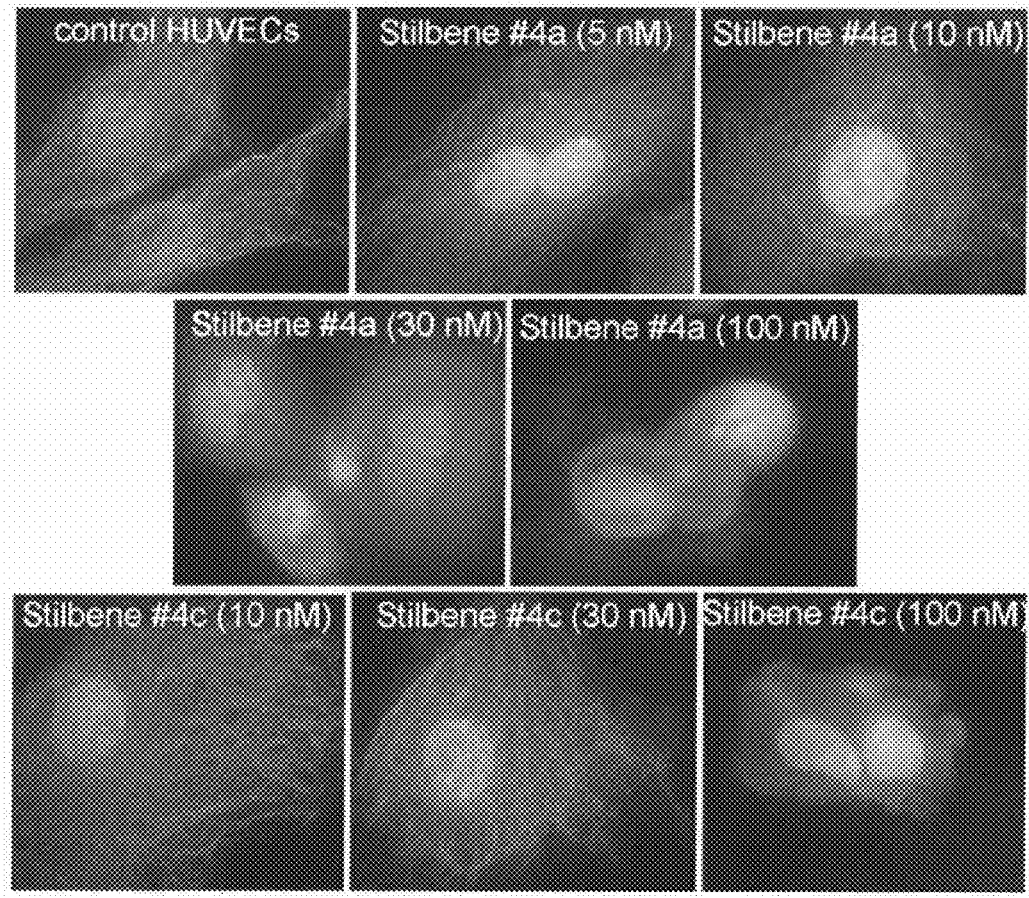

Stilbenes 4a and 4c can Disrupt Microtubule and Induce Apoptosis in Endothelial Cells In order to examine the vascular disrupting effect of stilbenes, we treated human umbilical vein endothelial cells (HUVECs) with stilbenes 4a and 4c. After 16 hours of incubation, stilbene 4a induced a significant apoptotic population of subG0/1 cells (FIG. 14a). Cells stained with tubulin antibody revealed that stilbene 4a effectively disrupts microtubules of HUVECs at 0.03 µM or higher. The nuclei of same cells exhibited apoptotic features (FIG. 14b). The same study with stilbene 4c showed that stilbene 4c was also effective at 0.1 µM (FIG. 14b), confirming that endothelial cells are highly sensitive to stilbenes.

Stilbene 4a Suppresses Tumor Perfusion without Damaging Normal Organ Perfusion

Figure 15:
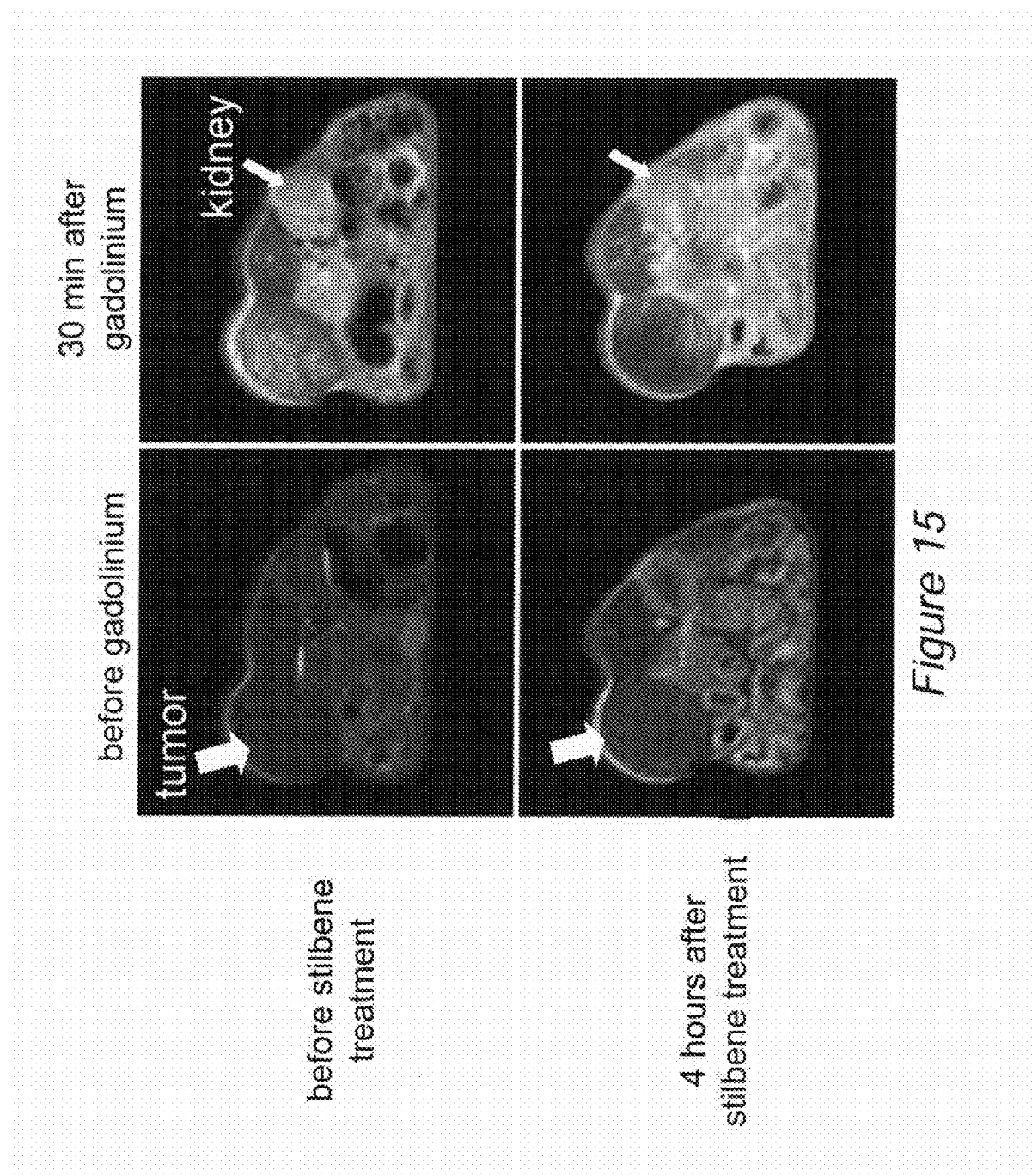
FIG. 15 shows the selective disruption of tumor vascular perfusion by stilbene 4a. Mice with established tumor xenografts were used for this study. The left upper panel shows the baseline T1-weighted MRI image before contrast injection. Tumor and kidney, as the representative normal organ, were marked by arrowheads. Right upper panel shows the image at 30 min after gadolinium injection and demonstrates tumor vascular perfusion by enhancement in the tumor region. Mice were then left overnight to wash out gadolinium and treated with stilbene 4a at 50 mg/kg intraperitoneally. 4 hours after stilbene injection, mice were imaged with the same protocol. The left lower panel shows the baseline image of the same mouse before gadolinium injection. Only a small amount of residual gadolinium was still in the tissues. The right lower panel shows the T1-weighted image obtained 30 min after gadolinium injection. Kidney and other normal tissue exhibited a strong enhancement similar to the upper panels before stilbene 4a treatment. In contrast, tumor enhancement was significantly compromised. This study confirmed that stilbene 4a can selectively suppress tumor vascular perfusion without compromising normal vascular perfusion.

To study the vascular disrupting effect of stilbene 4a in vivo, DCE-MRI was used to determine the vascular perfusion of tumors with and without stilbene treatment. Nude mice were injected with Hep3B hepatocellular carcinoma cells subcutaneously and tumors were allowed to develop for 3-4 weeks. Mice were anesthetized with isoflurane and subjected to imaging without gadolinium contrast to obtain a baseline as shown in left upper panel of FIG. 15. The section is obtained at the center of the tumor, and kidneys in the same section are used as an internal organ control. We then injected 20 µl of gadolinium (OmniScan) via tail veins, and the mice were analyzed with a rapid sequence MRI every minute for a total of 30 min. Both tumor and kidney exhibited an increase in MRIs signals after injection of gadolinium, which represents perfusion of tumor and kidney (FIG. 15, right upper panels). Mice were then left for 24 hours to let gadolinium be eliminated from the mice. The same mice were treated with 50 mg/kg stilbene 4a by intraperitoneal injection on the second day. Four hours after injection of stilbene 4a, the mice were imaged again before and after gadolinium injection by the same protocol and compared with the previous pair of images before stilbene treatment. In the baseline image before gadolinium injection, the T1 weighted image has a small increase of baseline MRI signals compared with the image of untreated mice (FIG. 15, left lower panel), suggesting that a small amount of residual gadolinium remained in the body from the previous day. After injection of gadolinium, the kidney and all other organs showed enhanced signals. However, the tumor region showed a significantly less gadolinium enhancement (FIG. 15, right lower panel), suggesting that stilbene 4a could have selective inhibition of tumor perfusion but not normal organ perfusion.

Example 14

Stilbenes do not Damage Bone Marrow Progenitor Cells

Methods

Isolation of Mouse C-Kit-Positive Progenitor Cell

Mouse bone marrow was harvested from femur and tibia of BALB/c mice (H2d, CD45.2), subjected to red blood cell lysis, and labeled with anti-c-kit (3C11; CALTAG Laboratories, Burlingame, Calif.) and streptavidin-conjugated microbeads for MACS separation (Miltenyi Biotech, Auburn, Calif.). The c-kit positive marrow progenitor cells were incubated in Iscove's Modified Eagle's Media supplemented with 30% fetal bovine serum, erythropoietin, stem cell factor and interleukin-3 with or without stilbenes 4a or 4c. The ability of long-term proliferation of the c-kit-positive cells was evaluated with colony forming assay. Cells were first treated with DMSO, stilbenes 4a or 4c for 5 h and a fraction of the cells (4000 cells) were plated in the same enriched culture media with methylcellulose for colony forming assays. The grossly visible colonies were counted after 14 days of incubation.

Bone Marrow Transplantation in Mice

C57BL/6J (H2b, CD45.2) mice served as bone marrow donors and were between 6-10 weeks of age. Mouse bone marrow mononuclear cells were harvested and c-kit positive cells were isolated as described previously [33, 34]. Cells were incubated with DMSO or stilbenes 4a or 4c at 0.1 or 0.5 µM for 16 hours and injected into tail veins of B6.SJL-Ptprca (H2b, CD45.1) recipient mice given 1200 cGy split-dose total body irradiation from a 137-Cesium irradiator delivered at a dose rate of 85 cGy/minute. Peripheral blood engraftment in recipient mice was assessed by flow cytometry analysis for CD3+ (145-2C11; BD Biosciences, San Jose, Calif.) T-cells, B220+ (RA3-6B2) B-cells, Mac1+ (M1/70.15) monocytes, and Gr1+ (8C5) granulocytes and distinguished between donor versus recipient with anti-CD45.1 (A20) and anti-CD45.2 (104) monoclonal antibodies.

Results

Stilbenes do not Damage Normal Bone Marrow Progenitor Cells

Figures 16A, 16B:
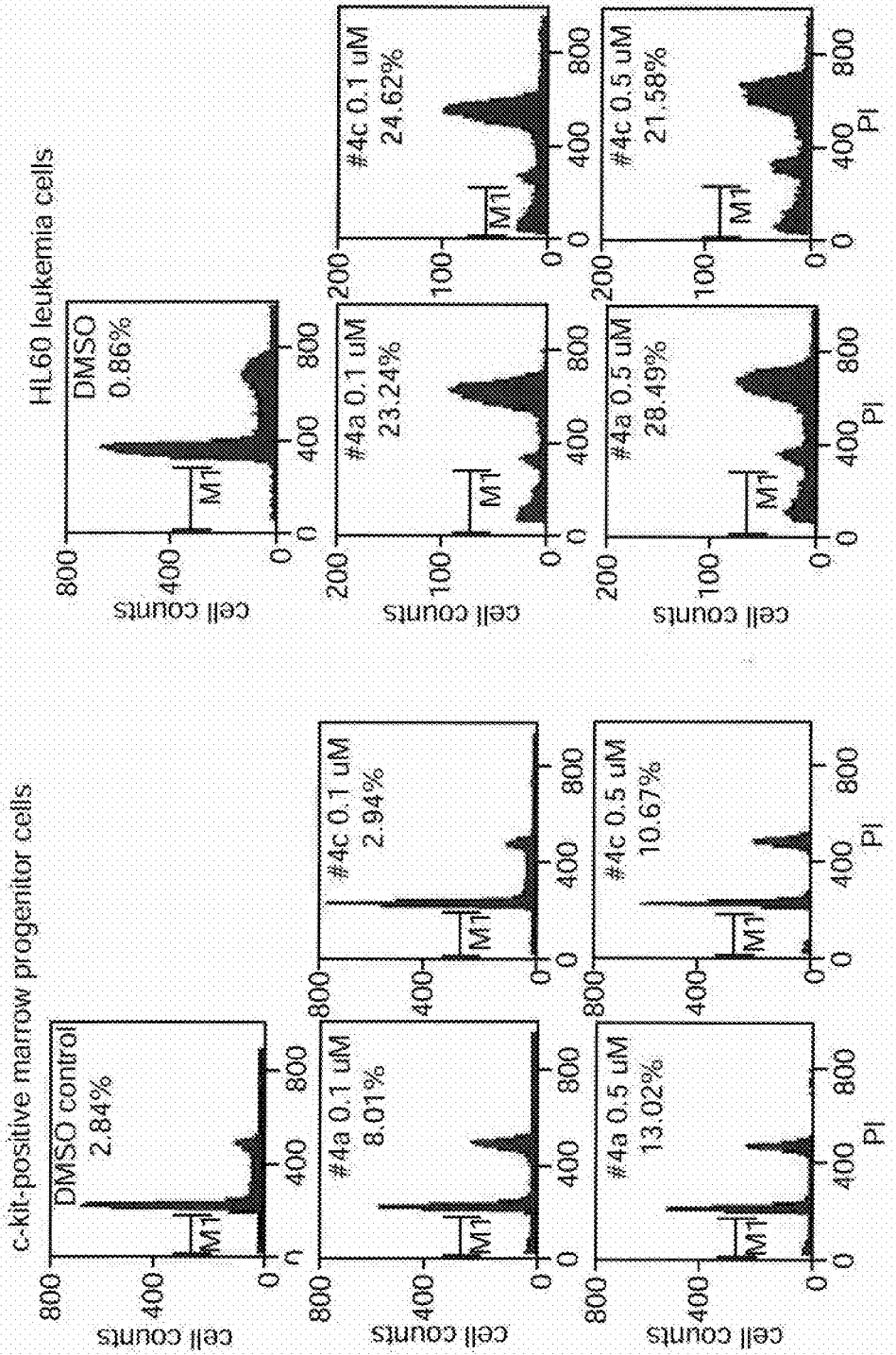
FIG. 16. (a) Effect of stilbenes in normal bone marrow progenitor cells. c-kit-positive bone marrow mononuclear cells were isolated for incubation with stilbenes 4a or 4c at 0.1 or 0.5 nM for 16 hours. Cells were harvested for fixation and PI staining. Cell cycle analysis and quantification of the subG$_{0/1}$ population were analyzed by FACScan flow cytometry. The percentages of the apoptotic population were indicated. Shown are the representatives of two independent experiments. (b) Effect of stilbenes in HL60 cells as positive control. HL60 cells were treated with stilbenes 4a or 4c in the same medium as the positive control. (c) Colony forming assay of the stilbene-treated c-kit-positive cells. A fraction of the cells in (a) were diluted and plated on methylcellulose medium at various densities. Cells were incubated for 14 days and the grossly visible colonies were counted. (d-e) Stilbenes do not affect the ability of engraftment of bone marrow progenitor cells. Isolated bone marrow c-kit-positive progenitor cells were incubated with DMSO or stilbenes 4a or 4c at 0.1 or 0.5 μM for 16 hours and injected into tail veins of CD45 congenic mice lethally irradiated with 1200 cGy. Mice were monitored for survival and lineage-specific donor engraftment by flow cytometry analysis of peripheral blood. The percentage of donor cells in T, B, and granulocytic series of the recipients were studied at 7 and 14 weeks after transplantation. Stilbene treated c-Kit progenitor cells had the same percentage as the DMSO treated control in all series.
Figure 16C:
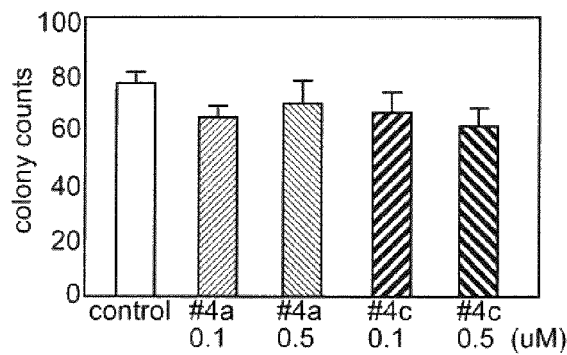

We next evaluated the hematopoietic toxicity of stilbenes. Mouse bone marrow was harvested from BALB/c mice and enriched for c-kit-positive progenitor cells by micromagnetic separation. We incubated the c-kit positive marrow progenitor cells with 0.1 or 0.5 µM stilbenes 4a or 4c in the presence of stem cell factor and interleukin-3. For comparison, HL60 leukemia cells were incubated with the same media containing stilbenes 4a and 4c as the positive control. After a 16-hour incubation period, cells were stained with propidium iodide. Flow cytometry analysis revealed that 0.1 and 0.5 µM of stilbene 4a increased the $subG_{0/1}$ and $G_2$ population slightly, but the majority of marrow progenitor cells are still in $G_1$ phase without reversing the $G_1/G_2$ ratio. Marrow progenitor cells were similarly not affected by stilbene 4c at 0.1 µM, but had a small increase in $subG_{0/1}$ and $G_2$ population when incubated with 0.5 µM (FIG. 16a). In contrast, HL60 cells had over 20% apoptosis and reversed $G_1/G_2$ ratio after stilbene treatment (FIG. 16b). Stilbene treatment of marrow progenitor cells also did not diminish colony formation after plating with erythropoietin, stem cell factor and interleukin-3 in long-term culture (FIG. 16c). Hence stilbenes 4a and 4c are cytotoxic to leukemia cells but much less toxic to normal bone marrow progenitor cells, the favorable tumor selectivity for further drug development.

Figure 16D:
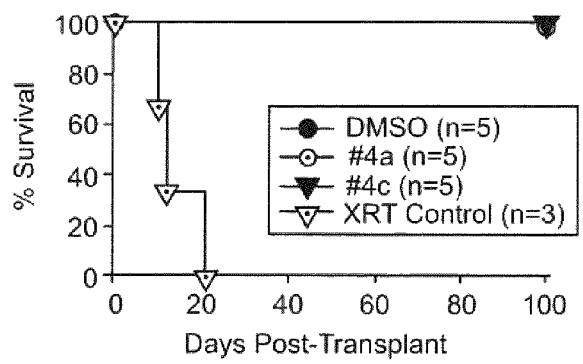
Figure 16E:
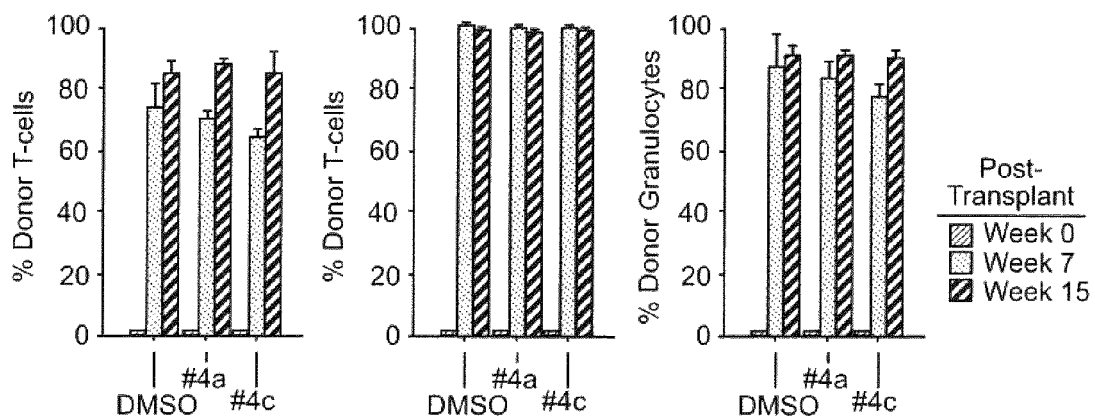

To further confirm that stilbenes have minimal hematopoietic toxicity, we evaluated the long-term in vivo engraftment capability of hematopoietic progenitor cells. We injected stilbene-treated c-kit-positive progenitor cells isolated from C57BL/6 mice into lethally irradiated CD45 congenic mice. Radioprotection was not compromised as all mice were rescued from lethal irradiation when given marrow progenitor cells exposed to either stilbenes 4a or 4c (FIG. 16d). The multilineage differentiation potential of stilbene-treated marrow progenitor cells was fully preserved as evidenced by the presence of donor-derived T-cell, B-cell and macrophage/granulocyte populations when determined by flow cytometry analysis of peripheral blood 7 weeks following transplantation (FIG. 16e). Further, durable high-level donor chimerism attained following engraftment with stilbene-treated marrow progenitor cells remained indistinguishable from control mice up to 15 weeks post-injection, thus demonstrating preservation of self-renewal capacity within the stem cell compartment. These results indicate that stilbenes do not detectably affect engraftment ability of bone marrow stem and progenitor cells.

Example 15

Determination of the Cellular Compensatory Mechanism of Stilbenes

Figure 17:
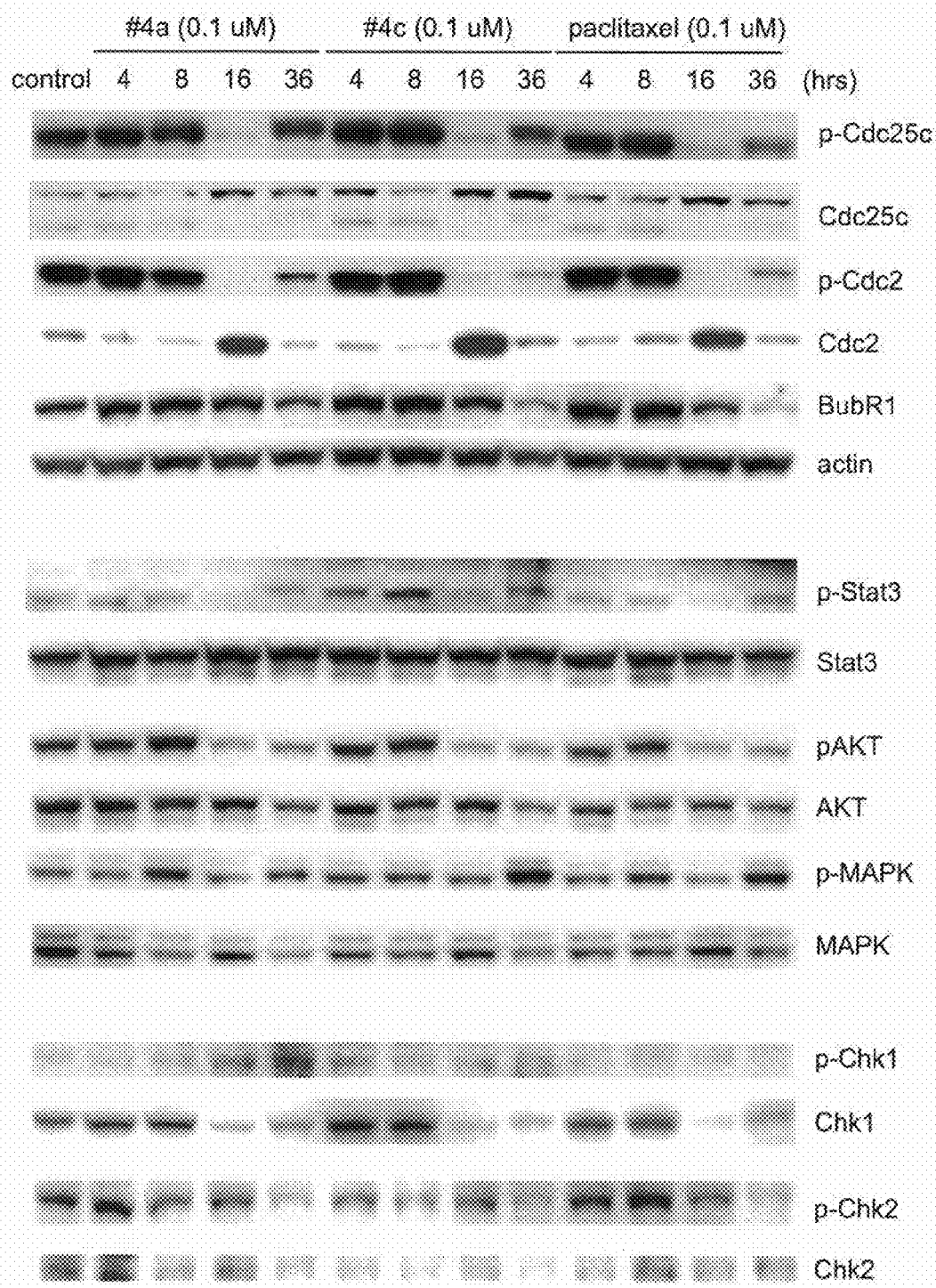
FIGS. 17 and 18 shows signal transduction events in cells treated with stilbene 4a, stilbene 4c, paclitaxel (Taxol) (FIG. 17), CA4, 13a and vincristine (FIG. 18). All these agents are microtubule interfering agents but with different binding sites. Cells were harvested at 0, 4, 8, 16 and 36 hours after drug treatment for Western blot analysis. The top set shows the kinases that are related with cell cycle transition from G2 to M phase, including Cdc25C, Cdc2, and BubR1 spindle check point regulator. Phosphorylation of both Cdc25C and Cdc2 disappeared after 16 hours and slightly recovered at 36 hours. BubR1 levels also decreased at 36 hours. The middle panel shows the changes of 3 key signal transduction mediators, Stat3, Akt, and MAPK. Phosphorylation of Stat3 steadily increased until 16 hours but disappeared at 36 hours. Akt phosphorylation decreased after 16 hours of treatment. No significant change was seen in MAPK. The lower panel showed changes in Chk1 and Chk2.
Figure 18:
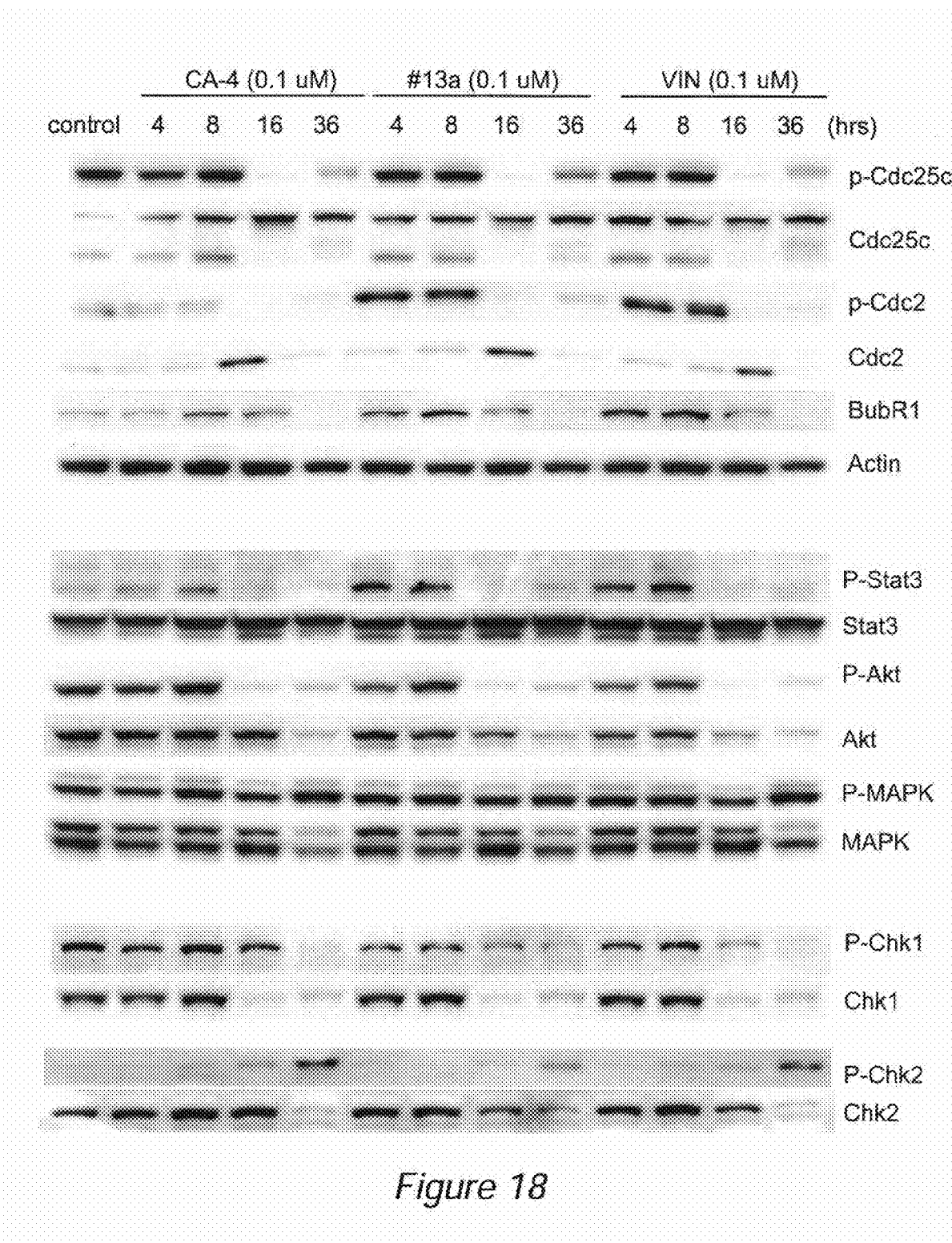

In order to understand the mechanism of resistance of stilbenes, various signal transduction pathways were investigated to examine how cells respond to stilbene treatment. UCI101 ovarian cancer cells were treated with stilbenes 4a, 4c or paclitaxel (Taxol) at 0.1 µM for 0, 4, 8, 16 and 36 hours. Cells were harvested for Western blotting. Changes in the kinases involved in cell cycle progression from G2-M transition were first determined in Cdc2, Cdc25c, and mitotic spindle check point regulator BubR1. Phosphorylation of Cdc2 at Tyr15 decreased dramatically after 16 hours of stilbene or paclitaxel treatment even though the total amount of Cdc2 increased significantly at the same time point. 36 hours after treatment, rephosphorylation of Cdc2 was observed. Cdc25c, the upstream phosphatase and regulator of Cdc2, had a similar phosphorylation pattern with dephosphorylation noted at 16 hours and rephosphorylation at 36 hours. The higher molecular weight isomer of Cdc25c, the mitotic form, increased at 16 and 36 hours. This finding suggests that cells treated with any of these three microtubule-interfering agents are arrested in mitotic stage, as shown by the activation (dephosphorylation) of Cdc2, which is likely due to activation (dephosphorylation) of Cdc25c. The spindle checkpoint regulator BubR1 exhibited a transient increase at 4 and 8 hours and then steadily decreased afterwards at 16 and 36 hours in cells treated with stilbene 4c and paclitaxel. Stilbene 4a appeared to exhibit some differences as the increase of BubR1 appeared more persistent and did not decrease as much at the 36-hour time point (FIG. 17). A similar study was then performed with other microtubule interfering agents such as combretastatin A4, 13a and vincristine for comparison. A similar trend was observed among these three microtubule interfering agents (FIG. 18).

Several major regulators of signal transduction pathways were then investigated to understand how the critical survival kinases change to compensate the microtubule interference effect of stilbene. Three well-known pathways that are known to be involved in cell proliferation were examined. Stat3 exhibited a transient increase in phosphorylation at 4 and 8 hours after treatment with stilbenes 4a and 4c but then decreased after 16 hours. This phenomenon was more pronounced in cells treated with 13a and vincristine. No change of total Stat3 was seen. Phosphorylation of Ser473 of Akt may have a small degree of increase at 8 hours but decreased significantly at 16 and 36 hours after treatment with all tested inhibitors. In contrast, phosphorylation of MAPK was unchanged at all four time points studied, suggesting that MAPK is not involved in the cellular compensatory response to microtubule inhibitors (FIGS. 17 and 18).

Kinases that are involved in DNA damage responses such as Chk1 and Chk2 also exhibit changes after treatment with stilbenes or other microtubule inhibitors. The total amount of Chk1 decreased at 16 and 36 hours, but phosphorylation of Chk1 increased uniquely at 36 hours only after treatment with stilbene 4a. Stilbene 4c, paclitaxel, combretastatin A4, 13a and vincristine do not cause more phosphorylation of Chk1, suggesting that stilbene 4a exhibits a unique mechanism for inducing Chk1 activation. In contrast, Chk2 failed to show any enhanced phosphorylation or activation. However, the total amount of Chk2 decreased after treatment with various microtubule inhibitors (FIGS. 17 and 18).

Example 16

Stilbenes have a Unique Mechanism of Causing Cell Death that is Different from CA4

Figure 19:
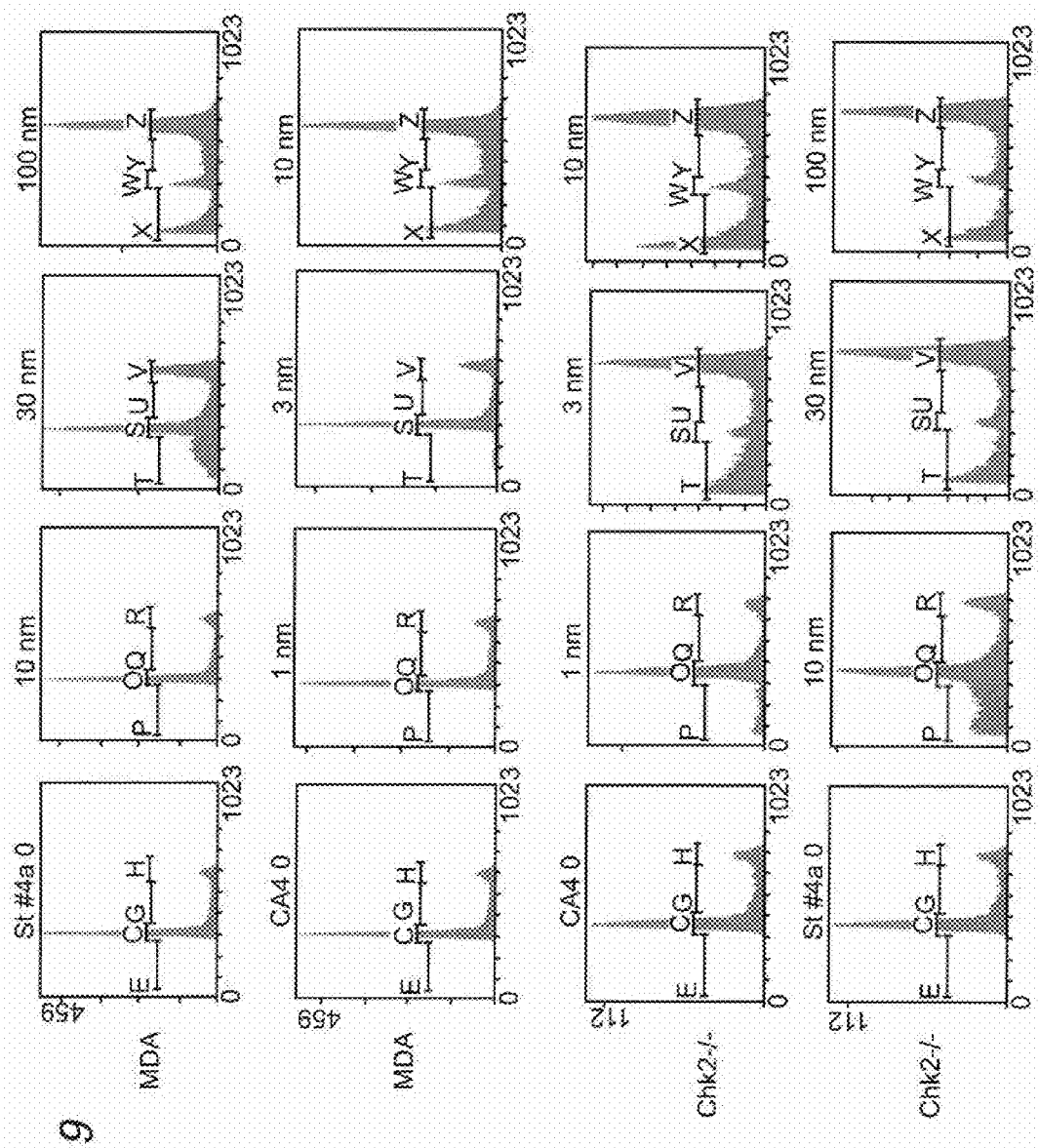
FIG. 19 shows the comparison of cell cycle changes of MDA-MB231 and Chk2−/− cells treated with stilbene 4a and CA4. Cells were treated with various concentrations of stilbene 4a or CA4 for 16 hours followed by PI staining and FACscan analysis. Chk2−/− cells are more sensitive to either agent, and the effective concentration decreased by three fold. A unique feature of stilbene 4a was noted when cells were treated with 30 nM. A subG0/1 population was noted with minimal G2 arrest, suggesting that this concentration of stilbene 4a induces cell death through a cell cycle-independent mechanism.

Due to the structural similarity between stilbene 4a and CA4, we investigated the difference in the biological activity of these two compounds in MDA-MB231 breast cancer cells and their Chk2-/- derivatives. Based on our previous $IC_{50}$ data, stilbene 4a is 10 times less potent than CA4. MDA-MB231 cells were treated with 10 nM stilbene 4a or 1 nM CA4. No change was observed, and an equal amount of cell death and G2 arrest was noted after treatment with both 100 nM stilbene 4a and CA4 (FIG. 19). However, a difference in cell cycle change was observed following treatment with 30 nM of stilbene 4a versus 3 nM of CA4. Stilbene 4a at 30 nM induced some degree of G2 arrest, but the ratio of G1/G2 did not reverse. This was also the case for cells treated with 100 nM stilbene 4a. A significant subG1/0 population was also noted. This finding suggests that stilbene 4a may have a G2/M arrest-independent mechanism of causing cell death, and this phenomenon is not present in CA4 (FIG. 19). One possible effect could be a DNA damage response, which is a common mechanism of multiple chemotherapeutic agents but not one of pure microtubule-interfering agents such a paclitaxel or vincristine. CA4 also does not have such mechanism in causing cell death. We then obtained conditional Chk1−/− and Chk2−/− cells, which were derived from the same MDA-MB231 cells for the same flow cytometry analysis. Chk1−/− cells were found to be more resistant to both stilbene 4a and CA4 (not shown). Cells treated with stilbene 4a or CA4 exhibited G2 arrest but the subG$_{1/0}$ population disappeared (FIG. 19), indicating the process of cell death is dependent of Chk1 and loss of Chk1 confers resistance to stilbene 4a and CA4. In contrast, Chk2−/− cells were more sensitive to stilbene 4a. When Chk2−/− cells were treated with 10 nM stilbene 4a, which did not cause any effect in MDA-MB231 cells, a significant subG$_{1/0}$ population developed without G2 arrest (FIG. 19). This finding suggests that a Chk2-inhibited cell death mechanism is utilized when cells are treated with low doses of stilbene 4a. This mechanism is not obvious in higher drug concentrations at which the G2 arrest from microtubule interference is dominant. Therefore, in addition to their microtubule interfering effect, stilbenes have another mechanism to induce cell death. Thus, the use of a Chk2 inhibitor in combination with stilbenes may be a viable approach to enhancing the beneficial therapeutic effects of stilbenes.

Example 17

Activity of Selected Stilbene Derivatives 10a (depicted below) is a compound in which the methyl group at 3 position of stilbene 4a is replaced with —CH$_2$CH$_2$OH. 10a is active in suppressing tumor proliferation with an IC$_{50}$ of 0.3 μM in SNU423 hepatocellular carcinoma cells and MiaPaCa2 pancreatic cancer cells, and an IC$_{50}$ of 0.08 μM in MDA-MB231 breast cancer cells. Computer based structural modeling of 10a and tubulin confirmed that 10a can fit into the colchicine binding site pocket without restraint.

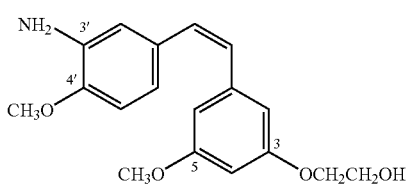

10a

The three compounds depicted below, 12a-c, combine the 3' amino and 4' methoxyl groups of stilbene 4a into a 5-atom ring. Computer based structural modeling suggests that they fit into the colchicine binding pocket. The biological activity of these compounds was tested in SNU423, MiaPaCa2 and MDA-MB231 cancer cells and the IC$_{50}$ for all three compounds is about 0.6±0.2 μM range.

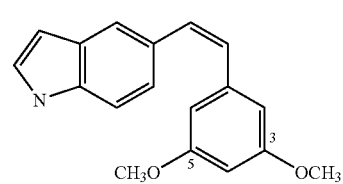

12a

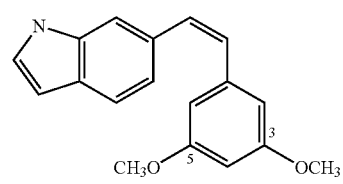

12b

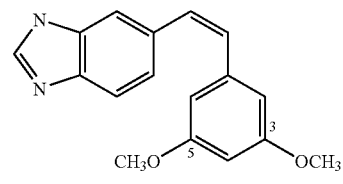

12c 13a (depicted below) is a compound in which an additional methyl group has been added to 12a. This addition enhances the binding affinity of 13a and its IC$_{50}$ is 0.01 μM in SNU423, MiaPaCa2 and MDA-MB231 cancer cells. A study of the animal toxicity revealed that mice survived after injection with 50 mg/kg of 13a, indicating low toxicity. However, transient neurotoxicity was observed. This compound, although one of the most potent stilbene derivatives with potency even slightly better than stilbene 4a in many studies, has the major problem of poor water solubility that may limit their potential of clinical application.

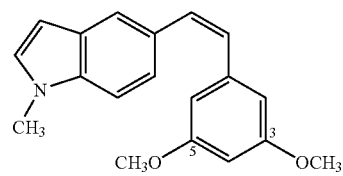

13a 4b (depicted below) differs from stilbene 4a in that the 3' amino group has been moved to the 2' position. Water solubility of this compound is enhanced by the formation of an oxalate salt. This compound is active in suppressing tumor cell proliferation with an IC$_{50}$ of 0.08 μM.

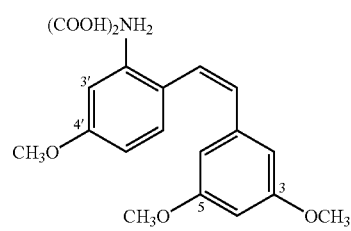

4b 10d (depicted below) differs from stilbene 4a in that the 5 methoxyl group is replaced by a hydroxyl group. This compound is active in suppressing tumor cell proliferation with an $IC_{50}$ of 1 μM.

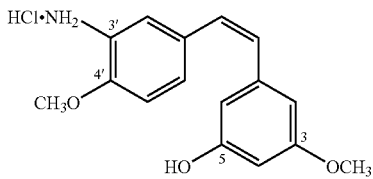

5d (see FIG. 2) is a modification of the amino group of stilbene 4a. Computer based structural modeling suggests that it fit into the colchicine binding pocket of tubulin, and could be a potential useful compound to fit into the colchicine site.

Example 18

Effect Stilbene 4a in Mice Xenograft Model

Methods

HL60 leukemic cells were injected subcutaneously into ICR-scid mice (Taconic Inc.) on flank. After tumor becomes visible after 12 days, Mice will be treated with stilbene 4a by intravenous injection after dissolved in 10% DMSO in normal saline. For acute effect study, mice were sacrificed 24 hours after injection and tumor and bone marrow were harvested for histological staining and flow cytometry analysis. For long term effect study, stilbenes were injected intravenously from tail veins at 2 or 10 mg/kg for 5 consecutive days. Negative control mice were treated with 10% DMSO in normal saline and positive control mice were treated with Ara-C at 5 mg/kg. Tumor volume was measured twice a week for 4 weeks by the long and short axes of tumor. Volume was calculated by the formula $ab^2/2$, in which "a" represents the long axis and "b" the short axis of tumor. Mice were euthanized if the calculated tumor reached 10% of the body weight.

Results

Effect of Stilbene 4a In Vivo

Acute toxicity in dose escalating study: We investigated the efficacy of stilbene 4a in vivo using mouse xenograft model. First we determined the maximal tolerated dose of stilbene 4a since it has a higher potency in vitro. Stilbene 5c at 6 or 33 mg/kg given intravenously did not cause any acute toxicity. Increasing the dose to 72 and 97 mg/kg lead to transient weakness as shown by dragging feet and sluggish movement for 10 to 15 min. Subsequently mice fully recovered 30 min after injection. If 100 mg/kg stilbene 4a was injected intraperitoneally, no sign of weakness was observed, suggesting a different pharmacokinetic profile between the two routes of administration.

Short term effect: We then tested the effect of stilbenes on tumor xenografts 24 hours after treatment. Mice with well-developed tumor at 1 cm in diameter were used for this study. Two mice were used in each group to study the effect of stilbene 4a at 10, 50 and 100 mg/kg injected intravenously. Mice were sacrificed 24 hours later and TUNEL analysis of tumor showed that the percentages of apoptosis were 22%, 62% and 58%, respectively (FIG. 20a). H & E staining of untreated tumor revealed a pattern of rapid tumor proliferation with occasional cell death. Tumor treated with 10 mg/kg stilbene 4a had a patch of cell death. The area of cell death enlarged in tumor treated with 50 mg/kg and the peripheral region was spared. In tumor treated with 100 mg/kg stilbene 4a, it was more obvious that the central portion of the tumor became dead and a peripheral area remained viable. Bone marrow from these mice was also isolated for TUNEL assays. No increase in TUNEL positive cells was observed, confirming that there is no acute marrow toxicity induced by stilbenes 4a at 50 and 100 mg/kg (data not shown).

Long term effect: Once we confirmed the short-term efficacy of stilbene 4a at 24 hours, we examined a different schedule and a lower dose of stilbene 4a. Same as the previous xenograft model, mice were injected intravenously with stilbene 4a at 2 mg/kg or 10 mg/kg daily for 5 days after tumor diameters reached 5 mm or more in size. Control mice were injected with 10% DMSO, in which stilbene 4a was dissolved. The positive control group was treated with Ara-C at 5 mg/kg/day for 4 days. Day 5 Ara-C was not given due to Ara-C-induced conjunctivitis. The growth curve of the tumor revealed that stilbene 4a was effective initially after treatment. But the residual tumor continued to grow after treatment was stopped (FIG. 20c). Mice were sacrificed 12 days after the first injection. Stilbene 4a, at 10 mg/kg, was able to suppress tumor growth by 50% when mice were sacrificed. Histological section of tumors revealed that most of the tumor are viable as expected and a small area of tumor appeared dead as shown by the PI staining and TUNEL analysis (not shown). Further adjustment of the dosing and schedule is necessary to achieve a better therapeutic efficacy.

Example 19

In Vivo Efficacy of 5a-c

Because of the limited solubility but high potency of stilbene 4a, the possibility of developing more water soluble prodrugs of stilbene 4a was explored. The structures of three such prodrug forms of stilbene 4a are depicted below. The addition of triethylene glycol (TEG) or morfolino groups serves to improve water solubility of the parent stilbene 4a. It is anticipated that these three compounds will be cleaved into stilbene 4a in serum and become the active form. Consistent with computer modeling studies which showed that the prodrugs could not fit into the colchicine binding site of tubulin (due to the size of the morpholino or TEG groups), the parent prodrug compounds themselves are much less active in vitro. They may become activated in vivo upon removal of the morpholino or TEG group, which converts the prodrugs to stilbene 4a.

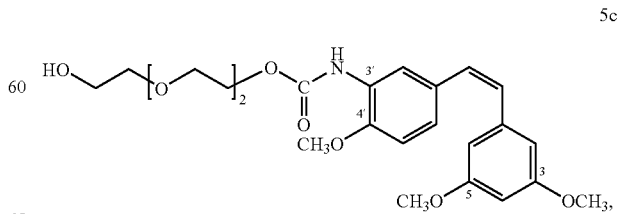

Triethyleneglycol (TEG) derivative

-continued

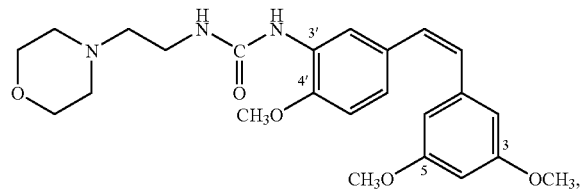

Morfolino-urea derivative

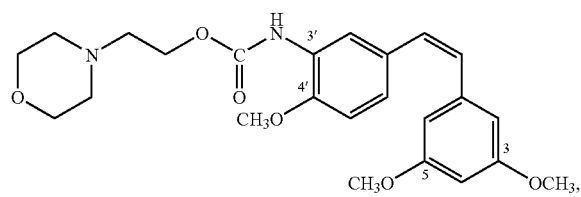

Morfolino-carbamate derivative

Figure 21A:
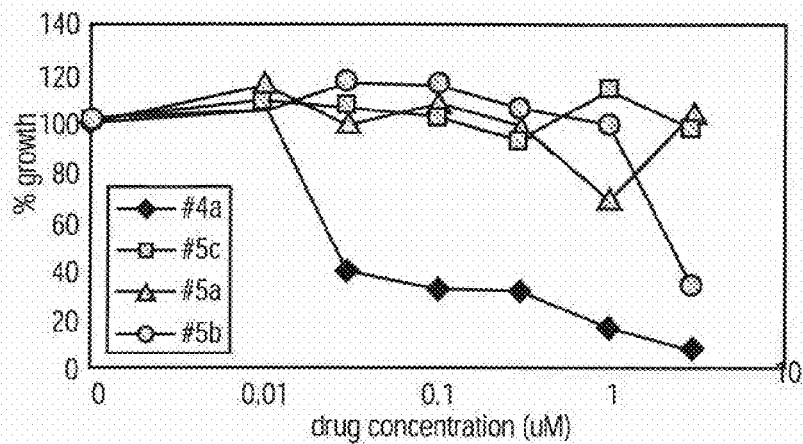
FIGS. 21a-e shows the development of 5b, a prodrug of stilbene 4a. (a) In vitro sensitivity of UCI101 cells toward three potential stilbene prodrugs, 5a-c, was tested in 96-well plates using Alamar Blue™ assays to determine cell growth inhibition. Only 5b at a concentration of 3 μM showed tumor growth suppression. (b) 5b induces cell cycle change and apoptosis in UCI101 cells. Cells were incubated with 5b at 1, 3, 10 μM for 16 hours followed by PI staining and flow cytometry analysis. A subG0/1 population, representing apoptotic cells, appeared along with a decrease of the G1/G2 ratio after cells were treated with 3 μM 5b. Higher concentration (10 μM) of 5b completely killed cells, as was the case with stilbene 4a at 100 μM. (c) Cells treated with stilbene 4a and 5b were stained with phospho-histone 3B, a mitotic marker. The positive signals of phospho-histone 3B were shown in green and nuclei were stained with DAPI in blue. Both stilbene 4a and 5b significantly increase the population of cells in mitotic stage. (d) In vivo efficacy of 5b compared with stilbene 4a. Nude mice were injected with UCI101 ovarian cancer cells and treated with 7 doses of 5b,c or stilbene 4a every 2-3 days. Tumor volume was calculated and plotted against days. 5b is the only compound that achieved statistical significance compared with control mice. (e) Mouse weight in various time points did not change during the course of the experiment, suggesting minimal toxicity form 5b.
Figure 21B:
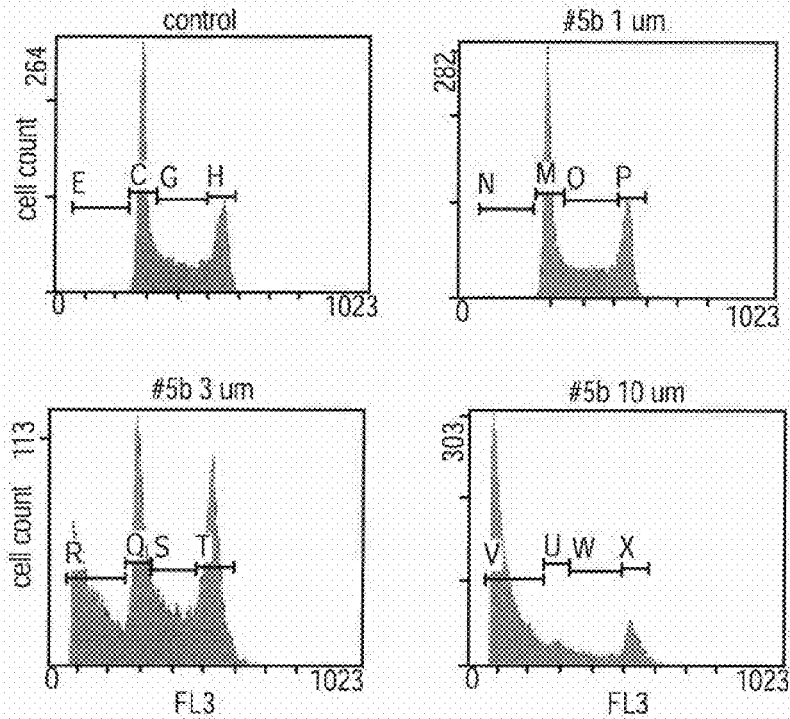
Figure 21C:
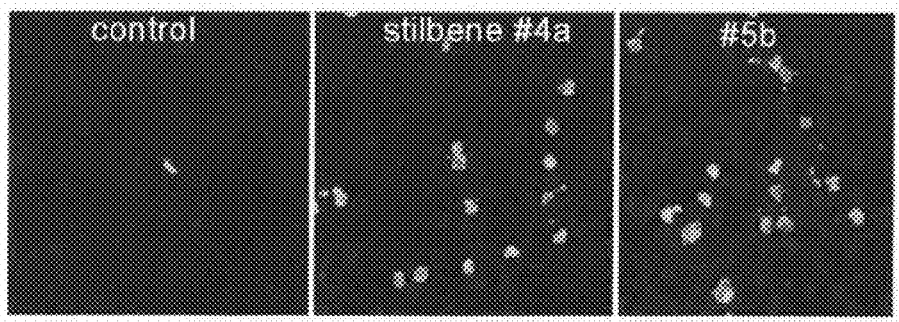

The in vitro efficacy of these three compounds was tested in UCI101 cells in 96-well plate format and stained with Alamar blue™, The growth suppression was calculated as was done similarly to other test compounds. The results showed that 5a and 5c did not suppress cell growth even at concentrations up to 3 µM. In contrast, 5b was found to be effective at concentrations of 3 µM or higher (FIG. 21a), a concentration that can be clinically achieved in vivo. An attempt to induce serum conversion by co-incubation of 5a-c with serum for 1 hour before treating cells failed to show any improvement in the in vitro activity (not shown). A dose response was then performed with various concentrations of 5b in vitro. At 1 µM, 5b was not effective in inducing cell death or cell cycle arrest. But at 3 µM, 5b showed a significant activity. When further increased to 10 µM, nearly all cells have committed to cell death (FIG. 21b). $IC_{50}$ of 5b was estimated to be 3 µM, which is about 100-fold less potent than its active form stilbene 4a. To confirm that 5b also induce cell cycle arrest in mitotic phase through depolarizing microtubule, cells treated with stilbene 4a or 5b were stained with a mitotic marker, phospho-histone 3B (FIG. 21c). Control cells are rarely positive for phospho-histone 3B staining, but cells treated stilbene 4a or 5b have a dramatic increase in positive cells. This study indicates that both stilbene 4a and 5b arrest cell cycle progression at the mitotic stage and also raises the possibility that positive phospho-histone 3b staining could be a useful biomarker for further development of stilbenes.

Figure 21D:
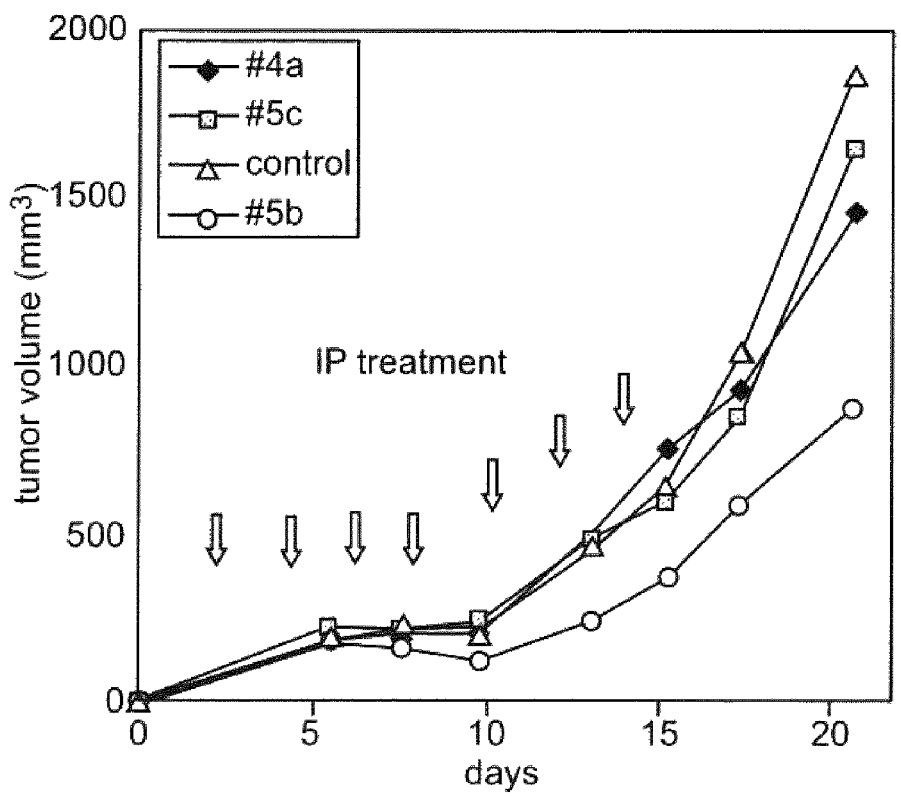
Figure 21E:
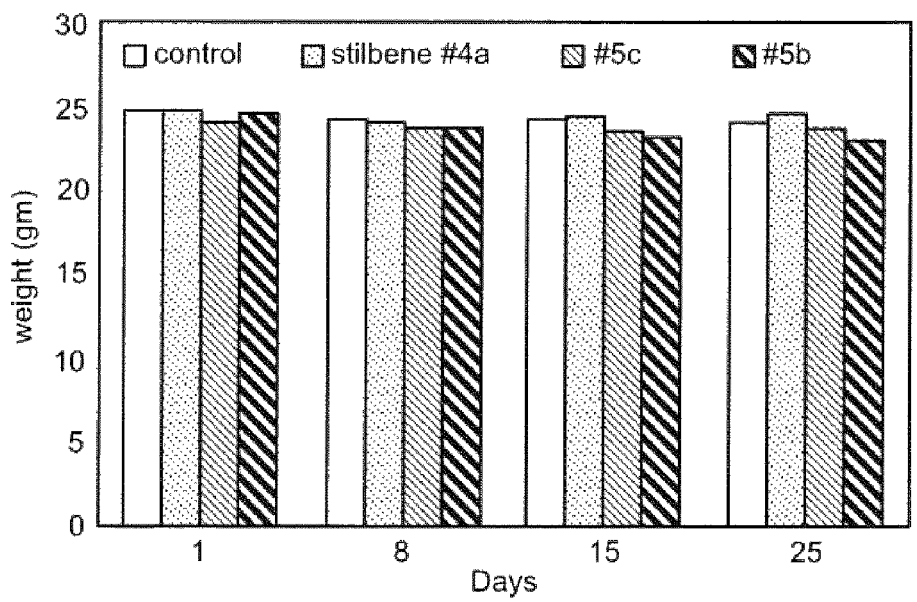

We next tested whether 5b could be converted into stilbene 4a in circulation. Mice were treated with 100 mg/kg by intraperitoneal injection for a preliminary toxicity study and mice tolerated well without complication. Blood was collected at 20, 60 and 240 min after injection for spot check of stilbene 4a level in serum. Stilbene 4a was indeed detected and the concentration of stilbene 4a was calculated to be 8% of that of 5b, and 5b also appears to stay in circulation longer than stilbene 4a, indicating that in vivo conversion of 5b occurs and there may be some pharmacokinetic advantage for 5b than stilbene 4a. The in vivo efficacy of 5b and 5c was compared to stilbene 4a in a pilot study using 5 mice in each group. Tumors in mice treated with 5c had a tumor growth rate the same as that of control mice, whereas 5b appeared to suppress tumor growth by about 40% (FIG. 21d). Mouse weight did not show any significant change in all control mice and those treated with stilbene 4a, 5c or 5b (FIG. 21e), suggesting that there is no obvious toxicity from 5b or stilbene 4a. Therefore 5b could be a more appropriate product for further drug development due to its advantage of high solubility and better pharmacokinetics.

REFERENCES

1. Pace-Asciak, C. R., et al., The red wine phenolics trans-resveratrol and quercetin block human platelet aggregation and eicosanoid synthesis: implications for protection against coronary heart disease. Clin Chim Acta, 1995. 235 (2): p. 207-19.
2. Kimura, Y., New anticancer agents: in vitro and in vivo evaluation of the antitumor and antimetastatic actions of various compounds isolated from medicinal plants. In Vivo, 2005. 19(1): p. 37-60.
3. Zhou, H. B., et al., Anticancer activity of resveratrol on implanted human primary gastric carcinoma cells in nude mice. World J Gastroenterol, 2005. 11(2): p. 280-4.
4. Larrosa, M., F. A. Tomas-Barberan, and J. C. Espin, The grape and wine polyphenol piceatannol is a potent inducer of apoptosis in human SK-Mel-28 melanoma cells. Eur J Nutr, 2004. 43(5): p. 275-84.
5. Roberti, M., et al., Synthesis and biological evaluation of resveratrol and analogues as apoptosis-inducing agents. J Med Chem, 2003. 46(16): p. 3546-54.
6. Pellegrini, F. and D. R. Budman, Review: tubulin function, action of antitubulin drugs, and new drug development. Cancer Invest, 2005. 23(3): p. 264-73.
7. Jiang, N., et al., Advances in mitotic inhibitors for cancer treatment. Mini Rev Med Chem, 2006. 6(8): p. 885-95.
8. Pettit, G. R., et al., Isolation and structure of the strong cell growth and tubulin inhibitor combretastatin A-4. Experientia, 1989. 45(2): p. 209-11.
9. Siemann, D. W., D. J. Chaplin, and M. R. Horsman, Vascular-targeting therapies for treatment of malignant disease. Cancer, 2004. 100(12): p. 2491-9.
10. Thorpe, P. E., Vascular targeting agents as cancer therapeutics. Clin Cancer Res, 2004. 10(2): p. 415-27.
11. Tozer, G. M., C. Kanthou, and B. C. Baguley, Disrupting tumour blood vessels. Nat Rev Cancer, 2005. 5(6): p. 423-35.
12. Stevenson, J. P., et al., Phase I trial of the antivascular agent combretastatin A4 phosphate on a 5-day schedule to patients with cancer: magnetic resonance imaging evidence for altered tumor blood flow. J Clin Oncol, 2003. 21(23): p. 4428-38.
13. Rustin, G. J., et al., Phase I clinical trial of weekly combretastatin A4 phosphate: clinical and pharmacokinetic results. J Clin Oncol, 2003. 21(15): p. 2815-22.
14. Anderson, H. L., et al., Assessment of pharmacodynamic vascular response in a phase I trial of combretastatin A4 phosphate. J Clin Oncol, 2003. 21(15): p. 2823-30.
15. Beerepoot, L. V., et al., Phase I clinical evaluation of weekly administration of the novel vascular-targeting agent, ZD6126, in patients with solid tumors. J Clin Oncol, 2006. 24(10): p. 1491-8.
16. Petrenko, Y. A., et al., The reduction of Alamar Blue by peripheral blood lymphocytes and isolated mitochondria. Ukr Biokhim Zh, 2005. 77(5): p. 100-5.
17. Jang, M., et al., Cancer chemopreventive activity of resveratrol, a natural product derived from grapes. Science, 1997. 275(5297): p. 218-20.

18. Le Corre, L., et al., Resveratrol and breast cancer chemoprevention: Molecular mechanisms. Mol Nutr Food Res, 2005.
19. Fulda, S. and K. M. Debatin, Resveratrol-mediated sensitisation to TRAIL-induced apoptosis depends on death receptor and mitochondrial signalling. Eur J Cancer, 2005. 41(5): p. 786-798.
20. Rodrigue, C. M., et al., The cancer chemopreventive agent resveratrol induces tensin, a cell-matrix adhesion protein with signaling and antitumor activities. Oncogene, 2005.
21. Azios, N. G. and S. F. Dharmawardhane, Resveratrol and estradiol exert disparate effects on cell migration, cell surface actin structures, and focal adhesion assembly in MDA-MB-231 human breast cancer cells. Neoplasia, 2005. 7(2): p. 128-40.
22. Belleri, M., et al., Antiangiogenic and vascular-targeting activity of the microtubule-destabilizing trans-resveratrol derivative 3,5,4'-trimethoxystilbene. Mol Pharmacol, 2005. 67(5): p. 1451-9.
23. Gosslau, A., et al., A methoxy derivative of resveratrol analogue selectively induced activation of the mitochondrial apoptotic pathway in transformed fibroblasts. Br J Cancer, 2005. 92(3): p. 513-21.
24. Eberhard, A., et al., Heterogeneity of angiogenesis and blood vessel maturation in human tumors: implications for antiangiogenic tumor therapies. Cancer Res, 2000. 60(5): p. 1388-93.
25. McDonald, D. M. and P. L. Choyke, Imaging of angiogenesis: from microscope to clinic. Nat Med, 2003. 9(6): p. 713-25.
26. Bikfalvi, A. and R. Bicknell, Recent advances in angiogenesis, anti-angiogenesis and vascular targeting. Trends Pharmacol Sci, 2002. 23(12): p. 576-82.
27. Augustin, H. G., Translating angiogenesis research into the clinic: the challenges ahead. Br J Radiol, 2003. 76 Spec No 1: p. S3-10.
28. Collins, T. S. and H. I. Hurwitz, Targeting vascular endothelial growth factor and angiogenesis for the treatment of colorectal cancer. Semin Oncol, 2005. 32(1): p. 61-8.
29. Gerber, H. P., Anti-angiogenesis: biology is the foundation for therapy. Drug Discov Today, 2003. 8(8): p. 344-6.
30. Sato, Y., Molecular diagnosis of tumor angiogenesis and anti-angiogenic cancer therapy. Int J Clin Oncol, 2003. 8(4): p. 200-6.
31. Neri, D. and R. Bicknell, Tumour vascular targeting. Nat Rev Cancer, 2005. 5(6): p. 436-46.
32. Islam, M. N., and Iskander, M. N. Microtubulin binding sites as target for developing anticancer agents, Mini Rev Med Chem, 2004, 4(10): p. 1077-104
33. Cao, T. M., et al., Variable hematopoietic graft rejection and graft-versus-host disease in MHC-matched strains of mice. Proc Natl Acad Sci USA, 2003. 100(20): p. 11571-6.
34 Ravelli, R. B., et al., Insight into tubulin regulation from a complex with colchicine and a stathmin-like domain. Nature, 2004. 428(6979): p. 198-202.
35. Nguyen, T. L. et al. A common pharmacophore for a diverse set of colchicine site inhibitors using a structure-based approach. J Med Chem 48, 6107-16 (2005).
36. Jones, G., Willett, P., Glen, R. C., Leach, A. R. & Taylor, R. Development and validation of a genetic algorithm for flexible docking. J Mol Biol 267, 727-48 (1997).
37. Camille George Wermuth. *The practice of medicinal chemistry, Part VII.* 1996 Accademic Press.
38. K. T. Hansen, P. Faarup, H, Bundgaard. Carbamate Ester Prodrug of Dopaminergic Compounds: Synthesis, Stability, and Bioconversion. *J. Pharm. Sci.* 1991, 80(8), 793.
39. Y. Igarashi, E. Yanagisawa, T. Ohshima, S. Takeda, M. Aburada, K. Miyamoto. Synthesis and Evaluation of Carbamate Prodrugs of a Phenolic Compound. *Chem. Pharm. Bull.* 2007, 55(2), 328

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

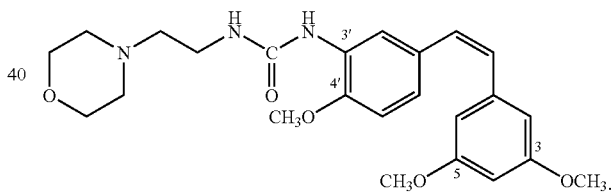

We claim:

1. A water soluble stilbene derivative having the structural formula: